(12) United States Patent
Turner et al.

(10) Patent No.: US 7,943,122 B2
(45) Date of Patent: *May 17, 2011

(54) ATTENUATED BACTERIA USEFUL IN VACCINES

(75) Inventors: Arthur Keith Turner, Cambridge (GB); Judith Greenwood, Cambridge (GB); Jonathan Clive Stephens, Cambridge (GB); Juliet Claire Beavis, Cambridge (GB); Michael James Darsley, Cambridge (GB)

(73) Assignee: Acambis Research Limited, Cambridge (GB)

( * ) Notice: Subject to any disclaimer, the term of this patent is extended or adjusted under 35 U.S.C. 154(b) by 1485 days.

This patent is subject to a terminal disclaimer.

(21) Appl. No.: 10/489,273

(22) PCT Filed: Sep. 11, 2002

(86) PCT No.: PCT/GB02/04164
§ 371 (c)(1),
(2), (4) Date: Sep. 22, 2004

(87) PCT Pub. No.: WO03/022307
PCT Pub. Date: Mar. 20, 2003

(65) Prior Publication Data
US 2005/0054075 A1 Mar. 10, 2005

(30) Foreign Application Priority Data

Sep. 11, 2001 (GB) .................... 0121998.9

(51) Int. Cl.
*A61K 39/02* (2006.01)
*A61K 39/108* (2006.01)
*A61K 48/00* (2006.01)
*A01N 63/00* (2006.01)
*A01N 65/00* (2009.01)

(52) U.S. Cl. ................ 424/93.1; 424/93.2; 424/93.4; 424/241.1; 424/257.1

(58) Field of Classification Search .............. None
See application file for complete search history.

(56) References Cited

U.S. PATENT DOCUMENTS

| | | | |
|---|---|---|---|
| 6,019,982 A | 2/2000 | Clements et al. | |
| 7,393,525 B2 * | 7/2008 | Powell et al. ............... | 424/93.2 |
| 7,399,474 B2 * | 7/2008 | Altboum et al. ............ | 424/190.1 |
| 2004/0253710 A1 | 12/2004 | Turner et al. | |

FOREIGN PATENT DOCUMENTS

| EP | 0 087 735 A | 11/1983 |
|---|---|---|
| EP | 0322237 B1 | 3/1994 |
| EP | 0400958 B1 | 9/1995 |
| EP | 0524205 B1 | 8/1997 |
| WO | WO 92/15689 B1 | 9/1992 |
| WO | 99/49026 A | 9/1999 |
| WO | 99/61634 | 12/1999 |
| WO | 00/37106 | 6/2000 |
| WO | 01/19998 A | 3/2001 |
| WO | WO 03/022306 A2 | 3/2003 |

OTHER PUBLICATIONS

Bourgeois et al, Abstracts of GEneral Meeting of ASM, 2001, 101:344 Abstract only.*
Turner et al, Infection and Immunity, Feb. 2006, 74/2:1062-1071.*
Creighton, In: Proteins: Structures and Molecular Properties, 1984, pp. 314-315.*
Bowie et al, Science, vol. 247:1306-1310.*
Kumar et al PNAS, 1991, 87:1337-1341.*
Nosoh et al, In: Protein Stability and Stabilization through Protein Engineering, 1991, pp. 197-217.*
Jertborn et al, VAccine, 1998, 16(2/3):255-260.*
Svennerholm et al Best Practices and Research Clinical Gastroenterology, 2004, 18/2:421-445.*
Sizemore et al, Expert Rev. VAccine, 2004, 3/5:585-595.*
Boedeker, Current Opinion Gastroenterology, 2005, 21/1:5-19.*
Byrd et al, Advanced Drug Delivery Reviews, 2005, 57:1362-1380.*
Qdari et al, VAccine, 2000, 18:2704-2712.*
Creighton et al In: Protein Structure: A Practical Approach, 1989, pp. 184-186.*
Aitken et al. "Recombinant enterotoxins as vaccines against *Escherichia coli*-mediated diarrhoea" Vaccine 11:227-233 (1993).
Burkardt et al. "Relationship of group P1 plasmids revealed by heteroduplex experiments: RP1, RP4, R68 and RK2 are identical" J. Gen. Microbiol. 114:341-348 (1979).
Chatfield et al. "Evaluation of *Salmonella typhimurium* strains harbouring defined mutations in *htrA* and *aroA* in the murine salmonellosis model" Microbial Pathogen. 12:145-151 (1992).
Chatfield et al. "Use of the *nirB* promoter to direct the stable expression of heterologous antigens in *Salmonella* oral vaccine strains: Development of a single-dose oral tetanus vaccine" Biotechnol. 10:888-892 (1992).
Chatfield et al. "Role of *ompR*-dependent genes in *Salmonella typhimurium* virulence: Mutants deficient in both *OmpC* and *OmpF* are attenuated in vivo" Infect. Immun. 59:449-452 (1991).
Chang et al. "Construction and characterization of amplifiable multicopy DNA cloning vehicles derived from the P15A cryptic miniplasmid" J. Bacteriol. 134:1141-1156 (1978).
Chong et al. "LT(R192G), a non-toxic mutant of the heat-labile enterotoxin of *Escherichia coli*, elicits enhanced humoral and cellular immune responses associated with protection against lethal oral challenge with *Salmonella* spp." Vaccine 16:732-740 (1998).
Cieplak et al. "Site-directed mutagenic alteration of potential active-site residues of the A subunit of *Escherichia coli* heat-labile enterotoxin" J. Biol. Chem. 270:30545-30550 (1995).

(Continued)

Primary Examiner — N. M Minnifield
(74) Attorney, Agent, or Firm — Nixon & Vanderhye P.C.

(57) ABSTRACT

The invention provides strains of bacteria, especially enterotoxigenic *E. coli*, attenuated by mutations in the genes encoding enterotoxins (LT, ST, EAST1) and optionally further attenuated by deletion of additional chromosomal genes. In addition the invention provides strains of attenuated bacteria expressing immunogenic but non-toxic variants of one or more of these enterotoxins. These bacteria are useful as a vaccine against diarrhoeal disease.

17 Claims, 21 Drawing Sheets

OTHER PUBLICATIONS

Clements "Construction of a nontoxic fusion peptide for immunization against *Escherichia coli* strains that produce heat-labile and heat-stable enterotoxins" Infect. Immun. 58:1159-1166 (1990).

Cravioto "Role of transmissible plasmids in enterotoxin production" Ph.D. Thesis pp. 37-39, 91-97, 114-115, 120-124, 234-236, 240 and 262 University of London, London United Kingdom (1980).

Cravioto et al. "Risk of diarrhea during the first year of life associated with initial and subsequent colonization by specific enteropathogens" Am. J. Epidemiol. 131:886-904 (1990).

Curtis III et al. "*Salmonella typhimurium* deletion mutants lacking adenylate cyclase and cyclic AMP receptor protein are avirulent and immunogenic" Infect. Immun. 55:3035-3043 (1987).

Dougan et al. "Construction and characterization of vaccine strains of *Salmonella* harboring mutations in two different *aro* genes" J. Infect. Dis. 158:1329-1335 (1988).

Dunstan et al. "Use of in vivo-regulated promoters to deliver antigens from attenuated *Salmonella enterica* var. Typhimurium" Infect. Immun. 67:5133-5141 (1999).

Everest et al. "Expression of LacZ from the *htrA*, *nirB* and *groE* promoters in a *Salmonella* vaccine strain: Influence of growth in a mammalian cells" FEMS Microbiology Lett. 126:97-102 (1995).

Gerdes et al. "Unique type of plasmid maintenance function: Postsegregational killing of plasmid-free cells" Proc. Natl. Acad. Sci. USA 83:3116-3120 (1986).

Gerdes et al. "The *hok* killer gene family in gram-negative bacteria" New Biologist 2:946-956 (1990).

Hohmann et al. "*phoP/phoQ*-deleted *Salmonella typhi* (Ty800) is a safe and immunogenic single-dose typhoid fever vaccine in volunteers" J. Infect. Dis. 173:1408-1414 (1996).

Hone et al. "Construction of defined *galE* mutants of *Salmonella* for use as vaccines" J. Infect. Dis. 156:167-174 (1987).

Jones et al. "Oral vaccination of calves against experimental *Salmonellosis* using a double *aro* mutant of *Salmonella typhimurium*" Vaccine 9:29-34 (1991).

Leong et al. "Nucleotide sequence comparison between heat-labile toxin B-subunit cistrons from *Escherichia coli* of human and porcine origin" Infect. Immun. 48:73-77 (1985).

Levine et al. "Attenuated *Salmonella* as live oral vaccines against typhoid fever and as live vectors" J. Biotechnol. 44:193-196 (1996).

Miller et al. "Synthesis of cholera toxin is positively regulated at the transcriptional level by *toxR*" Proc. Natl. Acad. Sci. USA 81:3471-3475 (1984).

Miller et al. "A two-component regulatory system (*phoP phoQ*) controls *Salmonella typhimurium* virulence" Proc. Natl. Acad. Sci. USA 86:5054-5058 (1989).

Milton et al. "Flagellin A is essential for the virulence of *Vibrio anguillarum*" J. Bacteriol. 178:1310-1319 (1996).

Pickard et al. "Characterization of defined *ompR* mutants of *Salmonella typhi*: *ompR* is involved in the regulation of Vi polysaccharide expression" Infect. Immun. 62:3984-3993 (1994).

Rappuoli et al. "Structure and mucosal adjuvanticity of cholera and *Escherichia coli* heat-labile enterotoxins" Immunol. Today 20:493-500 (1999).

Roberts et al. "The *parDE* operon of the broad-host-range plasmid RK2 specifies growth inhibition associated with plasmid loss" J. Mol. Biol. 237:35-51 (1994).

Rudin et al. "Monoclonal antibodies against fimbrial subunits of colonization factor antigen I (CFA/I) inhibit binding to human enterocytes and protect against enterotoxigenic *Escherichia coli* expressing heterologous colonization factors" Microbial Pathogen. 20:35-45 (1996).

Sanchez et al. "Recombinant cholera toxin B subunit and gene fusion proteins for oral vaccination" Res. Microbiol. 141:971-979 (1990).

So et al. "Nucleotide sequence of the bacterial transposon Tn1681 encoding a heat-stable (ST) toxin and its identification in enterotoxigenic *Escherichia coli* strains" Proc. Natl. Acad. Sci. USA 77:4011-4015 (1980).

Schlör et al. "Genetic rearrangements of the regions adjacent to genes encoding heat-labile enterotoxins (*eltAB*) of enterotoxigenic *Escherichia coli* strains" Appl. Environ. Microbiol. 66:352-358 (2000).

Simon et al. "A broad host range mobilization system for in vivo genetic engineering: Transposon mutagenesis in gram negative bacteria" Biotechnol. 1:784-791 (1983).

Strugnell et al. "Characterization of a *Salmonella typhimurium aro* vaccine strain expressing the P.69 antigen of *Bordetella pertussis*" Infect. Immun. 60:3994-4002 (1992).

Summers et al. "Multimer resolution systems of ColE1 and ColK: Localisation of the crossover site" Mol. Gen. Genet. 201:334-338 (1985).

Svennerholm et al. "Roles of different coli surface antigens of colonization factor antigen II in colonization by and protective immunogenicity of enterotoxigenic *Escherichia coli* in rabbits" Infect. Immun. 58:341-346 (1990).

Tacket et al. "Safety of live oral *Salmonella typhi* vaccine strains with deletions in *htrA* and *aroC aroD* and immune response in humans" Infect. Immun. 65:452-456 (1997).

Tacket et al. "Enteral immunization and challenge of volunteers given enterotoxigenic *E. coli* CFA/II encapsulated in biodegradable microspheres" Vaccine 12:1270-1274 (1994).

Tacket et al. "Vaccines against enterotoxigenic *Escherichia coli* infections" New Generation Vaccines pp. 875-883 (1997).

Turner et al. "Identification of *Salmonella typhimurium* genes required for colonization of the chicken alimentary tract and for virulence in newly hatched chicks" Infect. Immun. 66:2099-2106 (1998).

Turner et al. "Construction and characterization of generitcally defined *aro omp* mutants of enterotoxigenic *Escherichia coli* and preliminary studies of safety and immunogenicity in humans" Infect. Immun. 69:4969-4979 (2001).

Valdivia et al. "Fluorescence-based isolation of bacterial genes expressed within host cells" Science 277:2007-2011 (1997).

Wolf "Occurrence, distribution and associations of O and H serogroups, colonization fator antigens, and toxins of enterotoxigenic *Escherichia coli*" Clin. Microbiol. Rev. 10:569-584 (1997).

Yamamoto et al. "Detection of the enteroaggregative *Escherichia coli* heat-stable enterotoxin 1 gene sequences in enterotoxigenic *E. coli* strains pathogenic for humans" Infect. Immun. 64:1441-1445 (1996).

Paniagua et al; "Analysis of Incidence of Infection With Enterotoxigenic *Escherichia coli* in a Prospective Cohort Study of Infant Diarrhea in Nicaragua"; Journal of Clinical Microbiology, vol. 35, No. 6, 1997, pp. 1404-1410, XP002221554.

McConnell et al; "Genetic Control and Properties of *coli* Surface Antigens of Colonization Factor Antigen IV PCF8775 of Enterotoxigenic *Escherichia coli*"; Infection and Immunity, vol. 56, No. 8, 1988, pp. 1974-1980, XP009001409.

Yao et al; "Study on Plasmid Coding for Enterotoxin 5. Comparison of Plasmids From CFA-Positive and CFA-Negative ETEC Strains"; Chinese Journal of Microbiology and Immunology (Beijing), vol. 7, No. 5, 1987, pp. 281-285, XP001120094.

Peruski et al; "Phenotypic Diversity of Enterotoxigenic *Escherichia coli* Strains From a Community-Based Study of Pediatric Diarrhea in Periurban Egypt"; Journal of Clinical Microbiology, vol. 37, No. 9, 1999, pp. 2974-2978, XP002221555.

Viboud et al; "Prospective Cohort Study of Enterotoxigenic *Escherichia coli* Infections in Argentinean Children"; Journal of Clinical Microbiology, vol. 37, No. 9, 1999, pp. 2829-2833, XP002221556.

Turner et al.; "Construction and Characterization of Genetically Defined ARO OMP Mutants of Enterotoxigenic *Escherichia coli* and Preliminary Studies of Safety and Immunogenicity in Humans"; Infection and Immunity, vol. 69, No. 8, Aug. 2001, pp. 4969-4949, XP002221198.

Bourgeois et al.; "Comparative Safety and Immunogenicity of Two Attenuated Enterotoxigenic *Escherichia coli* (ETEC) Vaccines in Healthy Adult Volunteers"; Abstracts of the General Meeting of the American Society for, vol. 101, 2001, p. 344 XP002221199.

Turner et al.; "Construction and Characterisation of an Attenuated Strain of Enterotoxigenic *E. coli* for Use as a Live Oral Vaccine"; Immunology Letters, vol. 69, No. 1, Jun. 15, 1999, p. 180 XP001119346.

Donnenberg et al; "Construction of an EAE Deletion Mutant of Enteropathogenic *Escherichia coli* by Using a Positive-Selection Suicide Vector"; Infection and Immunity, American Society for Microbiology, Washington, US, vol. 59, No. 12, Dec. 1991, pp. 4310-4317, XP002121476.

Haberberger et al; "Etiology of Acute Diarrhea Among United States Embassy Personnel and Dependents in Cairo, Egypt"; American Journal of Tropical Medicine and Hygiene, vol. 51, No. 6, 1994, pp. 870-874, XP001119246.

Daley et al. "Genetically modified enterotoxigenic *Escherichia coli* vaccines induce mucosal immune responses without inflammation" gut.bmj.com published online on Jun. 12, 2007 19 pages.

Echeverria et al. "Plasmids coding for colonization factor antigens I and II, heat-labile enterotoxin, and heat-stable enterotoxin A2 in *Escherichia coli*" Infect. Immun. 51:626-630 (1986).

Giron et al. "Simultaneous expression of CFA/I and CS3 colonization factor antigens of enterotoxigenic *Escherichia coli* by ΔaroC, ΔaroD *Salmonella typhi* vaccine strain CVD 908" Vaccine 13:939-948 (1995).

Kaper et al. "A recombinant live oral cholera vaccine" Bio/Technology 2:345-349 (1984).

Levine et al. "Colonization factor antigens I and II and type 1 somatic pili in enterotoxigenic *Escherichia coli*: Relation to enterotoxin type" Infect. Immun. 39:889-897 (1983).

McConnell et al. "Plasmids coding for colonization factor antigen I and heat-stable enterotoxin production isolated from enterotoxigenic *Escherichia coli*: Comparison of their properties" Infect. Immun. 32:927-936 (1981).

Murray et al. "CFA/I-ST plasmids: Comparison of enterotoxigenic *Escherichia coli* (ETEC) of serogroups O25, O63, O78, and O128 and mobilization from an R factor-containing epidemic ETEC isolate" J. Bacteriol. 153:566-570 (1983).

Oyofo et al. "Toxins and colonization factor antigens of enterotoxigenic *Escherichia coli* among residents of Jakarta, Indonesia" Am. J. Trop. Med. Hyg. 65:120-124 (2001).

Qadri et al. "Prevalence of toxin types and colonization factors in enterotoxigenic *Escherichia coli* isolated during a 2-year period from diarrheal patients in Bangladesh" J. Clin. Microbiol. 38:27-31 (2000).

Reis et al. "Transfer of a CFA/I-ST plasmid promoted by a conjugative plasmid in a strain of *Escherichia coli* of serotype Oi28ac:H12" Infect. and Immun. 29:140-143 (1980).

Sommerfelt et al. "Mechanism of spontaneous loss of heat-stable toxin (STa) production in enterotoxigenic *Escherichia coli*" APMIS 97:436-440 (1989).

Thomas et al. "In strains of *Escherichia coli* O167 a single plasmid encodes for the coli surface antigens CS5 and CS6 of putative colonization factor PCF8775, heat-stable enterotoxin, and colicin la" Infect. Immun. 55:1929-1931 (1987).

* cited by examiner

Step 1
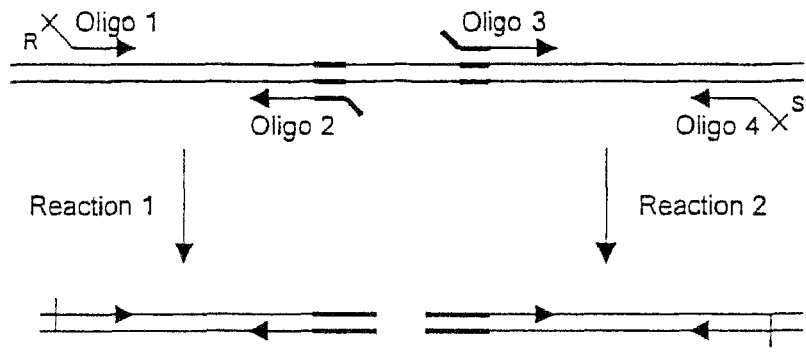
Reaction 1 | Reaction 2
Step 2
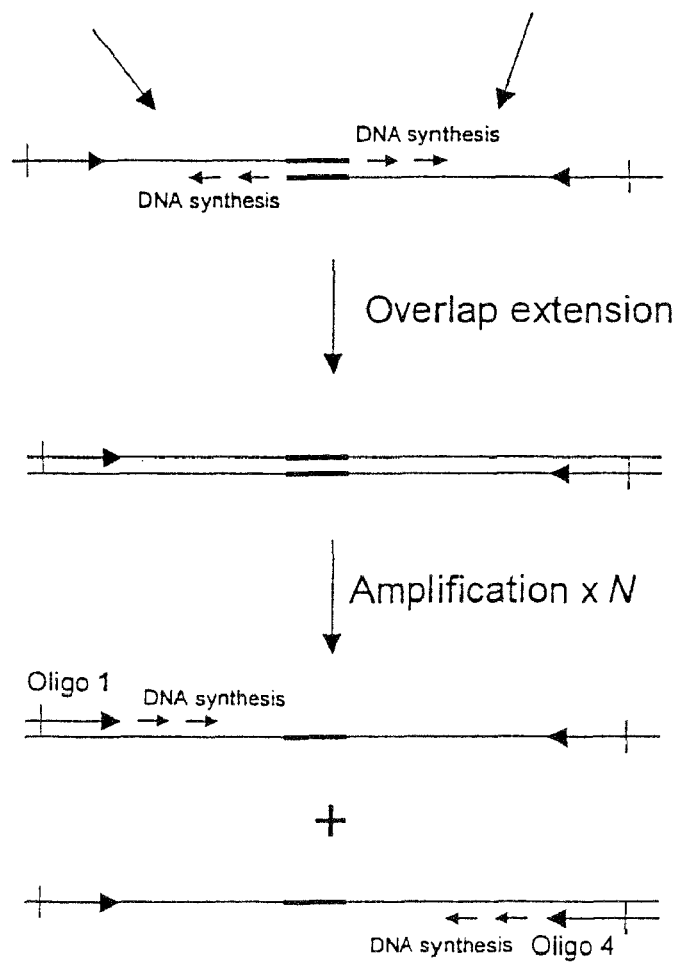
Figure 3.

Figure 5.

```
                                        4764
                   4794                            47101
1    TTTTCGGTCG CCGAAAAAGA TAATATTACT ATGCTCTTCG TAGCGGAGAG

51   TATAGTATGA TGTTCATCAC AAAAAAAATA AAAAGTTTG CGCAACCGTT
                                                  EST-01
101  CTGATTTTGA TTCAAATGTT CGTGGATGCC ATGTTCCGGA GGTAATATGA

151  AGAAATCAAT ATTATTTATT TTTCTTTCTG TATTGTCTTT TCACCTTTC

201  GCTCAGGATG CTAAACCAGT AGAGTCTTCA AAAGAAAAAA TCACACTAGA
                                                     47114
251  ATCAAAAAAA TGTAACATTG CAAAAAAAG TAATAAAAGT GGTCCTGAAA
        47114                                    4765
301  GCATGAATAG TAGCAATTAC TGCTGTGAAT TGTGTTGTAA TCCTGCTTGT 47103
               4792
         4765
351  ACCGGGTGCT ATTAATAATA TAAAGGGAAC TAAACAGTTC CCTTTATATT 4797
                       47115
401  TGTGTGCGCC GTGGCTGGCG CTGTTCTTCA ACTGTGGAGG CTGAAGAACG

451  ACTAAGAGGT GAAAGTCCTC CACACACCCG GTGAGGGGAA GTGTTAGCGG

501  AAGGCAAGGT GATCCTACCC ACGTAATATG GACACAGGCC TAAGCGAGGT

551  TCTGGTTTTA AATTGCTCCG GACTGAGGCC GCCACACCAA CTGTGCCGCC

601  GCCACCGATT GTAATCACAT TCGATATAAT TAAATACCGT TGCCCGCATT

651  ATTTCCCGGC TGATAAAGTG TTCTCCATGG ATACATTCCA CTTTCAGCGA

701  ATGAAAGAAG CTTTCCACGC AGGCATTATC GTAGCAGCAA CCTTTTGCGC

751  TCATACTTTC CACGCAGATT ATGCCGCTTC AGTTGCGCCT GATAATCTGC

801  TGAACAGTAC TGGCCTCCAC GGTCCGTGTG AACGATAACG TTCCGGGGCC
                                   47100
851  TCTTACGCCG CCACAGCGCC ATCTGCAGGG CATCGCAGGC CAGTTGCGCC
             4799
901  GTCATGCGTG GCGACATTGA CCAGCCAATA ACGGCACGTG ACCACAGGTC
```

Figure 6:

```
   1    GTTGGGTTGA GCCTGTACAT AGATTTGTGT AATTGCCTGA TTTTGATATG
                 ─── 4775 ──→
  51    TTCAATCCAG CATCAAATGA AGGTTAATTT ATGGACGAAA AACAGTTACA
 101    GACTCTGGCT AACGAACTGG CCAAAAACCT CAAAACCCCT GAAGACCTCA
 151    GTCAGTTTGA TCGGCTGCTG AAAAAGCTCA GCGTTGAAGC CGCTCTCAAT
 201    GCAGAGATGA CACACCATCT TGGGTATGAG AAAAATCAGT CCAGACCAGG
 251    AGCTAACTCC CGCAACGGTT ATTCCACAAA GACCGTTATC ACAGGCGACG
 301    GTCCACTGGA ACTGCGTACT CCGCGCGATC GTGACGGTAC CTTCGAACCA
 351    CAACTGGTAA AGAAAATCA GACCCGTATT ACCGGGATGG ATAACCAGAT
 401    CCTCTCGTTG TATGCCAAAG GGATGACCAC CCGTGAGATA GCCGCTGCGT
 451    TCAAAGAACT GTATGACGCA GATGTTTCAC CGGCACTGAT ATCAAAGGTT
 501    ACCGATGCCG TGATGGAGCA GGTTGTAGAA TGGCAAAACC GACCACTGGA
 551    TGCTGTTTAC CCCATTGTTT ATCTTGACTG TATCGTCCTG AAAGTTCGGC
 601    AGGACAGTCG CGTCATCAAC AAATCGGTGT TCCTGGCACT GGGCATCAAT
                            ─── 4748 ──→ ─ 4749 ─→
 651    ATCGAAGGTC AGAAAGAACT GCTGGGTATG TGGCTGGCCG AAAATGAAGG
        ──→
 701    GGCGAAGTTC TGGCTCAATG TGCTGACTGA ACTGAAAAAC CGCGGTCTGA
                                          ←── 4750 ·
 751    ACGATATCCT CATCGCCTGT GTGGATGGCC TGAAAGGCTT CCCGGATGCC
                                                          ←
 801    ATCAACACAG TATATCCGAA GGCCCGCATC CAGTTATGCA TCGTGCATAT
                             ─── 4751 ──→
 851    GGTGCGCAAC AGCCTGCGCT TCGTGTCATG GAAGGACTAC AAAGCCGTCA
 901    CTCGCGACCT GAAAGCGATT TATCAGGCTC CCACGGAAGA GGCAGGTCAG
 951    CAGGCCCTGG AAGCGTTCGC TGCGGCCTGG GACAGTCGCT ATCCTCAGAT
                            ←── 4752 ──── ←── 4753 ─
1001    AAGCCGAAGC TGGCAGGCTA ACTGGCCGAA TCTTGCCACG TTCTTCGCTT
        ←
1051    ATCCAACGGA CATCCGCAAA GTGATCTATA CGACGAATGC CATCGAGTCG
1101    CTAAACAGCG TGATCCGCCA TGCGATCAAA AAGCGTAAAG TGTTCCCGAC
1151    AGACGACTCG GTGAAAAAG TGGTGTGGCT GGCAATCCAG TCTGCGTCCC
                            ←── 4777 ────
1201    GGAAATGGAC GATGCCGTTG AAGGACTGGC GAATGGCAAT GAGCCGCTTT
1251    ATTATCGAGT TCGGTGACCG CCTGGACGGT CACTTCTGAG AAAGGCATTT
1301    ACACAGAATA CTAAACAGGC TCGTTGGGTT
```

Figure 7

```
  1   GGTTGACCCG CTGAAATGCA TTCTTTGCNG AAGTCAGATG TGGTNNACGG
 51   GACTGAAGAG GGGCTACCGT CTGGCAGAGC TGGTCGGGAT GCATGAGCCA
                                                  — 4762 →
101   CTGGCGCGAC AGCGGGTGTG CGGCTGANAG CCGCAGAGGG AAGTTGCGT
      — 4762 →
151   CCATTTTACG GGGATGGAG CCAAAAAAAC CGCCAATCAT ACCCTGTATC
201   AATCAGAGTC ATCCTGTTTA ATAGTCATTT CTGTTCATAT GGTGCACAAG
251   GAGTGTTGAA GCAACATCCG TTTTGTGGTG TTTTTTAAT CTTTTTGGGA
                                                  — 4772 →
301   TTTTAATTCC TATCGATGAA CAGGCGTTTC AGCGGTCGGG ACTAAAAATC
      — 4772 →
351   ACCACCACTT CGGGTCATCC GCCTTCATCT CCGCTTCTGT TTCGTATAAA
401   TCAAAACGAC GGCAGGTATG GCAGAACGTG ACGTATTCGT GCGGTGAATC
451   CGGGTACATT TTGTGGAAGG TTTCCCAGAA ACAGACCGTG CAGGAGGGAT
501   GACCGGCGAT AAAGTCTGTA ATACGGACT GATAAGGGTG ATTATTGGCT
551   CTGGCGACGG CTTTCAGAAC CTCTTTCACC ATTCTGGTGT GGACTTTCTG
601   GTGCTCCAGG TTGTGTGACA TGGGAACTCA TTCTGGATGG TTACTCTGAA
651   AGCCCATATT CTGCCCCCCC CCGATTTGCA GCCGCCAGGC TGCCGTGGTT
                                                   — Pfor →
701   CAAGTCGCGA CTAATAAAAA TAATCAGGTT GCCATGATTC AATGTACACC
751   TTTCTCACAT TCGTCTCCGG CATGAAAACG ATGCACTCTT CCTTTATCGC
801   TTTCACTACA CATTTTATCC TCGCATGGAT GTTTATAAAA AACATGATTG
851   ACATCATGTT GCATATATGT TAAATAAAAC AAGTGGCGTT ATCTTTTCC
           ← 4773 ——
             ← Prev ——
901   GGATTGTCTT CTTGTATGAT ATATAAGTTT TCCTCGATGA AAAA
```

Figure 8:

```
                                                                EST-01
AATAAAAAAG TTTGCGCAAC CGTTCTGATT TTGATACAAA TGTTCGTGGA    50
                                 ─────────────────────────────►
TGCCATGTTC CGGAGGTAAT ATGAAGAAAT CAATATTATT TATTTTTCTT   100
                       Start codon
TCTGTATTGT CTTTTTCACC TTTCGCTCAG GATGCTAAAC CAGTAGAGTC   150

TTCAAAAGAA AAAATCACAC TAGAATCAAA AAAATGTAAC ATTGCAAAAA   200
                                47120
AAAGTAATAA AAGTGGTCCT GAAAGCATGA ATAGTAGCAA TTACTGCTGT   250
                         ◄────────────────────────
                                4765
GAATTGTGTT GTAATCCTGC TTGTACCGGG TGCTATTAAT AATATAAAGG   300
                 ◄────────────────────────
                                        Stop codon    47121
GAACTAAACA GTTCCCTTTA TATTTGGTCT GATTCTGATG ATGTCTGTAA   350
                                                ─────────────►
                                              47106
CGTATGTACC TGTTGCTTTG TTGAATAAAT CGAACTTTTG CTGAGTTGAA   400
─►                                   ───────────────────────►

GGAGCAGAGC ACGCATCATC CGGCAACATG AGTCGTTCCA TGGCAAAGCA   450

GAAGTTCAGA ATCACCAACT GGCGCAGCCA CAACAAAGCC CTTATCCTCC   500

GTGGCACCAT CACTTTCTGG CGGGATGGCG AGGCAATTCA GGCCTGGTAT   550

GAGTCAGCAA CCCCCTCATC ACGGGGACGA CCTCAGCGTT ATTCTGACCT   600
                                           47112
TGCTATTACC ACTTTTTTTG TGATTAAACG CGTATTCCGG CTGACCGACC   650
                        ◄────────────────────────

CTGCGGGCTT GAACTGCCCC CGAAAGTTGG ACAGTTTATT GTTAGACGGC   700
     47113                                    ◄─────
◄──────────
TAGCTGTGCC TGAGTCCGGT ATTCTTACCC GGGCTCAGGC CATTTAACCT   750

TGAGCTAATC CGCTCATTGT TAATCGATAT ACTCCTCGAC TACTCTTCGA   800

CGCTCTTTTG TACTATAATA AGCTTTTTCT GCTTCAGCCG GGACTCCATA   850

CCGCGCTGAT GCCTGCCGTT CCATTCCTGC TGTGTAAGCG TCAACGGAGC   900

ACCGTATTGA CGCTCATTTA TTGGTGAGTA CTACGTTCCA TGGCAGGAGT   950

TCGCCAACTC GGTTGGAAGG CCATTCCGGC AGTACGCTCA GAATATGGCG  1000

CAGATACGCT TCCGGATCGA TACCGTTCAG ACGGCAGGTG CCGATCATGC  1050

CCGTACAGCA GTGCTCCACG CTCGCCCGCC GTGATCGCTA CCGAAGAACA  1100

CGTAATTTTT CTTTCCCGAG ACCAGACTTG CACGAAAGCG CTCTTTCCGC  1150

TGGTATTGTC CGCTCTGCCA GACCGTATTA CAC                   1183
```

Figure 11

```
   1   CTGGAGGAAT ACGTGGATAA AATTTCGTT GATGAAGCAG TAAATGAGCT
  51   GCAAACCATT CAGGACATGT TGCGCTGGTC GGTGAGCCGC TTCAGCGCGG
 101   CAAATATCTG GTACGGTCAC GGTACCGATA ACCCGTGGGA TGAAGCCGTA
 151   CAGCTGGTGT TGCCTTCGCT CTACCTGCCG CTGGATATTC CGGAAGATAT
 201   GCGCACCGCG CGTCTGACCT CCAGCGAAAA ACACCGTATT GTTGAACGCG
 251   TGATCCGCCG CGTCAATGAA CGCATTCCGG TGGCTTACCT GACCAACAAA
                                    ── 4731 ──▶
 301   GCGTGGTTCT GCGGCCATGA ATTTTACGTC GATGAACGCG TGCTGGTGCC
 351   GCGCTCGCCG ATTGGTGAAC TGATCAACAA TAAATTTGCC GGACTTATCA
 401   GCAAGCAACC GCAGCATATT TTAGATATGT GTACTGGTAG CGGCTGCATC
 451   GCCATTGCCT GTGCTTATGC CTTCCCGGAT GCAGAAGTCG ACGCGGTGGA
 501   TATCTCTCCA GACGCGCTGG CGGTTGCTGA ACAGAACATC GAAGAACACG
 551   GTCTGATCCA CAACGTCATT CCGATTCGTT CCGATCTGTT CCGCGACTTG
 601   CCGAAAGTGC AGTACGACCT GATTGTCACT AACCCGCCGT ATGTCGATGC
 651   GGAAGATATG TCCGACCTGC AAACGAATA CCGCCACGAG CCGGAACTGG
 701   GCCTGGCATC TGGCACTGAC GGCCTGAAAC TGACGCGTCG CATTCTCGGT
 751   AACGCGGCAG ATTACCTTGC TGATGATGGC GTGTTGATTT GTGAAGTCGG
 801   CAACAGCATG GTACATCTTA TGGAACAATA TCCGGATGTT CCGTTCACCT
                                    ── TT35 ──▶
 851   GGCTGGAGTT TGATAACGGC GGCGATGGTG TGTTTATGCT CACCAAAGAG
 901   CAGCTTATTG CCGCACGAGA ACATTTCGCG ATTTATAAAG ATTAAGTAAA
            ── 47116 ──▶
 951   CACGCAAACA CAACAATAAC GGAGCCGTGA TGGCTGGAAA CACAATTGGA
1001   CAACTCTTTC GCGTAACCAC CTTCGGCGAA TCGCACGGGC TGGCGCTCGG
1051   CTGCATCGTC GATGGTGTTC CGCCAGGCAT TCCGCTGACG GAAGCGGACC
1101   TGCAACATGA CCTCGACCGT CGTCGCCCTG GGACATCGCG CTATACCACC
1151   CAGCGCCGCG AGCCGGATCA GGTCAAAATT CTCTCCGGTG TTTTTGAAGG
1201   CGTTACTACC GGCACCAGCA TTGGCTTGTT GATCGAAAAC ACTGACCAGC
1251   GCTCTCAGGA TTACAGTGCG ATTAAGGACG TTTTCCGTCC AGGCCATGCC
                                                 ◀── 47118 ──
1301   GATTACACCT ACGAACAAAA ATACGGTCTG CGCGATTATC GCGGCGGTGG
1351   ACGTTCTTCC GCCCGCGAAA CCGCCATGCG CGTGGCGGCA GGAGCTATTG
1401   CCAAAAAATA TCTCGCCGAG AAATTTGGTA TTGAAATCCG TGGCTGCCTG
1451   ACCCAGATGG GCGACATTCC GCTGGATATC AAAGACTGGT CGCAGGTCGA
1501   GCAAAATCCG TTTTTTTGCC CGGACCCCGA CAAAATCGAC GCGTTAGACG
1551   AGTTGATGCG TGCGCTGAAA AAGAGGGCG ACTCCATCGG CGCTAAAGTC
1601   ACCGTTGTTG CCAGTGGCGT TCCTGCCGGA CTTGGCGAGC CGGTCTTTGA
                                                        ──▶
1651   CCGCCTGGAT GCTGACATCG CCCATGCGCT GATGAGCATC AACGCGGTGA
```

```
                ── 47119 ──▶
1701    AAGGCGTGGA AATTGGCGAC GGCTTTGACG TGGTGGCGCT GCGCGGCAGC
1751    CAGAACCGCG ATGAAATCAC CAAAGACGGT TTCCAGAGCA ACCATGCGGG
1801    CGGCATTCTC GGCGGTATCA GCAGCGGGCA GCAAATCATT GCCCATATGG
1851    CGCTGAAACC GACCTCCAGC ATTACCGTGC CGGGTCGTAC CATTAACCGC
1901    TTTGGCGAAG AAGTTGAGAT GATCACCAAA GGCCGTCACG ATCCCTGTGT
1951    CGGGATCCGC GCAGTGCCGA TCGCAGAAGC GATGCTGGCG ATCGTTTTAA
                                         ◀── 47117 ──
2001    TGGATCACCT GTTACGGCAA CGGGCGCAAA ATGCCGATGT GAAGACTGAT
        ◀──
2051    ATTCCACGCT GGTAAAAAAT GAATAAAACC GCGATTGCGC TGCTGGCTCT

2101    GCTTGCCAGT AGCGCCAGCC TGGCAGCGAC GCCGTGGCAA AAATAACCC
2151    AACCTGTGCC GGGTAGCGCA CAATCGATAG GCAGTTTTTC TAATGGCTGT
2201    ATTGTCGGCG CTGACACGCT GCCGATACAG TCCGAACATT ATCAGGTCAT
2251    GCGTACCGAT CAGCGTCGCT ATTTCGGTCA CCCGGATCTG GTGATGTTTA
2301    TCCAGCGTCT GAGTAGCCAG GTGAGCAATC TGGGCATGGG TACGGTGCTG
2351    ATTGGCGATA TGGGGATGCC CGCTGGTGGG CGTTTCAACG GCGGTCATGC
2401    CAGCCACCAG ACCGGACTGG ATGTCGATAT CTTTCTGCAA CTGCCGAAAA
2451    CTCGCTGGAC CTCCGCGCAG CTCTTGCGCC CGCAAGCACT GGACTTAGTT
2501    TCCCGCGACG GTAAACACGT TGTCTCCACG CTGTGGAAGC CAGAAATTTT
2551    CAGCTTGATC AAACTCGCCG CCCAGGACAA AGACGTCACG CGCATTTTTG
2601    TTAATCCGGC GATTAAACAA CAACTTTGCC TTGATGCGGG CACCGATCGC
                                  ◀────── TT20 ──────
2651    GACTGGTTGC GCAAAGTGCG ACCCTGGTTC CAGCATCGCG CGCATATGCA
                                  ◀── 4742 ──────
2701    TGTACGATTA CGTTGCCCTG CCGATAGTCT GGAGTGTGAA GATCAACCTT
2751    TACCGCCATC AGGCGATGGT TGCGGGGCAG AACTGCAAAG CTGGTTTGAA
2801    CCTCCAAAAC CGGGAACAAC AAAGCCTGAG AAGAAGACAC CGCCTCCGTT
2851    GCCGCCTTCC TGCCAGGCGC TACTGGATGA GCACGTGATC TAATGGAAAC
2901    GTTTAATAGC CTGTTTATGG TTTCCCCGCT GTTGCTGGGA GTTCTCTTTT
2951    TTGTCGCCAT GCTGGCGGGA TTTATCGACT CGATTGCCGG TGGCGGTGGG
3001    TTACTCACCA TTCCGGCATT GATGGCAGCG GGGATGTCTC CCGCTAATGC
3051    GCTGGCAACC AATAAACTGC AAGCCTGCGG CGGCTCTATT TCCGCTACTA
```

```
  1  ATGAATAAAG TAAAATTTTA TGTTTTATTT ACGGCGTTAC TATCCTCTCT
 51  ATGTGCACAC GGAGCTCCCC AGTCTATTAC AGAACTATGT TCGGAATATC
101  GCAACACACA AATATATACG ATAAATGACA AAATACTATC ATATACGGAA
151  TCGATGGCAG GCAAAAGAGA AATGGTTATC ATTACATTTA AGAGCGGGCGC
201  AACATTTCAG GTCGAAGTCC CGGGCAGTCA ACATATAGAC TCCCAAAAAA
251  AAGCCATTGA AAGGATGAAG GACACATTAA GAATCGCATA TCTGACCGAG
301  ACCAAAATTG ATAAATTATG TGTATGGAAT AATAAAACCC CCAATTCAAT
351  TGCGGCAATC AGTATGGAAA ACTAG
```

Figure 18

```
         Pfor
         ──────▶
CCGGTACCATGATTCAATGTACACCTTTCTCACATTCGTCTCCCGGCATGA    50

AAACGATGCACTCTTCCTTTATCGCTTTCACTACACACATTTTATCCTCGCA   100

TGGATGTTTATAAAAAACATGATTGACATCATGTTGCATATATGTTAAAT    150
                                            Prev
                                         ◀──────
AAAACAAGTGGGCGTTATCTTTTTCCGGATTGTCTCTTCTTGTATGATATATA  200

AGTAGATCTACGT    213
◀─────
```

ATTENUATED BACTERIA USEFUL IN VACCINES

This application is the US national phase of international application PCT/GB02/04164, filed in English on 11 Sep. 2002, which designated the US. PCT/GB02/04164 claims priority to GB Application No. 0121998.9 filed 11 Sep. 2001. The entire contents of these applications are incorporated herein by reference.

The invention relates to attenuated bacteria useful in vaccines.

BACKGROUND TO THE INVENTION

The principle behind vaccination is to induce an immune response in the recipient, thus providing protection against subsequent challenge with a pathogen. This may be achieved by inoculation with a live attenuated strain of the pathogen, i.e. a strain having reduced virulence such that it does not cause the disease caused by the virulent pathogen while still stimulating a broad immune response.

Using modern genetic techniques, it is now possible to construct site-directed attenuated bacterial strains in which stable attenuating deletions have been created. A number of site-directed mutants of *Salmonella* have been created using this type of technology (2, 7, 9, 14, 19, 35, 36, 37). Mutations in a large number of genes have been reported to be attenuating, including the aro genes (e.g. aroA, aroC, aroD and aroE (15, 18)), pur, htrA (4), ompR, ompF, ompC (2), galE (14), cya, crp (7), phoP (13, 19), rfaY (48), dksA (48), hupA (48), sipC (48) and clpB (48).

One class of bacterium that has been attenuated by such modern genetic techniques is enterotoxigenic *Escherichia coli* (ETEC), which causes diarrhoea. The virulence of (ETEC) strains depends on their expression of fimbrial colonization factor antigens (CFAs) which allow them to attach to and colonize the mucosal surface of the small intestine of their host species. Human adapted ETEC strains express a number of CFAs, the most frequently occurring of which are CFA/I, CFA/II (comprising CS3 expressed with either CS1 or CS2) and CFA/IV (comprising CS6 expressed alone or with either CS4 or CS5). Depending on the geographic location, CFA/I, CFA/II and CFA/IV account for between 50% and 80% of ETEC strains. Many other CFAs have been described, but each of them is found in only a small proportion of ETEC strains (33). Evidence indicates that anti-CFA immune responses are important for protection against ETEC disease (6, 24, 28, 29, 30).

Colonization of the small intestine is accompanied by the secretion of enterotoxins. Two types of enterotoxins have been identified in ETEC strains, the heat labile toxin (LT) and the heat stable toxin (ST). LT is highly homologous in structure to the cholera toxin, a multi-subunit protein of the form $AB_5$. The A subunit is the active component of the toxin, which functions to increase the activity of adenylate cyclase. This is delivered into host cells by the B subunits, which bind to gangliosides on the cell surface. ST is a small (19 amino acid) non-immunogenic polypeptide that has guanylate cyclase stimulating activity. In addition, it has been demonstrated recently that a large proportion of ETEC strains also produce EAST1, a heat-stable toxin similar in size and mode of action to ST but different in sequence, which was originally identified in enteroaggregative *E. coli* strains (34).

It has been proposed that derivatives of ETEC strains, which have lost the ability to produce toxins, may be effective live vaccines against virulent isolates. A derivative of a wild-type ETEC strain, E1392/75, that has spontaneously lost the ST and LT activities but which continues to express CFA/II was identified and designated E1392/75-2A (5). In human volunteer studies, oral vaccination with $2 \times 10^{10}$ cfu E1392/75-2A gave 75% protection against challenge with a toxin-expressing ETEC from a different serotype but which expressed the same CFAs (reviewed by (30)). However, approximately 15% of vaccinees experienced mild diarrhoea as a side effect of the vaccine. It was concluded that further attenuation of this strain was required before it could be considered for use as a live vaccine against ETEC infections.

Two derivatives of E1392/75-2A were generated by targeted deletion of potential attenuating genes and evaluated in clinical trials (32, 38). It was demonstrated that both of the derivatives (PTL002, ΔaroC/ΔompR, and PTL003, ΔaroC/ΔompC/ΔompF) were attenuated when compared to the parent strain and caused no clinical symptoms in volunteers who ingested up to $5 \times 10^9$ cfu of freshly harvested live organisms. All volunteers receiving the maximum dose of these candidate vaccines generated specific immune responses against the CFA/II antigen expressed by the strains.

SUMMARY OF THE INVENTION

An effective vaccine against ETEC must immunize against CFA/I, CFA/II and CFA/IV as a minimum, and therefore attenuated strains expressing all of these antigens are required. Thus, it is required that the genes expressing the toxins LT, ST and EAST1 are inactivated or deleted from strains expressing all of these CFAs. Toxin minus strains have previously been suggested as a starting point for developing a live attenuated multi-strain vaccine against ETEC (Chatfield, 38). There was, however, no explanation in Chatfield as to how such strains might be generated.

We have now found that there are particular difficulties associated with the generation of a strain expressing CFA/I or a strain expressing CS5 and CS6 from which the toxin genes, especially the ST gene, have been deleted. We have devised a novel strategy and suicide vector for overcoming these difficulties and producing toxin minus forms of these strains.

Without wishing to be bound by this theory, we believe that the reason that ST minus forms of strains expressing CFA/I or CS5 and CS6 were difficult to generate was that the CFA/CS genes are closely linked to the ST gene and are on the same plasmid. In a global review of epidemiological studies in which sufficient data had been collected (33) it is reported that of 204 CFA/I expressing strains, all 204 of them expressed ST, either alone (149/204) or in combination with LT (55/204). Further, more recent studies have confirmed this finding, e.g. Qadri et al (22), where all of 87 CFA/I expressing strains isolated in a two year period in Bangladesh expressed ST, either alone or in combination with LT. No strains were identified which expressed CFA/I and LT alone, suggesting an extremely tight genetic linkage between the ST and CFA/I loci. Numerous scientific papers document the close linkage between CFA/I and ST genes in ETEC strains, to the extent that whenever an effort has been made to derive a strain which has lost one of these loci, the other has always been lost concurrently. In no instance of which we are aware has it been possible to separate the two loci by deletion or inactivation of the ST gene and produce a strain that still expresses CFA/I (42-46).

The invention provides a bacterial cell which expresses colonization factor antigen CFA/I from a native plasmid but does not express heat stable toxin (ST). The invention also provides a bacterial cell which expresses colonization factor antigen CS5 from a native plasmid and/or expresses colonization factor antigen CS6 from a native plasmid, but does not express heat stable toxin (ST). The LT gene and the EAST1 gene may also be deleted or inactivated in the cells of the invention. The cells generally contain further attenuating mutations, such as mutations in each of the aroC, ompF and ompC genes, in order to make them acceptable for use in vaccines.

The cells of the invention may be genetically engineered to express a heterologous antigen, such as a non-toxic component or form of LT, or a colonization factor antigen (CFA). Such cells induce an immune response against the heterologous antigen as well as the native antigens and hence improve the protection provided by a vaccine.

The invention includes a vaccine against diarrhoea containing the cells of the invention. Preferably, the vaccine includes a blend of different cells which between them carry all the most common CFAs, namely CFA/I, CFA/II and CFA/IV.

Furthermore, the invention provides a suicide vector and a method which makes possible the reliable and rapid isolation of the cells of the invention and other bacterial cells containing deleted, inactivated or replaced genes. The vector represents an improvement over known suicide vectors in that it allows more specific and more reliable targeting than known vectors. The vector is less than 5 kb in size (e.g. from 2.5 to 5 kb or from 2.5 to 4 kb) and comprises the sacB region which codes for a product that is toxic to bacteria when grown on sucrose, in which region the IS1 insertion sequence is deleted or inactivated. The small size of the vector and the absence of the IS1 insertion sequence help to prevent the vector from targeting to the wrong place in the cellular DNA.

DETAILED DESCRIPTION OF THE INVENTION

Bacteria Useful in the Invention

The bacterial cells of the invention are generally derived from enterotoxigenic *E. coli* (ETEC) cells by deletion or inactivation of the ST gene and optionally other toxin genes. As mentioned above, ETEC is a class of *E. coli* that cause diarrhoea. They colonise the small intestine. They can be isolated from human clinical samples, typically stools produced whilst suffering from diarrhoea. A standard ETEC strain is H10407, deposited at the ATCC under catalogue #35401.

Infections of ETEC are the single most frequent cause of travellers diarrhoea, causing 3-9 million cases per year amongst visitors to developing countries. In endemic areas, ETEC infections are an important cause of dehydrating diarrhoea in infants and young children, resulting in up to 400,000 deaths a year, predominantly in this age group. In developing countries, the incidence of ETEC infections leading to clinical disease decreases with age, indicating that immunity to ETEC infection can be acquired. In contrast, naive adults from industrialized countries who visit endemic areas are highly susceptible to ETEC infections. However, with prolonged or repeated visits to endemic areas susceptibility to ETEC infections diminishes, suggesting that a live attenuated approach to ETEC vaccination may prove successful.

A vaccine to protect against ETEC diarrhoea in humans must provide protection against the seven major colonization factors and, as a minimum, the heat labile toxin (LT) to ensure that protection against different strains is obtained. In order to achieve this, the same attenuations could be made in a range of different ETEC strains, each with a different colonization factor. This would involve deleting the toxins from all such strains. The present invention provides a panel of suitable strains from which all toxin genes have been completely deleted which can provide the starting point for the generation of a multi-strain vaccine. Alternatively, it may be possible to express multiple colonization factors in a smaller number of strains from which the toxins have been similarly deleted.

Toxin-deleted strains of the present invention were derived from wild-type clinical isolates obtained from a long-term epidemiological study carried out in Egypt by scientists at the US Navy NAMRU3 facility in Cairo. A list of the strains provided is given in the following table.

| Strain | Code | Phenotype | CFA | LT | ST | EAST1 |
|---|---|---|---|---|---|---|
| WS-1858B | A | O71:H- | CFA/I | − | + | + |
| WS-4437A | B | O128:H12 | CFA/I | − | + | − |
| WS-6117A | C | O153:H45 | CFA/I | − | + | + |
| WS-2560B | D | O25:H- | CS4, CS6 | + | + | + |
| WS-2773E | E | O39:H12 | CS5, CS6 | + | + | + |
| WS-4150D | F | O6:H16 | CS2, CS3 | + | − | − |
| WS-6170A | G | O17:H18 | CS2, CS3 | − | + | − |
| WS-3504D | H | O141:H5 | CS2, CS3 | + | + | + |
| WS-3517A | I | O6:H- | CS2, CS3 | − | + | + |
| WS-2252A | J | O15:H18 | CS4, CS6 | + | + | + |
| WS-2511A | K | O4:H- | CS4, CS6 | − | + | + |
| WS-2556A | L | O6:H1 | CS4, CS6 | − | + | + |
| WS-4046A | M | O39:H- | None identified | + | − | N.D. |

It will be clear to those skilled in the art that other strains may be equally suitable as a starting point for the generation of a toxin-deleted, attenuated multi-strain vaccine.

The strains with the codes A, B, E, H & J were attenuated by the specific removal of all known toxin genes and then further manipulated, as described in the accompanying Examples. Resulting toxin-minus strains and strain PTL003 described above were deposited by Acambis Research Limited of Peterhouse Technology Park, 100 Fulbourn Road, Cambridge, CB1 9PT, United Kingdom with the European Collection of Cell Cultures (ECACC), CAMR, Salisbury, Wiltshire SP4 OJG, United Kingdom on 3 Sep. 2001 (accession numbers 010903) or 29 Aug. 2002 (accession numbers 020829) in accordance with the Budapest Treaty. The characteristics of the strains and the accession numbers of those which were deposited are as follows:

| Strain | Parent Strain | Accession number | LPS:flagellin | Antibiotic Resistance | CS proteins | Regulator | Toxin Genes | Example |
|---|---|---|---|---|---|---|---|---|
| E1392/75-2A | E1392/75 | N/A | O6:H16 | Strep | CS1 CS3 | rns | None | |
| PTL003 | E1392/75-2A | 01090302 (submitted as ACM2005) | O6:H16 | Strep | CS1 CS3 | rns | None | |
| ACAM2008 | PTL003 | 02082965 | O6:H16 | None | CS1 CS3 | rns | None | |
| WS-2773E (strain E) | N/A | N/A | O39:H12 | None | CS5 CS6 | ? csvR | ST EAST LT | 3 |

| Strain | Parent Strain | Accession number | LPS:flagellin | Antibiotic Resistance | CS proteins | Regulator | Toxin Genes | Example |
|---|---|---|---|---|---|---|---|---|
| WS-2773E-Tox minus | WS-2773E | 01090305 (submitted as ACM2002) | O39:H12 | None | CS5 CS6 | ? csvR | None | |
| ACAM2006 | WS-2773E-Tox minus | N/A | O39:H12 | None | CS5 CS6 | ? csvR | None | |
| ACAM2012* | ACAM2006 | 02082968 | O39:H12 | None | CS5 CS6 | ? csvR | None | |
| WS-3504D (strain H) | N/A | N/A | O141:H5 | Amp | CS2 CS3 | rns | EAST | 4 |
| WS-3504D-Tox minus | WS-3504D | 01090304 (submitted as ACM2003) | O141:H5 | Amp | CS2 CS3 | rns | None | |
| ACAM2007 | WS-3504D-Tox minus | 02082964 | O141:H5 | None | CS2 CS3 | rns | None | |
| WS-1858B (Strain A) | N/A | N/A | O71:H- | Amp/Tmp/Smz | CFA/I | rns | ST EAST | 2 |
| WS-1858B-Tox minus | WS-1858B | N/A | O71:H- | Amp/Tmp/Smz | CFA/I | rns | None | |
| ACAM2010 | WS-1858B-Tox minus | 02082967 | O71:H- | None | CFA/I | rns | None | |
| WS-2252A (Strain J) | N/A | N/A | O15:H18 | None | CS4 CS6 | cfaD | ST EAST LT | 4 |
| WS-2252A-Tox minus | WS-2252A | 01090306 (submitted as ACM2004) | O15:H18 | None | CS4 CS6 | cfaD | None | |
| ACAM2009 | WS-2252A-Tox minus | 02082966 | O15:H18 | None | CS4 CS6 | cfaD | None | |
| WS-2511A (Strain K) | N/A | N/A | O4:H- | None | CS4 CS6 | cfaD | ST EAST × 2 | N/A |
| Strain K | WS-2511A-Tox minus | N/A | O4:H- | None | CS6 | cfaD | ST EAST × 2 | |

*ACAM2006 contains a lysogenic phage in its chromosome - ACAM2012 is a derivative of ACAM2006 from which a large part of the genome, including several genes critical for phage assembly, have been deleted.

In addition to the strains in the above table, a toxin minus derivative of strain B described in Example 2 below was deposited under accession number 01090303.

The invention includes "descendents" of these deposited cells. A "descendent" is any cell derived from a deposited cell. The descendents of a deposited cell include cells with one or more further attenuating mutations, such as the mutations described below. Descendents also include cells which have been engineered to express heterologous antigens, such as the heterologous antigens described below.

Although the bacteria of the invention are generally *E. coli* bacteria, other types of bacteria may be used. A plasmid in accordance with the invention may be constructed by deleting or inactivating the ST gene in a plasmid native to enterotoxigenic *E. coli*, and then transferring the resulting plasmid to another bacterium. In this way, the other bacterium may be made to carry the CFA/I antigen or the CS5 and CS6 antigens.

The bacteria that are used to make the vaccines of the invention are generally those that infect by the oral route. The bacteria may be those that invade and grow within eukaryotic cells and/or colonize mucosal surfaces. The bacteria are generally gram negative but in some embodiments gram positive bacteria may be used. The bacteria are generally pathogens.

The bacteria used may be from the genus *Escherichia, Salmonella, Shigella* or *Vibrio*.

Other than *E. coli*, examples of the species of bacteria that can be used in the invention are *Salmonella typhimurium*—the cause of salmonellosis in several animal species; *Salmonella typhi*—the cause of human typhoid; *Salmonella enteritidis*—a cause of food poisoning in humans; *Salmonella choleraesuis*—a cause of salmonellosis in pigs; and *Salmonella dublin*—a cause of both a systemic and diarrhoel disease in cattle, especially of new-born calves.

Strains of *E. coli* and *Salmonella* are particularly useful in the invention. *Salmonella* are potent immunogens and are able to stimulate systemic and local cellular and antibody responses. In particular an attenuated strain of *Salmonella typhi* is preferred for use in the invention. Preferred *Salmonella typhi* strains for use in the present invention include CVD908-htrA (ΔaroC ΔaroD ΔhtrA) and CVD908 (ΔaroC ΔaroD) (49). Strains of *E. coli* other than ETEC that may be used include enteropathogenic *E. coli* (EPEC), enteroinvasive *E. coli* (EIEC) and enterohemorrhagic *E. coli* (EHEC).

As used herein, references to a "native" plasmid which expresses CFA/I or CS5/6 mean a plasmid which exists in wild-type cells, for example ETEC cells isolated from a person with diarrhoea. They exclude a plasmid constructed in the laboratory for expression of CFA/I or CS5/6. In a cells of the invention, the ST gene in the native plasmid is deleted or inactivated. However, the CFA/I or CS5/6 gene in the plasmid is functional, i.e. it expresses CFA/I or CS5/6.

Further Mutating the Bacteria

In order for the bacteria to be used in a vaccine, they must generally be further attenuated. The attenuation may, for example, be brought about by deleting or inactivating one or more of the following genes: aroA, aroC, aroD, aroE, pur, htrA, ompC, ompF, ompR, cya, crp, phoP, surA, rfaY, dksA, hupA, sipC and clpB. Preferred combinations of genes include:
  at least one aro gene (e.g. aroA, aroC, aroD or aroE) and at least one omp gene (e.g. ompC, ompF or ompR);
  at least one aro gene (e.g. aroA, aroC, aroD or aroE) and the htrA gene;
  aroC, ompF and ompC.

The further attenuating mutations may be introduced using the suicide vector and methods of the invention or by methods known to those skilled in the art (see ref. 25). Appropriate known methods include cloning the DNA sequence of the wild-type gene into a vector, e.g. a plasmid, and inserting a selectable marker into the cloned DNA sequence or deleting a part of the DNA sequence, resulting in its inactivation. A deletion may be introduced by, for example, cutting the DNA sequence using restriction enzymes that cut at two points in or just outside the coding sequence and ligating together the two ends in the remaining sequence. Alternatively, and more usually now, a mutant allele in which the flanking regions of a target gene are amplified separately and linked directly together in a separate overlap PCR reaction, with omission of the intervening target sequence, can be constructed (32). A plasmid carrying the mutated DNA sequence can be transformed into the bacterium by known techniques such as electroporation and conjugation. It is then possible by suitable selection to identify a mutant wherein the inactivated DNA sequence has recombined into the chromosome of the bacterium and the wild-type DNA sequence has been rendered non-functional by homologous recombination.

Furthermore, the antibiotic resistance genes must generally be removed from the bacteria before they are used in a vaccine. Bacteria isolated from the wild often contain antibiotic resistance genes, such as resistance genes against ampicillin, streptomycin, sulphmethoxazole, kanamycin, trimetheprim and tetracyclin. These genes can be removed using the suicide vector and methods of the invention or by methods known to those skilled in the art.

The Nature of the Mutations

The mutations introduced into the bacterial vaccine to prevent expression of enterotoxins or other virulence genes delete or inactivate the gene. They generally knock-out the function of the gene completely. This may be achieved either by abolishing synthesis of any polypeptide at all from the gene or by making a mutation that results in synthesis of non-functional polypeptide. In order to abolish synthesis of polypeptide, either the entire gene or its 5'-end may be deleted. A deletion or insertion within the coding sequence of a gene may be used to create a gene that synthesises only non-functional polypeptide (e.g. polypeptide that contains only the N-terminal sequence of the wild-type protein). In the case of a toxin gene, the mutation may render the gene product non-toxic.

The mutations are generally non-reverting mutations. These are mutations that show essentially no reversion back to the wild-type when the bacterium is used as a vaccine. Such mutations include insertions and deletions. Insertions and deletions are preferably large, typically at least 10 nucleotides in length up to the length of the entire gene or coding sequence, for example from 10 to 600 nucleotides. Preferably, the whole coding sequence or whole gene is deleted.

The mutations are typically site-directed. They may be specific or selective to the toxin gene or other virulence factor gene. In the case of deleting or inactivating the ST gene in a CFA/I or CS5/CS6 strain, the mutation must specifically target the ST gene without deleting or inactivating the (closely-linked) CFA/I gene, CS5 gene or CS6 gene.

Expression of Heterologous Antigens

An attenuated bacterium of the invention may be genetically engineered to express an antigen that is not expressed by the native bacterium (a "heterologous antigen"), so that the attenuated bacterium acts as a carrier of the heterologous antigen. In the case that the bacterium is an ETEC bacterium, the antigen may be from another species or from another strain of ETEC, so that the vaccine provides protection against the other species or strain. Furthermore, the bacterium may be engineered to express more than one heterologous antigen, in which case the heterologous antigens may be from the same or different species or strains.

The heterologous antigen may be a complete protein, a part of a protein containing an epitope or a fusion protein. The antigen may be from another bacterium, a virus, a yeast or a fungus. More especially, the antigenic sequence may be from a pathogenic strain of *E. coli* (e.g. ETEC). Useful antigens include ETEC colonization factor antigens, non-toxic components or non-toxic mutants of *E. coli* LT (e.g. the B subunit and mutants of the A subunit), LT-ST fusion proteins and cholera toxin B subunit (CT-B) (50-55).

The ETEC CFAs and components thereof are prime candidates for expression as heterologous antigens. To instigate diarrhoeal disease, pathogenic strains of ETEC must be able to colonize the intestine and elaborate enterotoxins. For most strains of ETEC, CFAs that are responsible for adhesion to the intestinal mucosa have been identified. In almost all cases CFAs are expressed as fimbriae on the outer surface of the bacteria. A large number of CFAs have been identified, the most prevalent being CFA/I, CFA/II (includes CS1, CS2, CS3) and CFA/IV (includes CS4, CS5, CS6). Additional antigens include CS17, CS7, CS9, CS14, CS12, PCFO159, PCFO166.

The DNA encoding the heterologous antigen may be expressed from a promoter that is active in vivo. Promoters that have been shown to work well are the nirB promoter (10, 39), the htrA promoter (10), the pagC promoter (57) and the ssaH promoter (58). For expression of the ETEC colonization factor antigens or derivatives of LT, CT or ST, the wild-type promoters could be used.

A DNA construct comprising the promoter operably linked to DNA encoding the heterologous antigen may be made and transformed into the attenuated bacterium using conventional techniques. Transformants containing the DNA construct may be selected, for example by screening for a selectable marker on the construct. Bacteria containing the construct may be grown in vitro before being formulated for administration to the host for vaccination purposes.

Plasmid Stabilisation

In order to prevent loss of the plasmid expressing the heterologous antigen or of a native plasmid, an element may be added to the plasmid which enhances its stability. It is generally the case that the plasmids found in ETEC strains encoding the various colonization factor antigens are low copy number and stable enough to ensure their maintenance over many generations in the absence of specific selection mechanisms. However, following manipulation of these plasmids in accordance with the invention, for example to delete genes for toxins such as ST or other virulence determinants, these stable properties might be impaired. This problem may be alleviated by employing methods for improvement of plasmid stability.

There are a number of "toxin/antitoxin" plasmid stability determining systems known, for example parDE (23) from plasmid RP4 (1), and hok/sok (also known as parB from plasmid R1 or pndAB from plasmid R483 (11, 12)) which could be used to do this. These systems encode two functions: firstly a toxic entity that would kill cells in which it is expressed, which has a long biological half-life, and secondly an antitoxic entity that prevents this killing but has a short biological half-life. In the event that a plasmid encoding these functions is segregated during division the daughter cell which does not contain the plasmid exhausts its supply of antitoxin and is killed by the more persistent toxin moiety. Thus, only cells that continue to harbour the plasmid are maintained in the growing population.

Another system that may be used to enhance the stability of a plasmid in accordance with the invention is a multimer resolution system. Multimer resolution systems confer stability by resolving plasmid multimers into single plasmid copies and hence decreasing the chance of plasmid free daughter cells being generated by random segregation at cell division. A number of site-specific recombination systems which act to resolve plasmid multimers into monomers have been identified. In accordance with such a system, the plasmid to be stabilised contains a recognition site for a site-specific recombinase and the host cell contains a DNA sequence encoding a site-specific recombinase. The recombinase acts on the recognition site and thereby directs proper segregation of the plasmid during cell division. The recombinase may be encoded on the plasmid to be stabilised or in the chromosome of the host cell.

The recombinase is generally a resolvase. Examples of resolvases which may be used in the invention include the Cre recombinase of plasmid P1, the *E. coli* XerC (ArgR) protein, the D protein recombinase of plasmid F, the ParA recombinases of plasmids RP4 and RK2, the site-specific recombinase of plasmid R1, resolvases encoded by the Tn3-like transposable genetic elements and the Rsd resolvase from the *Salmonella dublin* virulence plasmid.

The recognition elements which may be used in the present invention include those for the above recombinases. Any recognition element recognised by the site-specific recombinase employed may be used. Suitable recognition elements include those sites recognised by the XerC site-specific recombinase, such as the cer site of plasmid ColE1 and the similar ckr site of plasmid ColK (59), the psi site of plasmid pSC101 and the cer like site of plasmid pHS-2 from *Shigella flexneri*. Other recognition elements which may be used include the crs site from the *Salmonella dublin* virulence plasmid, the loxP site of plasmid P1, the rfs site of the F plasmid and the res site of the Tn3-like transposable genetic element In a particularly preferred embodiment of the invention, the recombinase is the Rsd resolvase which acts via the crs recognition element. The Rsd/crs system is described in detail in our copending application, UK Patent Application No. 0024203.2.

Formulation of Vaccines

The invention provides a vaccine against diarrhoea comprising an *E. coli* cell of the invention and a pharmaceutically acceptable carrier or diluent. Generally, the vaccine includes a blend of different toxin minus cells (e.g. 2, 3, 4, 5 or 6 cells) which between them carry all the most common CFAs. For example, the vaccine may contain five different strains of toxin minus cell as follows:
(i) a cell which expresses CFA/I (e.g. ECACC Accession No. 01090303 or 02082967)
(ii) a cell which expresses CS5 and CS6 (e.g. ECACC Accession No. 01090305 or 02082968);
(iii) a cell which expresses CS4 and CS6 (e.g. ECACC Accession No. 01090306 or 02082966);
(iv) a cell which expresses CS2 and CS3 (e.g. ECACC Accession No. 01090304 or 02082964); and
(v) a cell which expresses CS1 and CS3 (e.g. PTL003, ECACC Accession No. 01090302 or 02082965).

As mentioned above, the cell deposited under ECACC Accession No. 01090302 (PTL003) has already been tested in two clinical trials and been shown to be safe and immunogenic.

The vaccine may be formulated using known techniques for formulating attenuated bacterial vaccines. The vaccine is advantageously presented for oral administration, for example as a dried stabilised powder for reconstitution in a suitable buffer prior to administration. Reconstitution is advantageously effected in a buffer at a suitable pH to ensure the viability of the bacteria. In order to protect the attenuated bacteria and the vaccine from gastric acidity, a sodium bicarbonate preparation is advantageously administered with each administration of the vaccine. Alternatively the vaccine is presented in a lyophilised encapsulated form.

The vaccine may be used in the vaccination of a mammalian host, particularly a human host. An infection caused by a microorganism, especially a pathogen, may therefore be prevented by administering an effective dose of a vaccine prepared according to the invention. The dosage employed may ultimately be at the discretion of the physician, but will be dependent on various factors including the size and weight of the host and the type of vaccine formulated. However, a dosage comprising the oral administration of from $10^7$ to $10^{11}$, e.g. from $10^8$ to $10^{10}$, bacteria per dose may be convenient for a 70 kg adult human host.

EXAMPLES

The Examples described in this section serve to illustrate the invention.

BRIEF DESCRIPTION OF THE DRAWINGS

FIG. 3: Diagram of method used to create specific gene deletion constructs by overlap extension PCR. Step 1=PCR amplification of two DNA fragments. Step 2=overlap extension PCR using DNA products from reaction 1 and reaction 2 of step 1 and amplification of the overlap extension PCR product. R and S stand for restriction enzyme sites.

FIG. 5: Sequence (SEQ ID NO:1) of the ST gene and flanking regions of the plasmid in strain B showing the open reading frame of the structural gene and the position of all oligonucleotides described in the text and detailed in Table 1.

FIG. 6: Sequence (SEQ ID NO:2) of the EAST1 gene and flanking regions from IS1414 (Genbank #AF143819) showing the open reading frame of the structural gene and the position of all oligonucleotides described in the text and detailed in Table 1.

FIG. 7: Sequence (SEQ ID NO:3) of the LT locus showing the position of the oligonucleotides used to create the deletion construct. The underlined ATG codon near the end of the sequence is the start codon of LTA.

FIG. 8: Sequence (SEQ ID NO:4) of the 3' flanking region of the ST-1 gene determined from strain E showing the position of oligonucleotides described in the text and detailed in Table 1. The open reading frame of the structural gene and the ATG and TAA start and stop codons are underlined.

FIG. 11: Sequence (SEQ ID NO:5) of the aroC gene locus showing the position of the oligonucleotides used to create the deletion construct and of others mentioned in the text and described in Table 1.

FIG. 14: Sequence (SEQ ID NO:6) of the LT-B gene cloned from strain E.

Figure 1:
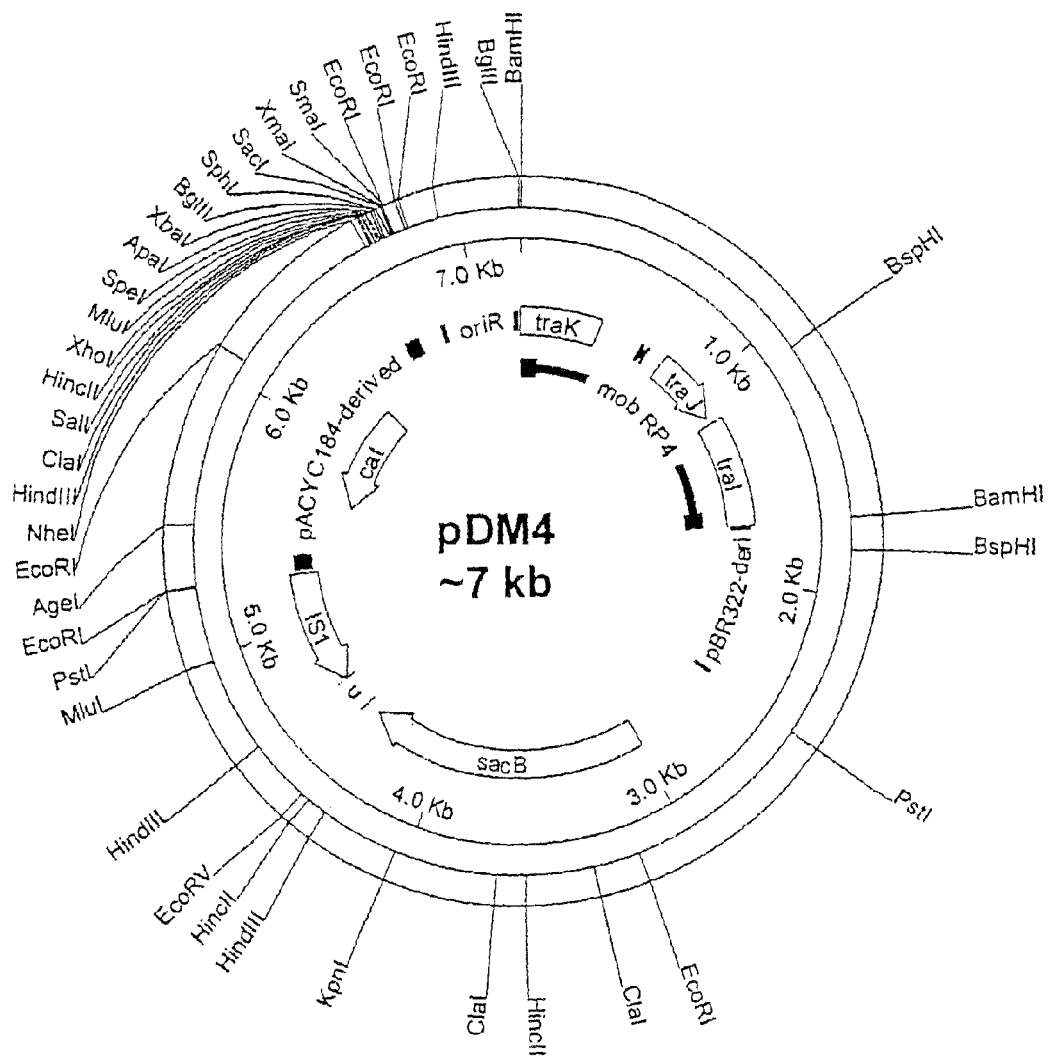
FIG. 1: Map of suicide vector plasmid pDM4. u=unknown sequence, unknown length.
Figure 2:
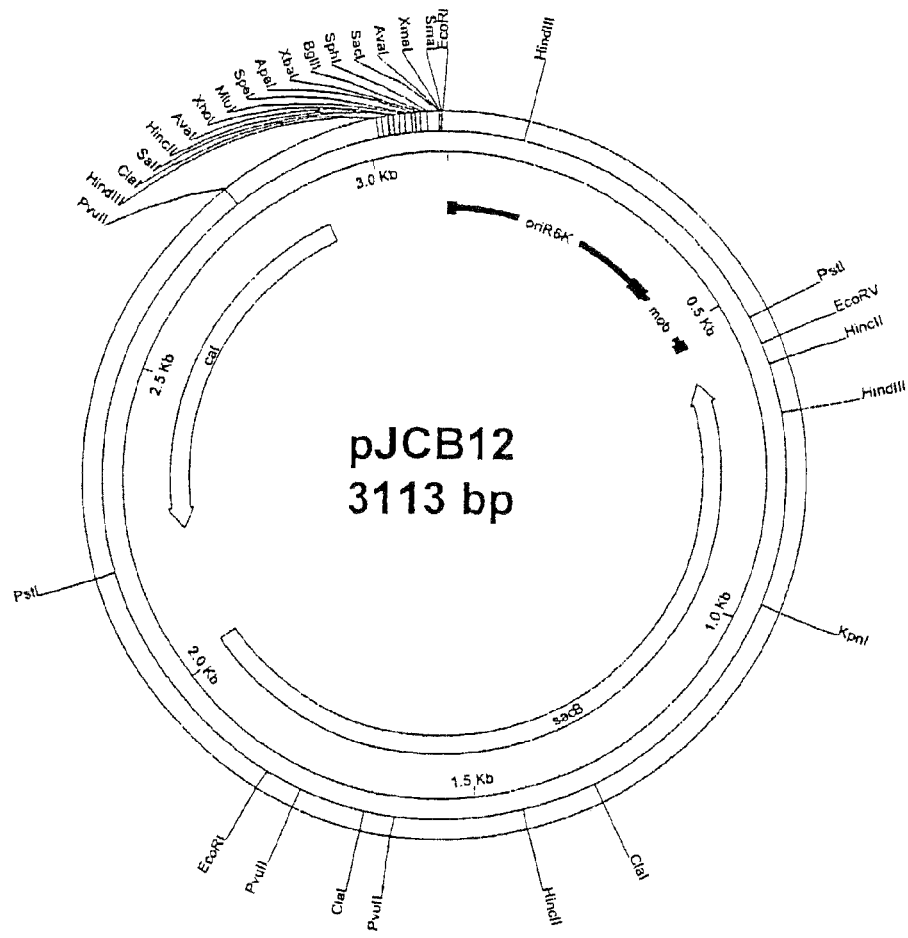
FIG. 2: Map of improved suicide vector pJCB12.

Suicide vector pJCB12 is a modified version of pDM4 in which much of the intergenic and non-functional DNA has been removed. Therefore, there is much less opportunity for incorrect targeting using this suicide vector. Whereas pDM4 is approximately 7 kb in size, pJCB12 is only 3 kb but retains all the key components. In particular, the mobRP4 region of pJCB12 is merely 0.15 kb, and the IS1-like nucleotide sequences have been removed from the sacB region. These modifications are particularly advantageous when manipulating ETEC strains which generally harbour many plasmids that could act as undesirable targets of homologous recombination with components of the suicide vector. In addition, the smaller size of pJCB12 allows easier in vitro manipulation and construction of derivatives because smaller DNA molecules ligate together and transform into E. coli hosts more efficiently, improving the chances of obtaining derivatives of the correct construction. The smaller size also allows greater efficiency when introducing the constructs into recipient bacteria by transformation rather than by conjugation.

Laboratory E. coli strain SM10λpir can be used to transfer pJCB12 and its derivatives to recipient bacterial strains by conjugation because it has the tra functions from plasmid RP4 inserted into its chromosome. However, strain SM10λpir shows relatively low transformation frequencies. For this reason, strain DH5αλpir would normally be used for the construction of pJCB12 derivatives, and once derivatives of the correct construction have been identified these would be transferred to SM10λpir for introduction to recipient strains by conjugation.

Construction of Suicide Vector pJCB12

Suicide vector pJCB12 was constructed by several rounds of overlap extension PCR (31, FIG. 3) using pDM4 plasmid DNA as template. Initially, four fragments were amplified from pDM4 by PCR using the high fidelity DNA polymerase, Pfu Turbo™. These were the oriR6K fragment, amplified using oligonucleotides 4714 and 4715; the mobRP4 fragment amplified using oligonucleotides 4716 and 4717; and the cat gene that was amplified in two parts using oligonucleotides 4718 with 4719 and 4720 with 4721. This was done in order to remove an EcoRI restriction enzyme site within the cat gene. The oriR6K fragment and the mobRP4 were then joined in an overlap extension PCR reaction using oligonucleotides 4714 and 4717. Likewise, the cat fragments were joined using oligonucleotides 4718 and 4721. These two resulting fragments were then joined in a final overlap extension PCR reaction using oligonucleotides 4717 and 4718. The resulting PCR product was ligated and transformed into SY327λpir cells and transformants were selected on L-agar supplemented with chloramphenicol at 20 µg/ml. Transformants harbouring plasmids of the correct size were obtained and one of these, called pDM4A7, was chosen for further manipulation.

At this stage, clearly the oriR6K and cat components of the plasmid pDM4A7 are functional. However, in order to confirm that the mobRP4 locus was functional plasmid pDM4A7 was transformed into strain SM10λpir. These transformants were picked onto L-agar supplemented with chloramphenicol at 15 µg/ml and nalidixic acid at 5 µg/ml. This L-agar was cross-streaked with cells of strain SY327λpir. While chloramphenicol selects those bacterial cells which harbour pDM4A7, nalidixic acid selects for SY327λpir. After overnight incubation, many colonies grew where the strains were cross-streaked, but none grew elswhere on the plate, confirming that pDM4A7 is mobilisable from strain SM10 pir and that the mobRP4 locus is functional.

Plasmid pDM4A7 was then digested with EcoRI, treated with Pfu Turbo™ DNA polymerase and ligated in order to remove the EcoRI restriction enzyme site to generate plasmid pDM4A7ΔEcoRI. A short HindIII fragment from pDM4 which includes the multiple cloning site was then ligated into pDM4A7ΔEcoRI digested with HindIII. The ligation reaction was transformed into SY327λpir and transformants selected on L-agar supplemented with 20 µg/ml chloramphenicol.

Oligonucleotide R6K-01 hybridises within the short HindIII fragment from pDM4 which includes the multiple cloning site. Therefore, transformants were screened by PCR using oligonucleotides R6K-01 and 4720 in order to identify those harbouring the desired plasmid construct. A number of such transformants were identified, and one of these, called pDM4A7ΔE, was chosen for further manipulation.

Plasmid pDM4A7ΔE carries three EcoRI sites very close together on the short HindIII fragment from pDM4 which includes the multiple cloning site. The two very short EcoRI fragments of pDM4A7ΔE were therefore removed by digestion with EcoRI followed by ligation. This resulted in a pDM4A7ΔE derivative that possess only one EcoRI site which was called pJCB10. The region of pJCB10 that includes oriR6K and the MCS was amplified using oligonucleotides 4715 and 4917 and nucleotide sequence determinations for part of this fragment were performed using oligonucleotide 4917. This presented us with the nucleotide sequence across the MCS which was previously unknown.

The sacB gene was then amplified using Pfu DNA polymerase and oligonucleotides 4722 and 4723. The 1.6 kb product was ligated with the plasmid vector pPCR-Script™ (Stratagene) and transformed into E. coli XL10 Gold™ cells (Stratagene). Transformants were obtained and the functionality of the sacB gene was confirmed by plating the clones onto L-agar and 5% sucrose agar. One construct gave good growth on L-agar, and none on 5% sucrose agar, and so was chosen as the source of the sacB gene. The sacB gene was then digested from this clone using the restriction enzyme PstI, sites for which were incorporated into oligonucleotides 4722 and 4723 for this purpose, and ligated with pJCB10 also digested with PstI. Colonies were checked by PCR using oligonucleotides 4716 and 4766, yielding a product of the expected size (~1700 bp). Again the functionality of the gene was confirmed by plating the clones onto L-agar and 5% sucrose agar. One construct grew on L-agar, but not on 5% sucrose agar. Sequencing of this construct using oligonucleotides 4716 and 4766 respectively indicated the orientation of the sacB gene. This construct was called pJCB12.

Principle of Use of pJCB12

Once a defined genetic construct has been ligated into pJCB12 to give a pJCB12-derivative, the plasmid is transferred into a recipient strain such as an ETEC strain. This may be done according to methods well known in the art, either by conjugation from the pJCB12 host strain SM10λpir, or by transformation of the purified pJCB12-derivative directly into the recipient strain.

Transconjugants or transformants are selected on bacteriological growth medium supplemented with the antibiotic chloramphenicol. Since the suicide vector pJCB12 is unable to replicate in the absence of the pir gene, any transconjugants or transformants that grow will generally have resulted from fusion of the pJCB12-derivative with another replicon by homologous recombination. Using pDM4 and other larger suicide vectors will often result in incorrect targeting, and consequently mutants cannot be isolated in subsequent time-consuming steps.

Figure 4:
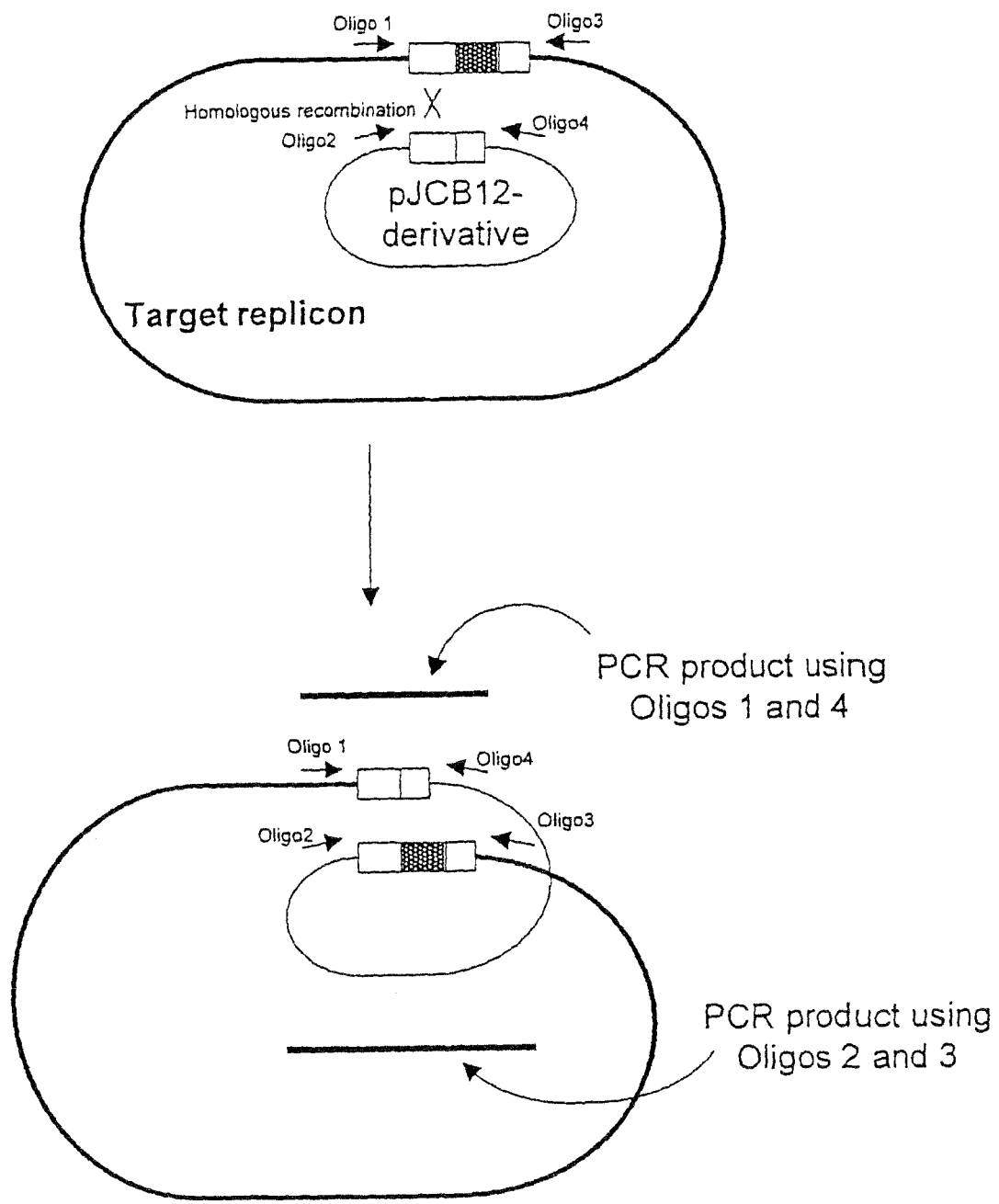
FIG. 4: Diagram of method used to demonstrate correct integration of suicide vector in to targeted locus by linkage PCR.

Although targeting by pJCB12 is much improved over pDM4, incorrect targeting can still occur. Therefore, in order to optimise fully the defined mutation process, a novel approach was taken to screen transformants or transconjugants using PCR to identify those in which the pJCB12-derivative has targeted the desired region of the genome. For this, one oligonucleotide is designed which hybridises within the pJCB12 nucleotide sequences adjacent to the MCS where the defined genetic construct has been inserted. The other oligonucleotide is designed to hybridise to the region of the genome to be targeted, adjacent to but outside of the defined genetic construct. Transformants or transconjugants that are positive using this PCR will have the pJCB12-derivative targeted to the correct region of the genome (see FIG. 4).

Once the correct recombinants have been identified, derivatives need to be isolated in which the pJCB12 vector has been lost. Such derivatives may be selected by supplementing the bacteriological growth medium with 5% sucrose. This sucrose selection may be made more efficient using a modified L-medium in which the NaCl ingredient is absent and supplemented with 5% sucrose. Under these conditions the sacB gene of pJCB12 is toxic, and only derivatives where the sacB gene has been lost will grow. This event again occurs by homologous recombination and has a number of outcomes. Firstly, a reversion event will result in the targeted region remaining as it was. Secondly, homologous recombination may result in the defined genetic construct being swapped with the targeted region resulting in the defined construct being incorporated at the target region. In addition, if the targeted region is part of a plasmid, such as many of the toxin genes of ETEC strains, then two additional events may occur. These are, thirdly, an undefined spontaneous deletion event, resulting in the loss of a part of the targeted region which may extend beyond the boundaries of the defined genetic construct, and, fourthly, the loss of the whole plasmid, an event which may be termed "specific plasmid curing".

Testing of sucrose resistant derivatives by PCR can identify the desired recombinants. For this, oligonucleotides that hybridise at each end of the targeted region and outside of the defined genetic construct are used. If the PCR product is the same size as prior to introduction of the pJCB12-derivative construct, then a reversion event has occurred. If, for example the genetically defined construct is a deletion mutation, then the PCR product should be smaller than previously and of a predictable size. Specific plasmid curing and undefined spontaneous deletion will normally result in no PCR product or non-specific products of unexpected size in this type of PCR reaction.

In summary, vector pJCB12 (or another similar vector of the invention) may be used in a method for producing a bacterial cell in which a target gene (e.g. a toxin gene such as ST, LT or EAST1 or a chromosomal gene such as an omp or aro gene) is deleted, inactivated or replaced, which method comprises transferring the vector into a bacterial cell containing the target gene and selecting for a cell in which the target gene has been deleted, inactivated or replaced. The selection may be carried out using a multi-stage procedure along the following lines:

Selecting for a colony of cells which contains the selectable marker. If the cell into which the vector is transferred is one that does not support replication of the vector from the origin of replication in the vector, selecting for such a colony of cells identifies cells in which the vector has become incorporated into a cellular replicon;

Carrying out PCR to select for a cell in which the vector has correctly targeted to the target gene, wherein one of the primers used in the PCR hybridizes to vector sequence adjacent to the cloning site and the other hybridizes to a site in the cellular DNA adjacent to the target gene. A positive PCR indicates that the vector has targeted to the target gene.

Selecting for a cell from which vector sequence has been lost by growing the cell under conditions which make effective the gene encoding a product that is toxic to the cells when grown under defined conditions. Survival of a cell indicates that vector sequence has been lost. Where the gene encoding the toxic product is sacB, the cell may be grown in medium supplemented with sucrose and from which NaCl is absent; the product of sacB is toxic when the cells are grown in this medium.

Finally, PCR may be carried out using primers which hybridize at positions outside, and adjacent to each end of, the target gene, wherein a PCR product smaller than the product obtained from a wild-type cell indicates a deletion mutation.

Materials and Methods

Bacterial strains used. ETEC strains as described elsewhere in the specification and lab strains of *E. coli*:

| Strain | Reference or Source |
|---|---|
| SY327λpir | Miller and Mekalanos (56) |
| DH5αλpir | P. Barrow, Institute for Animal Health, Compton |
| SM10λpir | Simon et al., 1983 (47) |

Bacteriological growth media. ETEC strains were routinely grown in L-broth and on L-agar and incubated at 37° C. overnight. L-broth consists of 10 g/l peptone, 5 g/l yeast extract and 5 g/l of NaCl dissolved in 1 l of deionsed water. L-agar is L-broth supplemented with 15 g/l agar. Growth medium containing 5% sucrose was as described above, but without the 5 g/l of NaCl. To optimise expression of CFAs ETEC strains were harvested from CFA-agar (1% casamino acids, 2% agar, 0.15% yeast extract, 0.005% $MgSO_4$, 0.0005% $MnCl_2$). Chloramphenicol was used at a concentration of 10 μg/ml, tetracycline at 15 μg/ml and streptomycin at 20 μg/ml.

Bacterial Conjugations were performed by mixing donor and recipient ETEC strains on L-agar and incubating at 37° C. for 3 to 18 h. Bacterial growth was scraped off into L-broth and plated onto L-agar plates supplemented with chloramphenicol and another appropriate antibiotic to select ETEC strains (streptomycin for strain B, tetracycline for other ETEC strains) that had incorporated the pJCB12-derivative.

Identification of correctly targeted recombinants. Transconjugants or transformants obtained by growth on L-agar supplemented with chloramphenicol following introduction of pJCB12-derivative constructs were tested by PCR in order to identify those in which the desired genetic locus had been targeted. For this, one of the oligonucleotides hybridised within the pJCB12 nucleotide sequences adjacent to the multiple cloning site (MCS) where the defined genetic construct had been inserted. The other oligonucleotide hybridised to the genome, adjacent to but outside of the defined genetic construct. In such a PCR, the generation of a fragment indicated that the binding sites for the respective oligonucleotides had become linked, which could occur only if the pJCB12-derivative had targeted the correct region of the genome.

Excision of pJCB12 from transconjugants by growth in the presence of 5% sucrose. Transconjugants or transformants having the pJCB12-derivative targeted to the correct region of the genome were then streaked onto fresh L-agar supplemented with chloramphenicol and another appropriate antibiotic to select ETEC strains (see above), and incubated at 37° C. to allow colonies to grow. L-broth cultures inoculated from these fresh plates were then grown. Cells from these cultures were harvested, resuspended in 5% sucrose broth, and incubated overnight prior to plating serial dilutions on 5% sucrose agar in order to select recombinants in which the pJCB12-derivative had excised. The inoculated sucrose agar plates were then incubated overnight and the resulting colonies tested by PCR using relevant oligonucleotides in order to identify mutants.

DNA manipulations were performed using standard procedures (25). Plasmid DNA was prepared using plasmid purification kits from QIAGEN (Crawley, UK) and DNA fragments were isolated from agarose gels using the QIAquick™ gel extraction kit from QIAGEN.

PCR reactions were performed routinely using Taq DNA polymerase (Life Technologies); when high fidelity PCR was required, such as in the construction of pJCB12, Pfu "Turbo" DNA polymerase (Stratagene) was used. Both DNA polymerases were used in accordance with the suppliers instructions. Routinely, the following PCR cycle was used:
Step 1; 95° C., 50 sec
Step 2; 95° C., 10 sec
Step 3; 55° C., 1 min
Step 4; 72° C., 1 min
Step 5; repeat steps 2 to 4 twenty-five times
Step 6; 72° C., 1 min For construction of pJCB12, a pDM4 plasmid DNA preparation was used as the template in PCR reactions. For routine PCR screening a pick from a bacterial colony was used as the template. For construction of toxin deletion mutants, plasmid DNA preparations extracted from suitable ETEC strains were used. Plasmid pJCB12 and DNA fragments incorporating deletion mutations were generated using a modification of overlap extension PCR (31). In the modified version, there is no overlap in the fragments amplified. Instead, the fragments flank the region to be deleted, and the complementary sequences which allow joining of the two fragments are included in the 5'-ends of the relevant oligonucleotides; see FIG. 3.

SDS-PAGE

This was performed essentially as described by Laemmli (16) and was used for visualisation of expressed CFAs and for checking LPS profiles. For LPS profiles, cells were grown overnight in L-broth, harvested and resuspended in water so as to give a cell suspension with an A600 of 20/cm. The cell suspension was mixed with an equal volume of 50 mM Tris HCl pH6.8, 2% (w/v) SDS, 10% (v/v) glycerol, 0.25% (w/v) bromophenol blue, 2% (v/v) 2-mercaptoethanol and boiled for 5 minutes. Proteinase K was then added to a final concentration of 0.2 mg/ml and the samples incubated at 60° C. for 1 h before loading 5 to 10 µl onto SDS-PAGE gels. For CFAs, bacteria were harvested from CFA-agar and resuspended in water so as to give a cell suspension with an A600 of 20/cm. The cell suspension was heated to 65° C. for 10 mins, the samples were then centrifuged to remove whole cells. An equal volume of 50 mM Tris HCl pH6.8, 2% (w/v) SDS, 10% (v/v) glycerol, 0.25% (w/v) bromophenol blue, 2% (v/v) 2-mercaptoethanol was then added. Volumes of 3 to 10 µl were then loaded onto 12% Tris-glycine SDS-PAGE gels (Invitrogen). CFAs were visualised by Coomassie blue staining (Sambrook et al 1989, ref 25) while LPS was visualised using a SilverXpress™ silver stain kit (Invitrogen).

EXAMPLE 2

Removal of Toxin Genes and Introduction of Attenuating Mutations into Strains Expressing CFA/I Manipulation of Strain A to Produce Strain ACAM 2010

Strain A (WS-1858B) expresses the colonisation factor antigen CFA/I and the heat-stable toxin ST. In order to generate an ST-negative derivative that continues to express the CFA/I colonisation factors the strain was first transformed with a plasmid conferring tetracycline resistance. This was to allow subsequent selection of the strain from conjugation mixtures. The plasmid conferring tetracycline resistance is a derivative of plasmid pACYC184 (40) in which the chloramphenicol resistance determinant had been inactivated by deletion of a BsmBI restriction enzyme fragment using standard DNA manipulation procedures. This plasmid was termed "pACYC-Tc" and was introduced into strain A by electro-transformation.

The TetR derivative of Strain A was conjugated with SM10λpir harbouring plasmid pJCB12-STI. This pJCB12 derivative contains a fragment of the STI gene amplified from strain B using oligonucleotides 4764 and 4765 cloned into the MCS. The sequence of this construct is given in FIG. 5. Note that the STI fragment in this derivative is not a deletion; the aim is to target the locus with the markers encoded by pJCB12 in order to allow selection for deletion events resulting in the correct outcome.

Transconjugants were selected by plating the mixture on L-agar supplemented with tetracycline and chloramphenicol and the colonies obtained were confirmed as transconjugants by PCR testing using oligonucleotides 4720 and 4721 which amplifies the chloramphenicol resistance determinant. Three transconjugants were identified and called A13, A14 and A18 respectively. Each transconjugant was grown on 5% sucrose medium and colonies obtained were screened for ST using oligonucleotides 4764 and 4765. One of the ST-negative derivatives identified was called A18-34 and was tested by PCR for the presence of the cfaB gene using oligonucleotides BglIIFOR and BglmodREV, for the presence of the cfaC gene using oligonucleotides 4727 and 4728, and for the presence of the cfaR gene using oligonucleotides 4785 and 4786. All three of these PCR reactions were positive, confirming the presence of the relevant genes. Derivative strain A18-34 was then grown on CFA-agar and processed for SDS-PAGE in order to visualise CFA/I expression. This confirmed that Strain A18-34 expressed CFA/I and, therefore, that an ST-negative, CFA/I expressing strain had been isolated.

In the next step an ampicillin sensitive derivative of strain A18-34 was identified. For this, strain A18-34 was grown in LB-broth through three passages. The resulting culture was then diluted and plated onto LB-agar. When small colonies were visible they were replica-plated onto LB-agar supplemented with ampicillin at 200 µg/ml and then incubated to allow colonies to grow. One colony was identified that was absent from the ampicillin supplemented replica plate and subsequently confirmed as being ampicillin sensitive. This strain was called A18-34 Ap$^S$.

In the next step, a trimethoprim sensitive derivative of strain A18-34 Ap$^S$ was isolated. For this strain A18-34 Ap$^S$ was replica plated as described above but onto LB-agar and M9 minimal salts agar supplemented with 0.4% glucose and trimethoprim at 25 μg/ml. Two colonies were identified that had not grown on the trimethoprim supplemented replica plates, and one of these which was called A18-34 $Ap^S Tp^S$ was chosen for further manipulations.

The EAST1 toxin gene was then deleted from the strain A18-34 $Ap^S Tp^S$. For this, conjugations were performed with SM10λpir harbouring a pJCB12 plasmid derivative carrying a defined EAST1 deletion as the donor strain and strain A18-34 $Ap^S Tp^S$ as the recipient strain. Transconjugants were selected on L-agar supplemented with tetracycline at 15 μg/ml and chloramphenicol at 10 μg/ml. One transconjugant was identified by PCR using oligonucleotides 4917 and 4778 in which the pJCB12-derivative was inserted at the correct location. This tetracycline and chloramphenicol resistant transconjugant was then grown in 5% sucrose medium in order to select recombinants in which the pJCB12-derivative had excised (as described in Materials and Methods). Colonies that grew on L-agar supplemented with 5% sucrose were then tested by PCR using oligonucleotides 4749 and 4752. Three isolates were identified that were negative in this PCR reaction indicating that the EAST1 locus had been lost.

Defined deletion mutations were then introduced into the aroC, ompC and ompF genes in order to further attenuate the A18-34 $Ap^S Tp^S$ ΔEAST1 derivative as described in other Examples. Initial attempts to introduce the ΔaroC mutation met with little success as was the case when constructing a strain J-derivative aroC deletion mutation (see below). Therefore, attempts were made to introduce the ΔaroC$^J$ mutation (see below for details of the mutation). Following transfer of pJCB12-ΔaroC$^J$ into the A18-34 $Ap^S Tp^S$ ΔEAST1 derivative a transconjugant was identified by PCR using oligonucleotides 4917 and 4742. This transconjugant was then grown in 5% sucrose medium in order to select recombinants in which the pJCB12-derivative had excised (as described in Materials and Methods). Colonies that grew on L-agar supplemented with 5% sucrose were then tested by PCR using oligonucleotides 47116 and 47117, and a derivative that carried the ΔaroC$^J$ defined deletion mutation was identified. Aromatic amino acid auxotrophy was demonstrated in this A18-34 $Ap^S Tp^S$ ΔEAST1 ΔaroC$^J$ strain by streaking on minimal agar and minimal agar supplemented with "aro mix." The strain grew only on the aro mix supplemented agar, whereas the parental strain A18-34 $Ap^S Tp^S$ ΔEAST1 grew both in the presence and absence of "aro mix."

Next the ΔompC defined deletion mutation was introduced into the A18-34 $Ap^S Tp^S$ ΔEAST1 ΔaroC$^J$-derivative as described for strain H (Example 4) and a ΔompC deletion mutant was identified. Expression of CFA/I and LPS by this A18-34 $Ap^S Tp^S$ ΔEAST1 ΔaroC$^J$ ΔompC strain was confirmed by SDS-PAGE.

Next the ΔompF defined deletion mutation was introduced into the A18-34 $Ap^S Tp^S$ ΔEAST1 ΔaroC$^J$ ΔompC-derivative as described for strain H (Example 4) and a ΔompF deletion mutant was identified. Expression of CFA/I and LPS by this A18-34 $Ap^S Tp^S$ ΔEAST1 ΔaroC$^J$ ΔompC ΔompF strain was confirmed by SDS-PAGE.

Finally, the pACYC-Tc plasmid that was introduced into strain A to confer tetracycline resistance was specifically cured from the A18-34 $Ap^S Tp^S$ ΔEAST1 ΔaroC$^J$ ΔompC ΔompF strain. For this the plasmid pJCB12-pACYCori described in Example 4 was introduced by electrotransformation. Transformants harbouring pJCB12-pACYCori were selected by growth on L-agar supplemented with chloramphenicol. One transformant was then grown in 5% sucrose medium in order to select derivatives from which the pJCB12-pACYCori plasmid had been cured (as described in Materials and Methods). Colonies that grew on L-agar supplemented with 5% sucrose were then picked onto L-agar medium supplemented with chloramphenicol and onto L-agar medium supplemented with tetracyclin. This identified a number of derivatives which were sensitive to both these antibiotics, confirming that the pJCB12-pACYCori plasmid had indeed specifically cured the strain of the pACYC-Tc marker plasmid and then itself been cured by growth in the presence of sucrose.

One of these antibiotic sensitive derivatives was chosen and tested by PCR for the presence of the cfaA, cfaC, and cfaD genes using oligonucleotide pairs 47104 with 47105, 4729 with 4730, and 4785 with 4786 respectively. In addition, the presence of the ΔaroC$^J$, ΔompC and ΔompF deletion mutations was confirmed using the oligonucleotide pairs 47116 with 47117, 4732 with 4743, and 4733 with TT1. Expression of CFA/I and LPS was confirmed in this strain using SDS-PAGE and the nucleotide sequence across the ΔaroC$^J$, ΔompC and ΔompF mutations was confirmed.

Manipulation of Strain B to Produce Strain ACAM 2011

Strain B (WS-4437A) expresses the colonisation factor antigen CFA/I and the heat-stable toxin ST. Initially, isolation of a spontaneous ST-deletion mutation was attempted by targeting ST using plasmid pJCB12-STI. This plasmid was introduced into Strain B by conjugation from SM10λpir and transconjugants were obtained by growth on L-agar supplemented with chloramphenicol. After several attempts, a number of ST-negative mutants were identified, but these were all negative for CFA/I.

Figure 20:
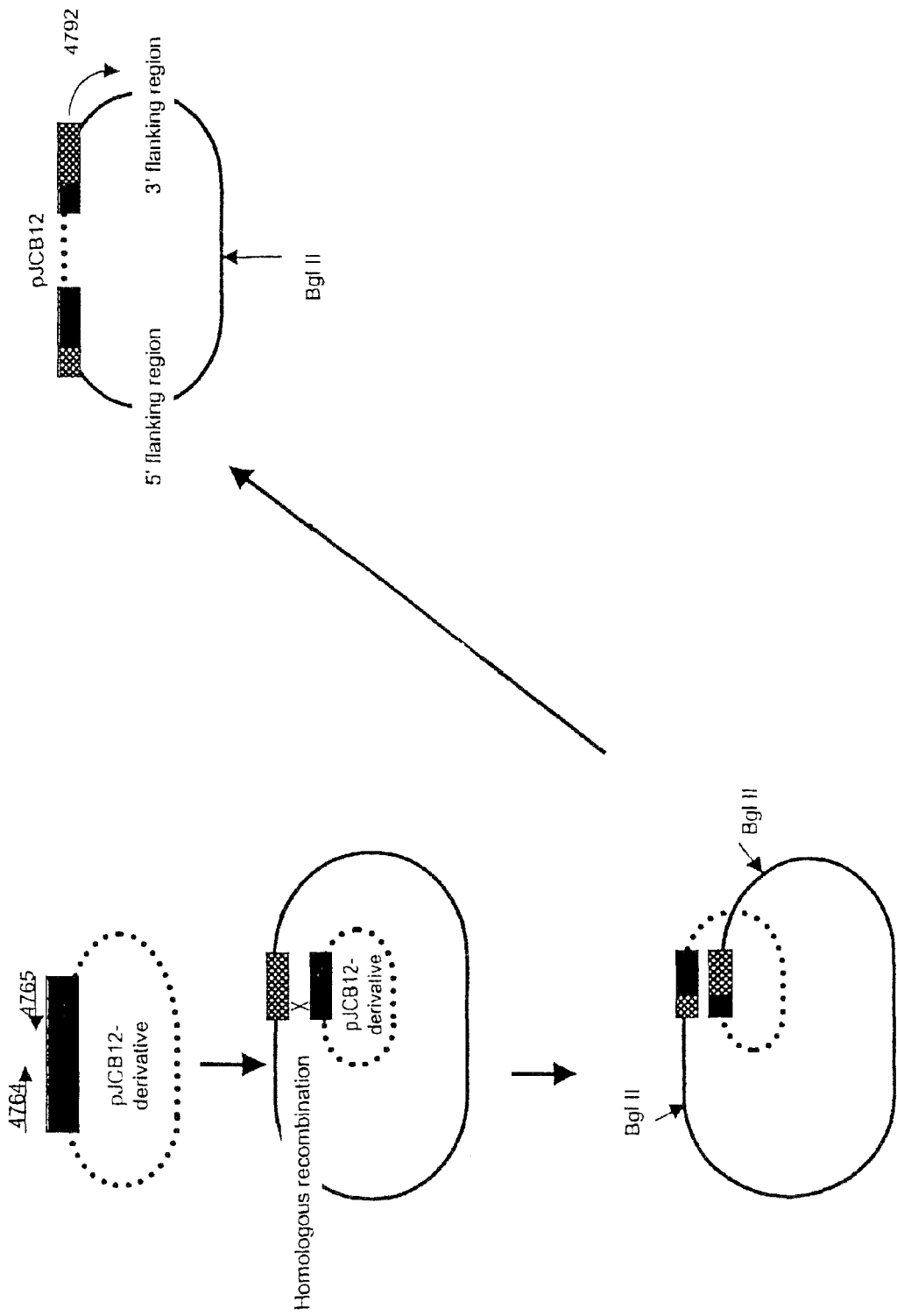

It was therefore decided to construct a defined STI deletion mutation specific for Strain B. The first requirement was to determine nucleotide sequence flanking the 3' end of the ST gene. The process used to do this is illustrated in FIG. 20. Plasmid DNA was isolated from a transconjugant strain in which pJCB12-STI was targeted to the ST gene. Purified DNA was subjected to restriction endonuclease digestion with BglII which cuts the ETEC plasmid but not the ST gene or the pJCB12 construct. Digested DNA was ligated and electrotransformed into SY327λpir and transformants were selected on L-agar supplemented with chloramphenicol. This process is termed "plasmid rescue" and results in the re-isolation of the pJCB12 replicon incorporating a large fragment of DNA that includes the whole of the STI region and a large amount of flanking DNA. The sequence of the flanking DNA was obtained. Nucleotide sequence data obtained from this then allowed further oligonucleotides (4797 and 4798) to be designed and used to determine additional nucleotide sequence further downstream of the STI gene in Strain B. FIG. 5 shows the determined sequence and the location of all oligonucleotide binding sites.

Using the determined nucleotide sequence, an ST-deletion mutation was constructed. This was done by amplifying two fragments from the STI locus using oligonucleotides 47101 with 47114, and 47115 with 47100. The two resulting fragments were then joined by overlap extension PCR using oligonucleotides 47100 and 47101 and ligated into the MCS of pJCB12 using standard techniques.

The construct was introduced into strain B by conjugation from SM10λpir and chloramphenicol resistant transconjugants in which ST had been correctly targeted were identified by PCR using oligonucleotides 4917 and 4799. These transconjugants were grown in the presence of sucrose and colonies obtained were then screened using oligonucleotides 47100 and 47101 in order to identify ST deletion mutants. One derivative was found which was negative using these oligonucleotides, suggesting that a spontaneous deletion had resulted in loss of the entire ST locus. This derivative was positive by PCR using oligonucleotides 4727 with 4728 which amplify part of the cfaC gene. It was also positive using oligonucleotides BglIIFOR and BglmodREV which amplify the cfaA gene, and using oligonucleotides 4785 and 4786 which amplify the CFA/I regulator gene, cfaD. Functional assay for ST confirmed that this derivative was ST-negative, while SDS-PAGE confirmed that it continued to express CFA/I.

Defined deletions were then introduced into the aroC, ompC and ompF genes in order to attenuate the Strain B ST-negative derivative. Initial attempts to introduce the ΔaroC deletion were unsuccessful. Therefore the ΔaroC$^J$ deletion was used (see below for details of the mutation). Following transfer of the pJCB12ΔaroC$^J$ deletion into Strain B ST-negative derivative, transconjugants were identified by PCR using oligonucleotides 4917 with 4742. A transconjugant was identified and then grown in 5% sucrose medium in order to select recombinants in which the pJCB12 derivative had been excised (as described in materials and methods). Colonies that grew on L-agar supplemented with 5% sucrose were then tested by PCR using oligonucleotides 47116 with 47117 and a derivative that carried the ΔaroC$^J$ deletion was identified. The CFA/I status of the exconjugant was checked by PCR using oligonucleotides 4727 with 4728 for cfaC, 4785 with 4786 for cfaD and BglIIFOR with BglIImodREV for cfaA.

The ΔompC defined deletion mutation was then introduced into the Strain B ST-negative ΔaroC$^J$ derivative as described for strain H (Example 4) and a ΔompC deletion mutant identified. The CFA/II status of the exconjugant was checked by PCR using oligonucleotides 4727 with 4728 for cfaC, 4785 with 4786 for cfaD and BglIIFOR with BglIImodREV for cfaA.

The ΔompF defined deletion mutation was introduced into the Strain B ST-negative ΔaroC$^J$ ΔompF ΔompC derivative as described for strain H (Example 4) and an ompF deletion mutant identified. The CFA/I status of the exconjugant was checked by PCR using oligonucleotides 4727 with 4728 for cfaC, 4785 with 4786 for cfaD and BglIIFOR with BglIImodREV for cfaA.

Finally the pStrep plasmid, that confers streptomycin resistance, was specifically cured from the Strain B ST-negative ΔaroC$^J$ ΔompF ΔompC derivative. For this a plasmid derivative of pJCB12 was constructed which incorporated the pStrep replication origin. This was done by shotgun cloning pStrep fragments generated by restriction endonuclease digestion with SphI into the SphI site of pJCB12, and transforming the DNA into XL-10 Gold ultracompetent *E. coli* cells (Stratagene). Transformants were plated on L-agar supplemented with chloramphenicol. Because pJCB12 is a suicide vector requiring special host strains that carry the pir gene, transformants that grew in the presence of chloramphenicol were assumed to be derivatives of pJCB12 which carried the pStrep replication origin. Plasmid DNA from four such transformants showed that in each case an SphI DNA fragment of approximately 2 kb had been cloned into pJCB12. This pJCB12-derivative was called pJCB12-pStrep-ORI The pJCB12-pStrep-ORI plasmid was introduced into the Strain B ST-negative ΔaroC$^J$ ΔompF ΔompC derivative by conjugation from strain SM10λpir, and the resulting transconjugants selected by growth on agar medium supplemented with chloramphenicol. Colonies which grew were used to inoculate broth supplemented with chloramphenicol and, following incubation to allow growth, dilutions of this culture were plated on agar supplemented with chloramphenicol. Colonies which grew on this medium were picked onto agar supplemented with streptomycin in order to identify those from which the pStrep plasmid had been lost. One of these streptomycin sensitive colonies was then grown in L-broth supplemented with 5% sucrose in order to select for a derivative from which the pJCB12-pStrep-ORI plasmid had been lost. Dilutions from this broth culture were plated on L-agar supplemented with 5% sucrose and after incubation some of the resulting colonies were picked onto agar supplemented with chloramphenicol in order to identify those from which the pJCB12-pStrep-ORI plasmid had been lost.

The CFA/I status of the exconjugant was again checked by PCR using oligonucleotides 4727 with 4728 for cfaC, 4785 with 4786 for cfaD and BglIIFOR with BglIImodREV for cfaA. CFA/I protein expression was then checked by SDS-PAGE and Western blotting. The LPS profile was also checked. In addition the ΔaroC$^J$, ΔompC and ΔompF mutations were confirmed by sequencing, and the aromatic amino acid dependence of the strain was also confirmed.

EXAMPLE 3

A Derivative of a Virulent Wild-Type ETEC Strain which Expresses CS5, CS6, LT, ST and EAST1 wherein the LT, ST and EAST1 Genes Have Been Deleted Strain E expresses CS5, CS6 and the toxins EAST1, ST and LT. In order to facilitate genetic manipulation plasmid pACYC-Tc (described in Example 2 above) was introduced into strain E by electro-transformation in order to confer tetracycline resistance.

The EAST1 toxin gene was deleted from Strain E first. This required the construction of a pJCB12 derivative which carries a defined EAST1 deletion mutation. Such a deletion mutation was generated by amplifying EAST1 fragments from the ETEC strain H10407, using oligonucleotides 4749 with 4750, and 4751 with 4752, to generate two DNA fragments flanking the EAST1 gene. FIG. 6 shows the sequence of the EAST1 locus derived from IS1414 (Genbank accession number AF143819) and all oligonucleotides used. These were then fused by an additional overlap extension PCR reaction using primers 4749 and 4752 and the resulting fragment was cloned into pJCB12 using the SalI and SphI restriction sites. Thus, a pJCB12 derivative had been constructed which incorporated this deletion mutation.

Strain SM10λpir harbouring pJCB12-ΔEAST1 was conjugated with Strain E and transconjugants selected. Colonies that grew on L-agar supplemented with chloramphenicol and tetracycline were screened using the oligonucleotides 4917 and 4753 (equivalent to oligos 4 and 1 in FIG. 4). Two transconjugants were obtained which were positive in both this PCR reaction indicating that the pJCB12-ΔEAST1 plasmid had correctly targeted the EAST1 gene.

These chloramphenicol resistant transconjugants were then grown in 5% sucrose medium in order to select recombinants in which the pJCB12-derivative had excised. Four exconjugants were obtained on the sucrose agar, and these were negative when tested for the presence of the EAST1 gene by PCR using oligonucleotides 4749 and 4752, indicating that the whole of the EAST1 region had been lost in this derivative. The strain E EAST1-negative derivative was then tested by PCR using oligonucleotides 4738 with 4780 which are specific for the CS5 operon, and oligonucleotides 4740 with 4781 which are specific for the CS6 operon. These PCR reactions were positive for all four exconjugants confirming that they continued to harbour the CS5 and CS6 genes.

Next, an LT-deletion mutant of the Strain E EAST1-negative derivative was constructed. For this a pJCB12 derivative plasmid was constructed that carried a defined deletion of the LT-A gene in the LT locus. See FIG. 7.

A defined LT-A deletion was constructed by PCR amplification using oligonucleotides 4772 with 4773, and 4774 with 4746, to generate two DNA fragments flanking the LT-A gene. These were then fused by an additional overlap extension PCR reaction and the resulting fragment was cloned into pJCB12 using the SalI and SphI restriction sites.

The pJCB12-ΔLT-A construct was introduced into the Strain E ΔEAST1 derivative by conjugation from the pJCB12 host strain SM10λpir and transconjugants were selected on L-agar supplemented with chloramphenicol and tetracycline. Resulting colonies were screened by PCR using oligonucleotides 4762 and R6K-01 which identified two transconjugants in which the LT locus had been correctly targeted.

These chloramphenicol resistant transconjugants were then grown in 5% sucrose medium in order to select recombinants in which the pJCB12-derivative had been excised. Colonies that grew on the sucrose agar were tested by PCR using oligonucleotides 4762 and 4746 in order to identify LT-A deletion mutants. Three derivatives were identified which were negative in this PCR reaction, suggesting that they had lost the entire LT locus. PCR reactions performed on these three LT-negative derivatives using oligonucleotides 4738 with 4780, and oligonucleotides 4740 with 4781 confirmed the presence of the CS5 and CS6 genes respectively.

Next, the ST gene was deleted from this Strain E EAST1-negative LT-negative derivative. For this, plasmid pJCB12-STI (as described in Example 2) was transferred into Strain E from SM10λpir and transconjugant selected on L-agar supplemented with chloramphenicol. A transconjugant was identified by PCR using oligonucleotides 4917 and 4794, and this transconjugant was then grown in 5% sucrose medium to select for derivatives from which the pJCB12-STI had been lost. Of 133 colonies screened, only 3 had lost STI, the others being revertants, and all of these 3 STI-negative derivatives were negative also for CS5 and CS6. These results suggested that the STI locus was present on the same plasmid as the CS5 and CS6 genes (as did Southern hybridization data) and that the STI locus was relatively stable, so that revertants or derivatives were obtained in which only specific plasmid curing had occurred.

It was therefore decided that a defined STI-deletion mutation specific for strain E was needed. In order to make this construct additional nucleotide sequence data was required for the region downstream of the STI gene in Strain E. Therefore, one of the pJCB12-ST transconjugants was used for sequence determinations at the STI locus using the plasmid rescue procedure described in Example 2 and illustrated in FIG. 20. A pJCB12-derivative was obtained that incorporates a large fragment of DNA that includes the ST-I gene and a large amount of flanking DNA from Strain E. This plasmid preparation was used as template in nucleotide sequence determination reactions using oligonucleotide 4764 to determine sequence through the STI gene, and oligonucleotide 4792 to determine sequence downstream of the STI gene. The new sequence data allowed an additional oligonucleotide, 47106, to be designed which was used in further nucleotide sequence determinations. This additional new sequence data enabled oligonucleotides 47112, 47120 and 47121 to be designed for construction of the deletion cassette. The sequence of the ST-1 gene and flanking regions showing the binding sites of all oligonucleotides used is given in FIG. 8.

As with other deletion mutations, two DNA fragments from the ST region were amplified by PCR using oligonucleotides 4764 with 47120, and 47121 with 47112, and the two fragments generated were fused by an additional overlap extension PCR reaction using oligonucleotides 4764 and 47112. The resulting fragment was cloned into pJCB12 using the SacI and SalI restriction endonuclease sites of pJCB12 and those incorporated into oligonucleotides 4764 and 47112 respectively.

The resulting recombinant plasmid pJBC12-ΔSTI$^E$ was introduced into the Strain E EAST1-negative LT-negative derivative from strain SM10λpir. The resulting chloramphenicol and tetracycline resistant transconjugants were screened by PCR using oligonucleotides 4917 with 4794, and R6K-01 with 47113. Two transconjugants were identified that were positive, indicating that the STI gene had been correctly targeted.

Figure 9:
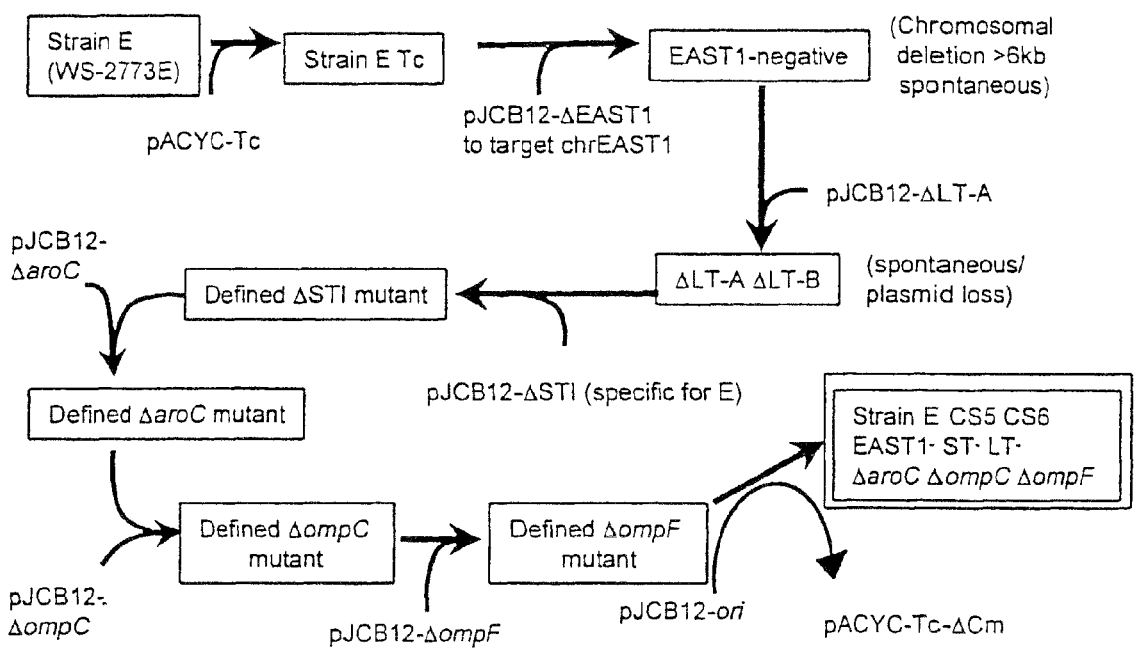
FIG. 9: Diagram of the individual stages involved in the attenuation of strain E.

These chloramphenicol resistant transconjugants were then grown in medium supplemented with sucrose, followed by plating on 5% sucrose agar to obtain excision of the pJCB12 derivative. The colonies that grew on sucrose agar were screened using oligonucleotides 4764 with 47112 and a number were identified that were negative, and three colonies were identified that showed the presence of the STI deletion mutation. PCR reactions performed on the STI deletion mutants using oligonucleotides 4738 with 4739 to detect CS5, 4740 and 4741 to detect CS6 and 4783 with 4784 to detect the CS5 regulator gene were all positive, indicating that these genes had been retained in these defined STI-deletion mutants. Additional attenuating mutations in aroC, ompC and ompF were introduced as described (ref 32 and Example 4). See FIG. 9.

EXAMPLE 4

Removal of Toxin Genes and Introduction of Attenuating Mutations into Strains Expressing CS2/CS3 (Strain H) and CS4/CS6 (Strain J)

Strain H Manipulation

Strain H expresses CS2 and CS3 and the toxins EAST and ST. It also has the genes for LT, but LT protein has not been detected by in vitro assays. In order to facilitate genetic manipulation the plasmid pACYC-Tc (described in Example 2) was introduced into Strain H by electro-transformation in order to confer tetracycline resistance.

The EAST1 toxin gene was the first to be deleted from Strain H. Strain SM10λpir containing the pJCB12-ΔEAST1 plasmid described in Example 3 was conjugated with Strain H and transconjugants selected on L-agar containing chloramphenicol and tetracycline. Transconjugant colonies in which the EAST1 gene had been correctly targeted were identified by PCR using the oligonucleotides 4917 and 4753. Transconjugants were then processed in order to select derivatives in which the pJCB12-derivative had excised (described above). Colonies that grew on 5% sucrose agar were tested by PCR using the oligonucleotides 4775 and 4777 and a number were identified that were negative by PCR indicating that the whole of the EAST1 region had been lost. These Strain H EAST1-negative derivatives were then tested for the presence of a transcriptional activator for colonization factors, rns, by PCR using the oligonucleotides RNS-03 and RNS-04. Two of the Strain H EAST1-negative mutants were positive for rns. Further testing by PCR for CS2 using oligonucleotides 4712 and 4779, and CS3 using oligonucleotides CS3-02 and CS3-03 indicated that the mutants were both CS2 and CS3 positive. Testing by PCR for the LT locus using oligonucleotides LT-04 and LT-05, and for the STI locus using oligonucleotides EST-01 and 4765 showed that the mutants were negative for these toxins, indicating that the ST and LT loci had been lost concomitantly with EAST1. The expression of CS2 and CS3 in the Strain H toxin-negative mutants was confirmed by SDS-PAGE.

Defined deletion mutations were then introduced into the aroC, ompC, and ompF genes in order to further attenuate the Strain H toxin-negative derivative using a method similar to that described previously (32). However, this earlier description for introducing these mutations used the suicide vector pCVD442 described in Example 1. This suicide vector codes for ampicillin resistance, which is not optimal for selecting infrequent transconjugant from a large mixed bacterial population. In addition, at this stage, the Strain H toxin-negative derivative continues to express it's own ampicillin resistance, making pCVD442 useless with this strain. Therefore, the ΔaroC, ΔompC and ΔompF deletion mutations previously cloned into pCVD442 (32) were sub-cloned into pJCB12. For this, the ΔaroC mutation was sub-cloned using the restriction endonuclease sites XbaI and SacI, ΔompC used SacI and SalI sites, and ΔompF used SacI and SphI sites. The pJCB12-derivatives were then transformed into strain SM10λpir.

The defined ΔaroC mutation was the first to be introduced into the Strain H toxin-derivative from strain SM10λpir. Transconjugant colonies that grew on L-agar supplemented with chloramphenicol and tetracycline were screened by PCR using the oligonucleotides 4917 and 4742 in order to identify those in which the aroC locus had been correctly targeted. These transconjugant colonies were then streaked onto fresh L-agar supplemented with chloramphenicol and tetracycline. Following incubation, the colonies that grew were tested for the presence rns by PCR using the oligonucleotide primers RNS-03 and RNS-04 and for CS2 using primers 4712 and 4779. The reactions confirmed that the transconjugants were positive for both these loci. Transconjugants were then processed in order to select derivatives in which the pJCB12-derivative had excised (as described in previous Examples). Colonies that grew on 5% sucrose agar were tested by PCR using the oligonucleotide primers 4731 and TT20 in order to identify derivatives that harboured the defined ΔaroC deletion mutation. One defined ΔaroC deletion mutant was identified and again checked by PCR to confirm the presence of rns and CS2, as described above. Expression of CS2 and CS3 by this defined ΔaroC deletion mutant was confirmed using SDS-PAGE, and its LPS was checked using SDS-PAGE.

Next the ompC defined deletion mutation was introduced into this Strain H toxin-negative ΔaroC derivative by conjugation from strain SM10λpir harbouring pJCB12-ΔompC. Transconjugant colonies that grew on L-agar supplemented with chloramphenicol and tetracycline were screened by PCR using the oligonucleotides 4917 and 4743 in order to identify those in which the ompC locus had been correctly targeted. Transconjugants were then processed in order to select derivatives in which the pJCB12-derivative had excised (as described above). Colonies that grew on 5% sucrose agar were tested by PCR using the oligonucleotide primers 4732 and 4743 in order to identify derivatives that harboured the defined ΔompC deletion mutation.

The defined ompF mutation was then introduced into this Strain H toxin-negative ΔaroC ΔompC derivative in a similar fashion to that described for the ompC mutation above, except that transconjugant colonies were screened by PCR using the oligonucleotides R6K-01 and 4733 in order to identify those in which the ompF locus had been correctly targeted. Colonies that grew on 5% sucrose agar were tested by PCR using the oligonucleotides 4733 and TT1 in order to identify derivatives that harboured the defined ΔompF deletion mutation.

All of the defined deletion mutations of the Strain H toxin-negative ΔaroC ΔompC ΔompF derivative were then checked by PCR for comparison with the wild-type Strain H. For this the oligonucleotides used for aroC were 4731 and TT20, for ompC were 4732 and 4743, and for ompF were 4733 and TT1. The PCR products generated by these reactions were used for nucleotide sequence determinations across the deletion mutations. The oligonucleotides used for the nucleotide sequence determination reactions were TT35, TT38 and TT33 for aroC, ompC and ompF respectively. All the deletion mutations had the expected nucleotide sequence. The mutant was also checked by PCR for the presence of rns and CS2, and for the absence of the toxin loci, as described above. The presence of the CS3 locus was also confirmed by PCR using the oligonucleotides CS3-03 and CS3-06. Expression of CS2 and CS3 was confirmed using SDS-PAGE, and the LPS was checked using SDS-PAGE.

The ampicillin resistance determinant was then removed from the Strain H toxin-negative ΔaroC, ΔompC, ΔompF derivative. For this the derivative strain was grown through three passages in L-broth and then dilutions plated on L-agar in order to obtain well-separated colonies. The colonies' were then replica plated onto L-agar supplemented with ampicillin at 100 µg/ml. After incubation to allow the colonies to re-grow, the L-agar plates were examined in order to identify any colonies present on the L-agar that did not grow on the ampicillin supplemented L-agar. One such colony was identified and used in further experiments.

Finally, the pACYC-Tc plasmid that was introduced into Strain H to confer chloramphenicol resistance was specifically cured from the Strain H toxin-negative ΔaroC, ΔompC, ΔompF derivative. This required the construction of the plasmid pJCB12-pACYCori. For this the pACYC-Tc origin of replication was amplified by PCR using the oligonucleotides 4760 and 4761 and cloned into pJCB12 using the restriction endonuclease sites SacI and SalI. Strain SM10λpir containing pJCB12-pACYCori was conjugated with the Strain H toxin-negative-ΔaroC, ΔompC, ΔompF derivative, and transconjugants were selected on L-agar containing chloramphenicol. It was hoped that by introducing a second plasmid carrying the same pACYC184 replication origin and selecting for its maintenance, the first pACYC-Tc plasmid would be rendered unstable and in the absence of any selection for its maintenance would be more frequently lost spontaneously. Chloramphenicol resistant transconjugant colonies harbouring the pJCB12-pACYCori plasmid derivative were picked onto L-agar supplemented with tetracycline and one of these colonies was found to be tetracycline sensitive, indicating that the pACYC-Tc plasmid had been lost. This tetracycline sensitive, chloramphenicol resistant colony was then grown on 5% sucrose medium in order to select for derivatives from which the pJCB12-pACYCori had been lost spontaneously. Colonies that grew on 5% sucrose agar were picked onto L-agar supplemented with chloramphenicol to confirm that the pJCB12-pACYCori plasmid had indeed been lost.

Figure 10:
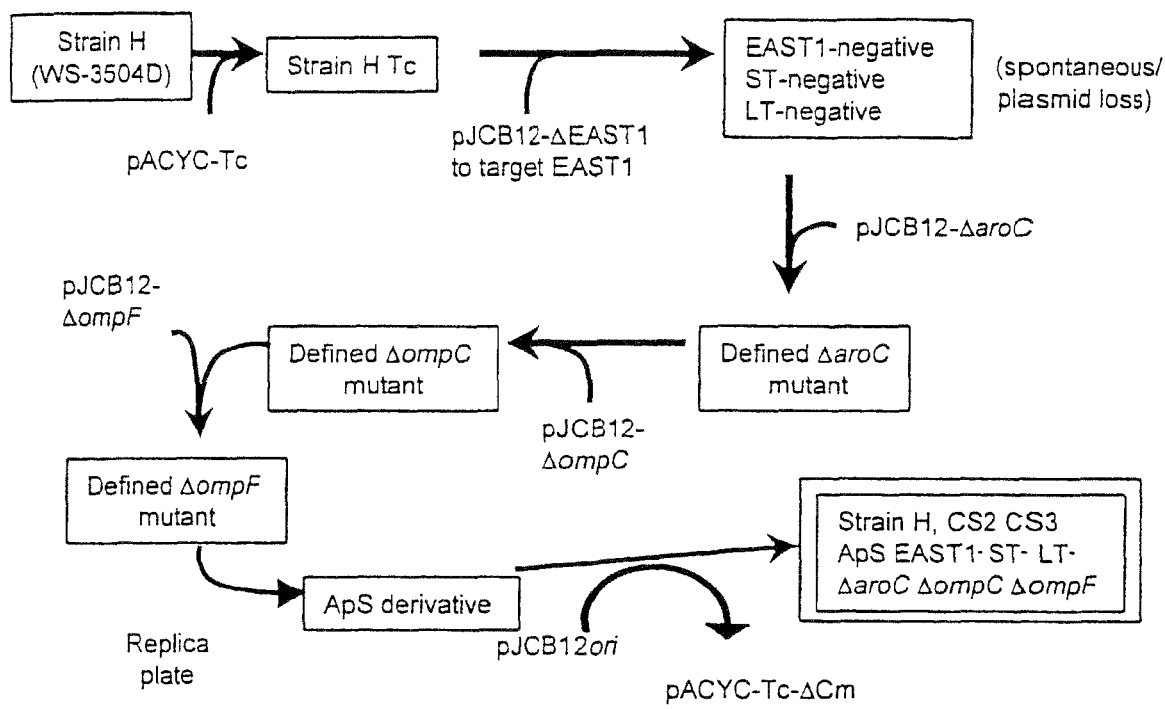
FIG. 10: Diagram of the individual stages involved in the attenuation of strain H.

These manipulations are shown schematically in FIG. 10.

Strain J Manipulation

Strain J expresses CS4 and CS6 and the toxins EAST and ST. It also has the genes for LT, but LT protein has not been detected by in vitro assays. In order to facilitate genetic manipulation the plasmid pACYC-Tc (described in Example 2) was introduced into strain J by electro-transformation thus conferring tetracycline resistance.

The EAST1 toxin gene was deleted from strain J first. Strain SM10λpir containing pJCB12-ΔEAST1 was conjugated with Strain J and transconjugants selected on L-agar containing chloramphenicol and tetracycline. Colonies that grew were screened by PCR using the oligonucleotides 4917 and 4753 in order to identify those in which the EAST1 gene had been correctly targeted. These transconjugant colonies were then streaked onto fresh L-agar supplemented with chloramphenicol and tetracycline and incubated to allow colonies to grow. These colonies were tested by PCR to confirm the continued presence of the CS4 operon using the oligonuncleotides 4768 and 4769, and for the CS6 operon using oligonuncleotide 4740 and 4781.

One transconjugant which was positive for both these PCR reactions was processed in order to select derivatives in which the pJCB12-derivative plasmid had excised (described above). Colonies that grew on 5% sucrose agar were tested by PCR using the oligonucleotides 4749 and 4752 to identify EAST1 mutants. All colonies tested were negative by this PCR reaction indicating that the whole of the EAST1 region had been lost in these derivatives. Further PCR reactions were performed to test for the continued presence of the CS4 and CS6 genes as described above, and expression of CS6 was confirmed by SDS-PAGE.

PCR reactions using oligonucleotides LT-04 and LT-05 amplified a product of the expected size for the LT locus in the Strain J EAST1-negative derivative. Nucleotide sequence determination reactions using these same oligonucleotides showed that this fragment generated by PCR was indeed of the LT locus. Therefore, this locus was targeted using the pJCB12-ALT-A construct in the same way as described in Example 3. LT-negative derivatives were identified in which the whole of the LT locus had been deleted. Further PCR reactions to test for the presence of CS4 using oligonucleotides 4768 and 4769, and CS6 using the oligonucleotides 4740 and 4781 confirmed the continued presence of these loci in the LT-negative derivatives. The expression of CS6 by the Strain J EAST1-negative LT-negative derivatives was confirmed by SDS-PAGE.

PCR reactions performed using the oligonucleotides ST-01 and ST-02 indicated that the ST present in Strain J was that encoded by the transposon Tn1681 (41). The Strain J EAST1-negative LT-negative derivatives were tested by PCR using the oligonucleotides ST-01 and ST-02, and were shown to be ST-negative.

The aroC locus of the Strain J toxin-negative derivative was targeted using pJCB12-ΔaroC as described above for Strain H. Correctly targeted transconjugants were identified. Unusually, however, following growth on 5% sucrose medium all derivatives generated in a large number of experiments were identified as revertants. Therefore a new pJCB12-ΔaroC construct was made that incorporated a smaller deletion in the aroC locus. This was constructed by PCR amplification using oligonucleotides 47116 with 47118, and 47119 with 47117, to generate two DNA fragments flanking that region of the aroC gene to be deleted. These were then fused by an additional overlap extension PCR reaction using oligonucleotides 47116 with 47117, and the resulting fragment was cloned into pJCB12 using the XbaI and SacI restriction endonuclease sites. This construct was called pJCB12-ΔaroC$^J$ and was electrotransformed into SM10λpir. The sequence of the aroC gene and the binding sites of the oligonucleotides used to construct this novel deletion construct are shown in FIG. 11.

While pJCB12-ΔaroC$^J$ was undergoing construction, the ompC defined deletion mutation was introduced into the Strain J toxin-negative derivative using the pJCB12-ΔompC construct and procedure described for Strain H. One ompC defined deletion mutant was identified by PCR using oligonucleotides 4732 and 4743.

The defined aroC deletion mutation was then introduced into this Strain J toxin-negative ΔompC mutant using the new pJCB12-ΔaroC$^J$ construct by conjugation from strain SM10λpir. Colonies that grew on L-agar supplemented with chloramphenicol and tetracycline were screened by PCR using the oligonucleotides 4917 and 4742 in order to identify those in which the aroC gene had been correctly targeted. Transconjugants were then processed in order to select derivatives in which the pJCB12-derivative plasmid had excised (described above). Colonies that grew on 5% sucrose agar were tested by PCR using the oligonucleotides 4731 and TT20 in order to identify those with the incorporated defined aroC$^J$ deletion mutation.

The defined ompF deletion mutation was then incorporated into an identified Strain J toxin-negative ΔompC ΔaroC derivative. This was done exactly as described above for strain H, and one ompF deletion mutant was identified.

The tetracycline resistant plasmid pACYC-Tc was then specifically cured from the toxin-negative ΔompC ΔaroC ΔompF derivative of Strain J using pJCB12-pACYCori and then this plasmid itself was removed, again as described above for Strain H.

Finally, PCR reactions were performed to confirm the presence of CS4 using oligonucleotides 4768 with 4769, and CS6 using the oligonucleotides 4740 with 4781. Similarly the presence of the CFA/IV regulatory gene was confirmed using oligonucleotides 4785 and 4786. The nucleotide sequences of the defined aroC, ompC and ompF deletion mutations were determined as described for Strain H, and were as expected. The absence of EAST1, LT and ST loci were again confirmed by PCR as described above, expression of CS6 was confirmed by SDS-PAGE, and the LPS also was checked using SDS-PAGE.

Figure 12:
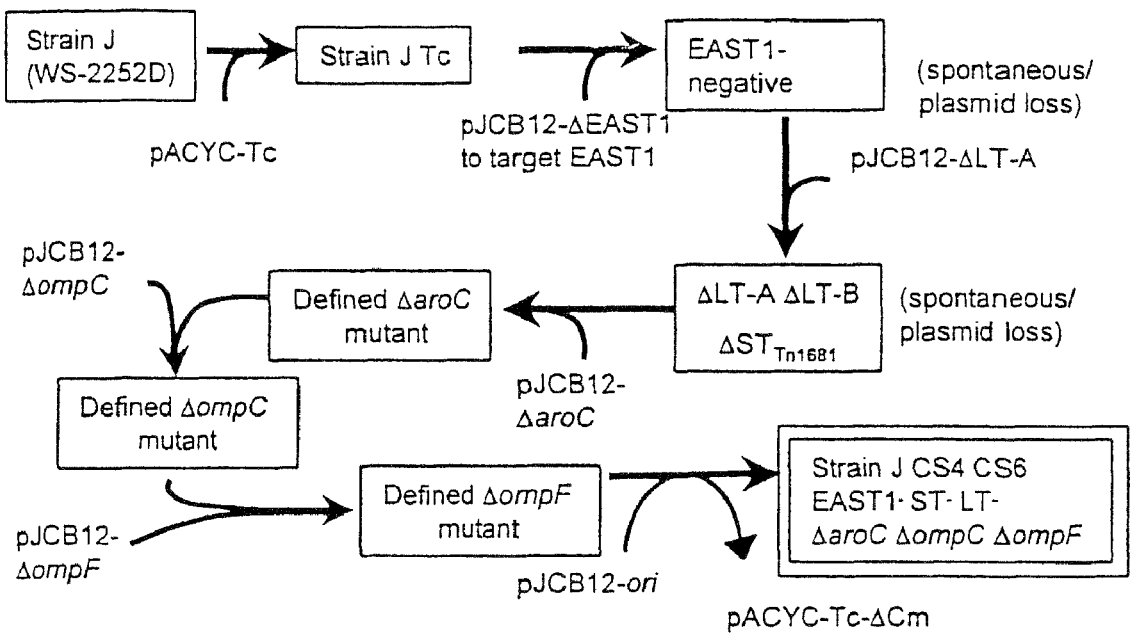
FIG. 12: Diagram of the individual stages involved in the attenuation of strain J.

A diagram showing all of the steps involved in these manipulations is shown in FIG. 12.

EXAMPLE 5

Increasing the Stability of Manipulated CFA Plasmids

This Example describes as an illustration one system for stabilising a CFA plasmid. The parDE locus was used as the stabilizing moiety.

In order to obtain a derivative of an ETEC strain that does not code for ST but continues to express its CFA genes, a pJCB12-ΔSTI derivative is constructed where the parDE locus is flanked by regions homologous to the regions flanking the ST gene in the plasmid to be targeted. Introduction of this plasmid into a recipient strain and selection on chloramphenicol will now result in transconjugants in which both loci are present in the CFA plasmid. The functional parDE locus will now ensure that this plasmid is maintained in these cells. Growth on sucrose to identify derivatives from which the pJCB12 component has been lost will now strongly select for cells containing a recombinant plasmid in which the desired cross over (ie the replacement of the ST structural gene with the parDE locus) has taken place. Cells in which a reversion event has occurred or from which the entire plasmid has been lost will be killed by the action of the toxin. Incorporation of the parDE locus will also function to stabilise the inheritance of the CFA plasmid during subsequent rounds of mutation, for example the introduction of additional attenuating mutations such as in the aroC, ompC and ompF genes.

Oligonucleotides 4789 and 4790 are used to amplify the parDE locus from plasmid RP4. The purified PCR product is then cloned into pJCB12-ΔSTI using the XhoI restriction enzyme sites to give plasmid pJCB12-ΔSTI::parDE. This plasmid is now introduced into a recipient strain by conjugation from SM10λpir or electro-transformation with purified plasmid DNA and the required intermediates and derivatives isolated by methods described in detail in the previous Examples.

EXAMPLE 6

Expression of LT-B in an Attenuated ETEC Strain, PTL003, to Induce a Protective Immune Response Against LT Aim The aim of this work was to express the B-subunit of *Escherichia coli* heat labile toxin in a vaccine strain of ETEC. The LTB gene was derived from strain WS2773-E (NAMRU3, Cairo, Egypt) but it could be derived from any LTB-encoding strain. Similarly the approach could be extended to include mutants of LT-A, LT-B fused to other proteins (eg ST) or to expression of CT-B or derivatives thereof. Initial plasmid constructs were designed to demonstrate that LT-B could be expressed in an ETEC vaccine strain in the absence of LT-A and could be correctly exported and assembled. Subsequent constructs used the native LT promoter to drive expression. Ultimately, a similar construct could be inserted into the chromosome of ETEC to create a stable strain without the need for antibiotic selection.

Methods

Section 1—PCR Amplification of the LTB CDS (Protein Coding Sequence)

Primers

Genbank sequences were used to design appropriate PCR primers (Table 1). The forward primer (Bfor) was designed to amplify from the start codon of the LTB gene and was based on Genbank sequence M17874 (17). To facilitate cloning into expression vectors, a BglII restriction site was included starting 8 bases 5' prime of the ATG start codon. The reverse primer (Brev) was designed to amplify from 200 bases downstream of the stop codon, such that any transcription terminators would be included in the PCR product, and was based on Genbank sequence AF190919 (26). An NheI restriction site was included in the primer to facilitate cloning into expression vectors.

Template

Plasmid DNA was isolated from Strain WS2773-E (NAMRU3, Cairo, Egypt) for use as a template.

| Reaction | | |
|---|---|---|
| Reaction mixture | | 2 µl plasmid DNA from WS2773-E (approx 50 ng/µl)<br>10 µl 10X Pfu DNA Polymerase buffer (Stratagene ™)<br>0.8 µl dNTPs (25 mM of each dNTP)<br>0.5 µl primer BFOR (258 ng/µl)<br>0.5 µl primer BREV (227 ng/µl)<br>84 µl H$_2$O<br>2 µl PfuTurbo ™ DNA Polymerase(2.5 U/µl) |
| Program | 1 cycle | 94° C. × 1 min |
|  | 30 cycles | 94° C. × 1 min<br>56° C. × 1 min<br>72° C. × 1 min |
|  | 1 cycle | 72° C. × 10 min |
|  | Hold | 4° C. |

Results

Figure 13:
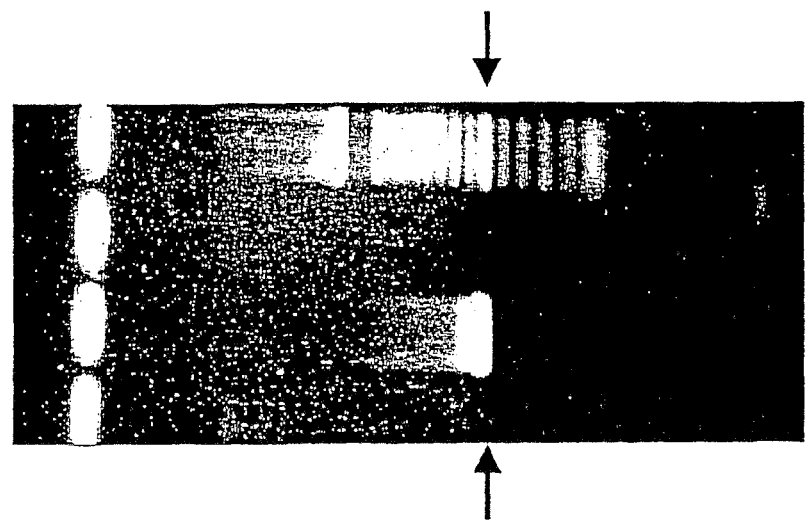
FIG. 13: Gel showing PCR amplified LT-B coding sequence from strain E. The left hand arrow indicates the LTB PCR product and the right hand arrow indicates a 600 bp marker.

A 600 bp PCR product was synthesized and isolated from a 1% agarose gel using a QIAquick™ gel extraction kit (Qiagen) according to the manufacturer's instructions (FIG. 13).

Section 2—Cloning of the LTB PCR Product

Cloning into pPCR-Script Amp SK+

Gel isolated PCR product was ligated into pPCR-Script Amp SK+™ (Stratagene) according to the instructions in the manufacturer's instruction manual (#211188). 2 µl of ligation mix was used to transform *E. coli* XL10-Gold™ Supercompetent cells (Stratagene #230350) and correct constructs were identified by digestion of purified plasmid DNA with PvuII. A correct construct was designated pPCRLTB. The LTB gene was fully sequenced (FIG. 14) and was compared to Genbank sequence M17874 (17). Four base changes were found which resulted in two amino acid changes. The PCR was repeated and a second clone was sequenced and gave identical results, showing that the LT-B sequence in strain WS2773-E differs from the database sequence.

Cloning into an Inducible Expression Vector

Figure 15:
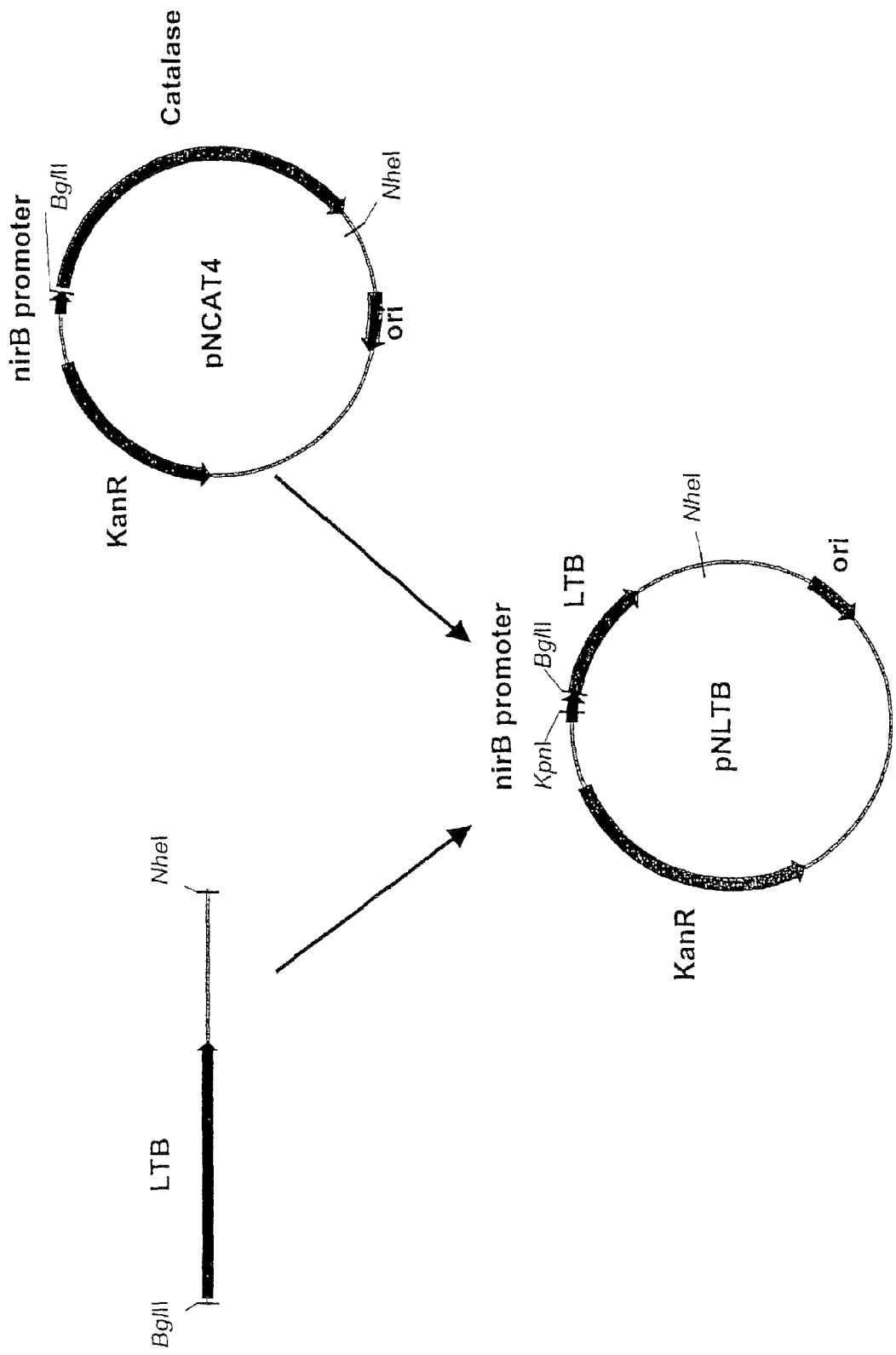
FIG. 15: Diagram showing construction of plasmid for the expression of LT-B under light of the problem of incorrect targeting we carried out sequencing. Our nucleotide sequence data obtained for the sacB region of pDM4 showed that it includes approximately 600 bp of an IS1-like insertion sequence, an insertion sequence which is prevalent in the genomes of many bacteria. We deduced that this could be at least partly responsible for the incorrect targeting.

The LTB gene was transferred into expression vector pNCAT4 (FIG. 15). pNCAT4 is an expression vector designed for use in *Salmonellas typhi* and *typhimurium*. The vector was originally derived from pTETnir15 (3) but had been modified by replacement of the TetC gene by the *H. pylori* catalase gene and replacement of the bla ampicillin resistance gene by a kanamycin resistance gene. In this plasmid the catalase gene is under the control of the nirB promoter which is upregulated in anaerobic conditions. For the purpose of the present invention many alternative expression plasmids which are well known in the art could be substituted for pNCAT4 or pTETnir15.

Plasmid pPCRLTB was digested with restriction enzymes BglII and NheI and a 600 bp fragment containing the LTB gene was isolated from a 1% agarose gel using a QIAquick™ gel extraction kit (Qiagen) according to the manufacturer's instructions. Plasmid pNCAT4 was digested with restriction enzymes BglII and NheI and a 2.6 kb vector fragment was isolated from a 1% agarose gel using a QIAquick™ gel extraction kit (Qiagen) according to the manufacturer's instructions.

The vector was ligated to the LTB gene (25) and the ligation mixture was used to transform *E. coli* XL10-Gold™ supercompetent cells (Stratagene #230350). Correct clones were identified by restriction enzyme analysis and one (designated pNLTB) was used to transform electrocompetent ETEC-PTL003.

Section 3—Expression and Localization of LTB in ETEC-PTL003

Sample Preparation

Cultures of PTL003 and PTL003-pNLTB were grown overnight in LB medium with appropriate antibiotics. Samples (1 ml) were diluted in 100 ml medium and grown with shaking for ~3 h. Flasks were transferred to a static incubator and growth was continued for a further 1.5 h.

Bacteria were fractionated into periplasmic and spheroplast components by the following method: Cells were harvested by centrifugation for 5 min at 10 400×g. The cell pellet was resuspended in 5 ml of 200 mM Tris HCl, pH8.0 and was transferred to a 50 ml glass beaker containing a magnetic flea. To this was added 5 ml of TES buffer (200 mM Tris HCl, pH 8.0, 1 mM Na$_2$EDTA, 1 M sucrose). Stirring was set in motion and a timer was started. At t=90 s, 1 mg of lysozyme (10 mg/ml solution) was added, and at t=135 s, 10 ml of water was added; the mixture was incubated at room temperature for a further 30 min. Spheroplast formation was checked with a light microscope and, if complete, the preparation was centrifuged for 20 min at 47 500×g at 20° C. The supernatant containing the periplasmic proteins was harvested and concentrated two-fold in a Centricon Macrosep™ spin-concentrator (3 000 NMWL, Millipore). The pellet, containing spheroplast proteins (cytoplasmic and membrane-bound), was resuspended in PBS. Samples of the cell fractions were mixed with equal quantities of Tris-Glycine SDS-PAGE sample buffer (Invitrogen LC267) containing 0.1 M dithiothreitol. A portion of the periplasmic sample was heated at 95° C. for 5 min, the remainder was kept at room temperature.

Sample Analysis

Samples were separated by electrophoresis on 18% Tris-Glycine Gels (Invitrogen EC6505) and transferred onto nitrocellulose membranes according to the instructions supplied with the Xcell II Blot Module™ (Invitrogen EI9051). Blots were incubated as follows:

| | |
|---|---|
| Block | 1 hour in PBS, 0.05% Tween 20 ™ containing 5% dried milk (Marvel ™) with gentle rocking. |
| Primary antibody | 1 hour with rabbit anti-cholera toxin antibody (Sigma C3062) diluted 1:10 000 in PBS, 0.05% Tween 20 ™ containing 1% Marvel and a 1:2 000 dilution of an *E. coli* extract (Promega #S3761). The antibody/extract mixture was pre-incubated for 1 hour before use to reduce non-specific binding to *E. coli* proteins. |
| Wash | Three 5 min washes in PBS, Tween 20 ™, 1% Marvel ™. |
| Secondary antibody | 1 hour with horseradish peroxidase conjugated anti-rabbit antibody (Sigma A4914) diluted 1:10 000 in PBS, 0.05% Tween 20 ™, 1% Marvel ™. |
| Wash | Three 5 min washes in PBS, Tween 20 ™, 1% Marvel ™. Two 5 min washes in PBS, Tween 20 ™ Two 5 min washes in PBS |
| Develop | Blots were developed using a SuperSignal West Pico Chemiluminescent Substrate ™ kit (Pierce). |

Figure 16:
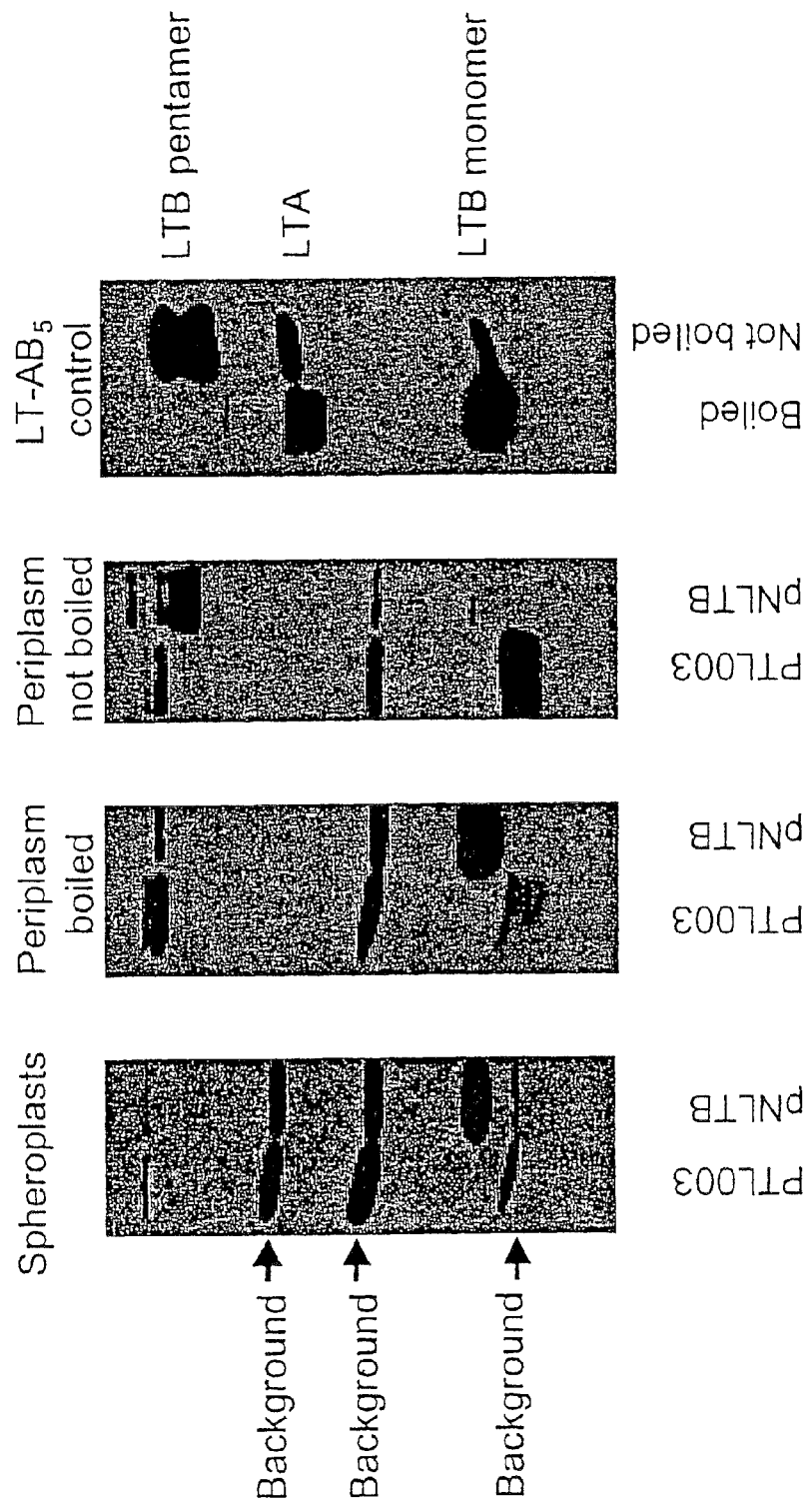

The results of the Western blots are presented in FIG. 16. LTB monomers were detected in both spheroplast and periplasmic boiled fractions. In the periplasmic samples kept at room temperature LTB pentamers were detected indicating that the LTB could be transported across the cell membrane and assembled in the normal way.

Section 4—PCR Amplification of the LTB Promoter

Primers

PCR primers were designed based on preliminary sequence data of the upstream region of the LTA gene of WS2773-E (FIG. 7). The forward primer (Pfor) annealed ~200 bp upstream of the LTA gene. A KpnI restriction site was included in the primer to facilitate cloning into expression vectors. The reverse primer (Prev) annealed just upstream of the start codon of the LTA gene and was designed to introduce a BglII restriction site to allow correct positioning of the promoter fragment with respect to the LTB gene.

Template

Plasmid DNA was isolated from Strain WS2773-E (NAMRU3, Cairo, Egypt) for use as a template.

Reaction

Reaction conditions were as described for the LTB gene in Section 1.

Results

Figure 17:
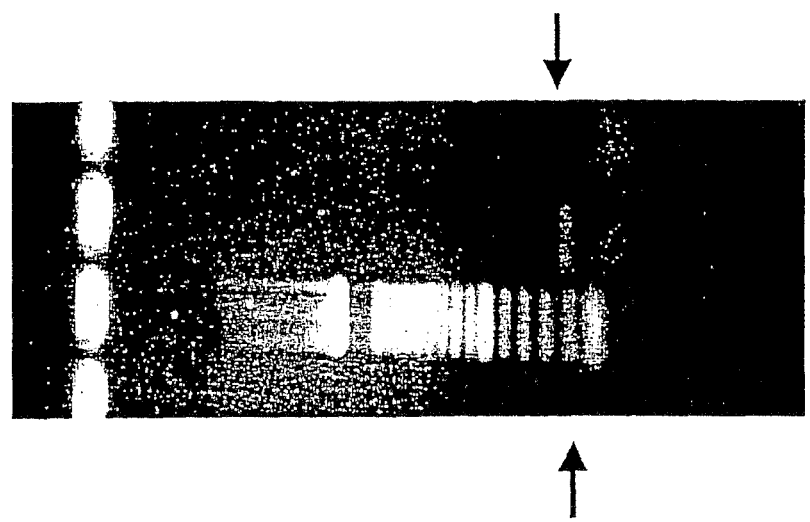

A 200 bp PCR product was synthesized and isolated from a 1% agarose gel using a QIAquick™ gel extraction kit (Qiagen) according to the manufacturer's instructions. (FIG. 17)

Section 5—Cloning of the LT Promoter

Cloning into pPCR-Script Amp SK+

Gel isolated PCR product was ligated into pPCR-Script Amp SK™+ (Stratagene) according to the instructions in the manufacturer's instruction manual (#211188). 2 µl of ligation mix was used to transform *E. coli* XL10-Gold™ Supercompetent cells (Stratagene #230350) and correct constructs were identified by digestion of purified plasmid DNA with PvuII. A correct construct was designated pPCRProm. The sequence of this construct is described in FIG. 18.

Cloning into an LTB Expression Vector

Plasmid pPCRProm was digested with KpnI and BglII and the 200 bp promoter fragment was isolated from a 1% agarose gel using a QIAquick™ gel extraction kit (Qiagen) according to the manufacturer's instructions. The nirB promoter of pNLTB was excised by digested with KpnI and BglII (FIG. 15) and the remaining 3.7 kb vector fragment was isolated from a 1% agarose gel using a QIAquick™ gel extraction kit (Qiagen) according to the manufacturer's instructions. The vector was ligated to the LT promoter fragment (Sambrook et al., 1989, ref 13) and the ligation mixture was used to transform *E. coli* XL10-Gold™ supercompetent cells (Stratagene #230350). Correct clones were identified by restriction enzyme analysis of purified plasmid DNA and one (designated pLLTB) was used to transform electrocompetent ETEC-PTL003.

Section 6—Expression of LTB Under the Control of the LT Promoter

Sample Preparation

Cultures of PTL003 and PTL003-pLLTB were grown overnight in LB medium with appropriate antibiotics. Absorbance at 600 mm was used to determine the concentration of cells in the cultures. Aliquots containing $5 \times 10^7$ cells were concentrated by centrifugation and the pellets were resuspended in 10 µl Tris-Glycine SDS-PAGE sample buffer (Invitrogen LC267) containing 0.1 M dithiothreitol.

Sample Analysis

Samples were analysed by SDS-PAGE (16) and Western blotting exactly as described in Section 3.

Figure 19:
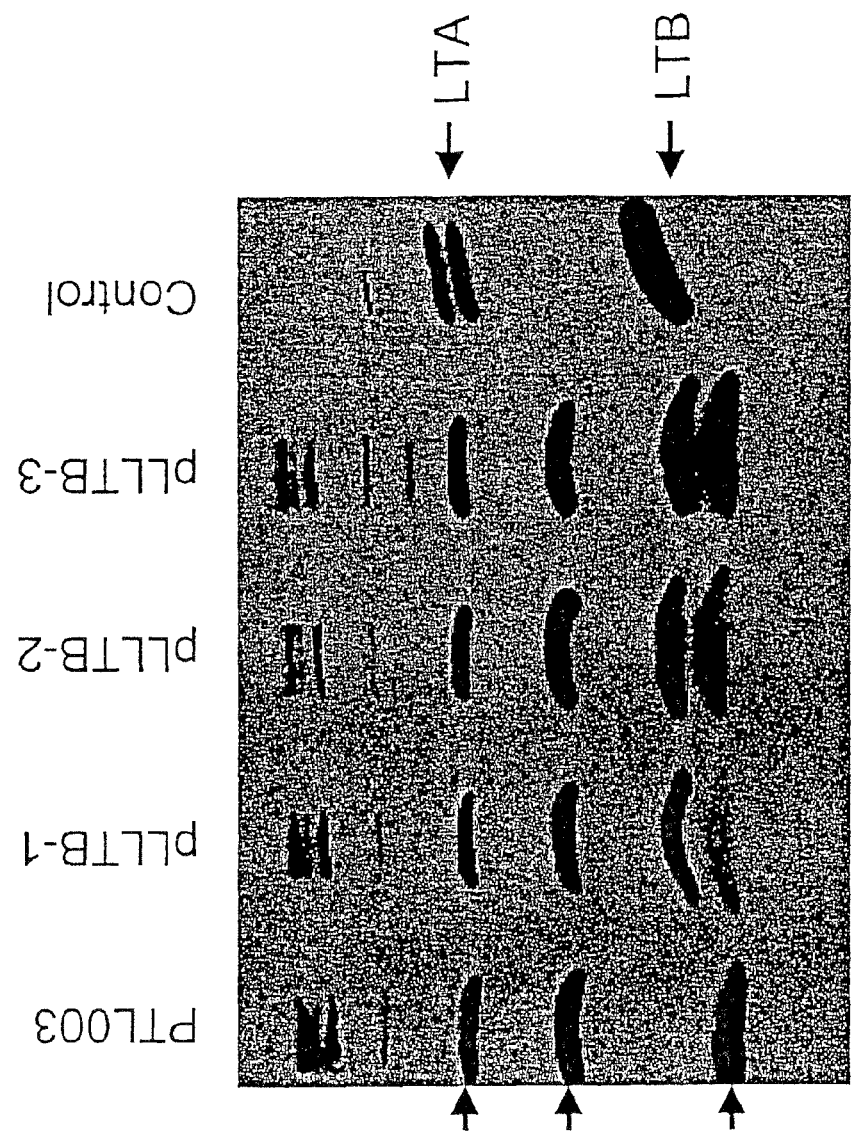

Results are presented in FIG. 19. LTB was expressed in PTL003 under the control of the LTAB promoter.

TABLE 1

Oligonucleotides used

| Name | Nucleotide sequence | Target locus; use |
|---|---|---|
| 4712 | 5'-GTAACTGCTAGCGTTGATCC | cotA; detection of CS2 locus |
| 4714 | 5'-TTCAACCTTAAAAGCTTTAAAAGCCT | oriR6K; construction of pJCB12 |
| 4715 | 5'-CTACACGAACTCTGAAGATCAGCAGTTCAACC | oriR6K; construction of pJCB12 |
| 4716 | 5'-GATCTTCAGAGTTCGTGTAGACTTTCCTTGG | mobRP4; construction of pJCB12 |
| 4717 | 5'-GCCACTGCAGCCTCGCAGAGCAGGATTC | mobRP4; construction of pJCB12 |
| 4718 | 5'-GGCACTGCAGGCGTAGCACCAGGCGTTT | cat; construction of pJCB12 |
| 4719 | 5'-TCATCCGGAGTTCCGTATGGCAAT | cat; construction of pJCB12 |

TABLE 1-continued

Oligonucleotides used

| Name | Nucleotide sequence | Target locus; use |
|------|---------------------|-------------------|
| 4720 | 5'-TGCCATACGGAACTCCGGATGAG | cat; construction of pJCB12 |
| 4721 | 5'-GCTTTTAAAGCTTTTAAGGTTGAATTCGATCGGCACGTAAGAGGTTC | cat; construction of pJCB12 |
| 4722 | 5'-GGCCTGCAGGCAAGACCTAAAATGTG | sacB; construction of pJCB12 |
| 4723 | 5'-GCGCTGCAGCTTTATGTTGATAAGAAA | sacB; construction of pJCB12 |
| 4727 | 5'-GCCGCATGCATTAATTCCATATATAGGGG | cfaC; detection of CFA/I |
| 4728 | 5'-GCCGTCGACTGCCATAAGGTAAACGAGC | cfaC; detection of CFA/I |
| 4731 | 5'-GAATTTTACGTCGATGAACGCG | aroC; confirmation of linkage with pJCB12 and mutation |
| 4732 | 5'-GTACAAATAACCTACAAAAAGCCC | ompC |
| 4733 | 5'-ACCCACACACGCTTAACGCTGG | ompF |
| 4738 | 5'-GGAAAGAGAGTATATCTATGTAACGC | detection of CS5 |
| 4739 | 5'-CGGTCGAGTAATAAGCTGTACTCTGC | detection of CS5 |
| 4740 | 5'-TAATTCTTGCTTCATTCGGCAGCC | cssA; detection of CS6 |
| 4741 | 5'-TAGTAACCAACCATAACCTGATCG | cssA; detection of CS6 |
| 4742 | 5'-CTTCACACTCCAGACTATCGGC | aroC; confirmation of mutation |
| 4743 | 5'-TTCCTGGCTCGGAATTTGAACC | ompC |
| 4746 | 5'-CGGCATGCCGCAATTGAATTGGGGG | eltB; construction of ΔLT-A |
| 4748 | 5'-AGAACTGCTGGGTATGTGGCTGG | EAST1; confirmation of linkage with pJCB12 |
| 4749 | 5'-GGCGTCGACGAAAATGAAGGGGCGAAGTTC | EAST1; construction of EAST1 deletion mutation |
| 4750 | 5'-ATGACACGAATGTTGATGGCATCCGGGAAGC | EAST1; construction of EAST1 deletion mutation |
| 4751 | 5'-GCCATCAACATTCGTGTCATGGAAGGACTAC | EAST1; construction of EAST1 deletion mutation |
| 4752 | 5'-GGCGCATGCAAGATTCGGCCAGTTAGCC | EAST1; construction of EAST1 deletion mutation |
| 4753 | 5'-GTTGGATAAGCGAAGAACGTGG | EAST1; to check for linkage with pJCB12 |
| 4760 | 5'-GCGGTCGACTGCGGCGAGCGGAAATGGC | ori pACYC184; construction of pJCB12-pACYCori |
| 4761 | 5'-GCCGAATTCAACTTATATCGTATGGGC | ori pACYC184; construction of pJCB12-pACYCori |
| 4762 | 5'-GGAAGTTGCGTCCATTTTACGGG | LT, construction of ΔLT-A |
| 4764 | 5'-AATATTACTATGCTCTTCGTAGCGG | ST strain A; construction of ST deletion mutation |
| 4765 | 5'-ATTAATAGCACCCGGTACAAGCAGG | ST strain A; construction of ST deletion mutation |
| 4766 | 5'-CAACAGTACTGCGATGAGTGG | cat; nucleotide sequence determinations into sacB |
| 4768 | 5'-CAATTGATATTTTGCAAGCTGATGG | csfA; detection of CS4 |
| 4769 | 5'-TAGAAACGACCCCACTATAATTTCC | csfA; detection of CS4 |
| 4772 | 5'-CCGTCGACTAAAAATCACCACCACTTC | LT, construction of ΔLT-A |
| 4773 | 5'-ATTCATCCTCCTTATATATCATACAAGAAGACAATCC | LT, construction of ΔLT-A |

TABLE 1-continued

Oligonucleotides used

| Name | Nucleotide sequence | Target locus; use |
|---|---|---|
| 4774 | 5'-GATATATAAGGAGGATGAATTATGAATAAAGTAAAATTT | LT, construction of ΔLT-A |
| 4775 | 5'-GTTCAATCCAGCATCAAATGAAG | detection of EAST1 |
| 4777 | 5'-GCCGCATGCCATTCGCCAGTCCTTCAA | detection of EAST1 |
| 4778 | 5'-CCAGGCGGTCACCGAACTCG | |
| 4779 | 5'-TTGAACAGAAAGAAAACTCGCACC | cotC; detection of CS2 |
| 4780 | 5'-ATGAATTCTCTCCAACGCTCTTCC | detection of CS5 |
| 4781 | 5'-AGTCAAATGTCCTGCATAAGTACC | cssB; detection of CS6 |
| 4783 | 5'-GGATATATCTTTTGGTGAAGATAAG | csvR; detection of CS5 regulator gene |
| 4784 | 5'-AATAAGATGCGCTAGAAATCCC | csvR; detection of CS5 regulator gene |
| 4785 | 5'-TATGGATATATATTCAGAAGAAGAG | cfaD; detection of CFA/I regulatory gene. |
| 4786 | 5'-AATAAGACGCACTGGAAATTCC | cfaD; detection of CFA/I regulatory gene |
| 4789 | 5'-GGCCTCGAGATTTTCCCGACCTTAATGCG | parDE; construction of pJCB12-ΔSTI$^B$::parDE |
| 4790 | 5'-CGGCTCGAGGACGTTGTGAGTGGCGCG | parDE; construction of pJCB12-ΔSTI$^B$::parDE |
| 4792 | 5'-GTGCTATTAATAATATAAAGGG | STI$^B$, nucleotide sequencing downstream of STI in StrainB |
| 4794 | 5'-TTTTCGGTCGCCGAAAAAGATAATA | STI, sequencing upstream of STI and confirmation of linkage |
| 4797 | 5'-GCGCTGTTCTTCAACTGTGG | STI$^B$, nucleotide sequencing downstream of STI in StrainB |
| 4798 | 5'-CCACAGTTGAAGAACAGCGC | STI$^B$, nucleotide sequencing downstream of STI in StrainB |
| 4799 | 5'-ATGTCGCCACGCATGACGGC | STI$^B$, construction of pJCB12-ΔSTI$^B$ |
| 47100 | 5'-CCGGCATGCGATGCCCTGCAGATGG | STI$^B$, construction of pJCB12-ΔSTI$^B$ |
| 47101 | 5'-GCCGTCGACTATGCTCTTCGTAGCGGAG | STI$^B$, construction of pJCB12-ΔSTI$^B$ |
| 47106 | 5'-GAACTTTTGCTGAGTTGAAGGAGC | STI$^E$, nucleotide sequencing downstream of STI in Strain E |
| 47112 | 5'-GGTCAGCCGGAATACGCGTT | STI$^E$, construction of pJCB12-ΔSTI$^E$ |
| 47113 | 5'-TCAGGCACAGCTAGCCGTCT | STI$^E$, confirmation of linkage of STI in Strain E |
| 47114 | 5'-ACAGCGCCTCGAGACTATTCATGCTTTCAGGACC | STI$^B$, construction of pJCB12-ΔSTI$^B$ |
| 47115 | 5'-GAATAGTCTCGAGGCGCTGTTCTTCAACTGTGG | STI$^B$, construction of pJCB12-ΔSTI$^B$ |
| 47116 | 5'-GCGTCTAGACACAACAATAACGGAGCCGTG | aroC; construction of pJCB12-ΔaroC$^J$ |
| 47117 | 5'-GGCGAGCTCGGAATATCAGTCTTCACATCGG | aroC; construction of pJCB12-ΔaroC$^J$ |
| 47118 | 5'-CCACGCCTTTCACCCCACCGCCGCGATAATCGC | aroC; construction of pJCB12-ΔaroC$^J$ |
| 47119 | 5'-CGCGGCGGTGGGGTGAAAGGCGTGGAAATTGGC | aroC; construction of pJCB12-ΔaroC$^J$ |
| 47120 | 5'-CATCAGAATCACTATTCATGCTTTCAGGACCAC | STI$^E$, construction of pJCB12-ΔSTI$^E$ |

TABLE 1-continued

Oligonucleotides used

| Name | Nucleotide sequence | Target locus; use |
|---|---|---|
| 47121 | 5'-CATGAATAGTGATTCTGATGATGTCTGTAACG | $STI^E$, construction of pJCB12-$\Delta STI^E$ |
| 4917 | 5'-ATCAACGGTGGTATATCCAGT | cat of pJCB12; confirmation of linkage. |
| Bfor | 5'-ACGTAGATCTTTATGAATAAAGTAAAATTTTATG | LT-B; |
| BglIIFOR | 5'-CCCAGATCTATATGCATAAATTATTCTATTTACTAAG | cfaB; detection of CFA/I |
| BglIImodREV | 5'-CACTTGGTAAAGACCTAATTAGAGCCGC | cfaB; detection of CFA/I |
| Brev | 5'-GTACGCTAGCCATGTATCTCATTAGCTG | LT-B; |
| CS3-02 | 5'-TTGTCGAAGTAATTGTTATA | detection of CS3 genes |
| CS3-03 | 5'-GTGAATGTATGAGGGATTCGA | detection of CS3 genes |
| CS3-06 | 5'-CTAAATGTTCGTTACCTTCAGTGG | detection of CS3 genes |
| EST-01 | 5'-CATGTTCCGGAGGTAATATGAA | detection of ST gene |
| LT-04 | 5'-CATCGCCATTATATGCAAATGGCG | eltA; detection of LT genes |
| LT-05 | 5'-ACTGATTGCCGCAATTGAATTGGG | eltB; detection of LT genes |
| Pfor | 5'-CCGGTACCATGATTCAATGTACACC | LT promoter |
| Prev | 5'-ACGTAGATCTACTTATATATCATACAAG | LT promoter |
| R6K-01 | 5'-GTGACACAGGAACACTTAACGGC | oriR6K; confirmation of linkage |
| RNS-03 | 5'-ACATCATAGCGATGGCATCAA | rns; detection of CFA/II regulatory gene |
| RNS-04 | 5'-TATTTCAATTCAGTTCGCATCGC | rns; detection of CFA/II regulatory gene |
| ST-01 | 5'-CATGACGGGAGGTAACATGA | Detection of $ST_{Tn1681}$ |
| ST-02 | 5'-TATGCTTTTTAATAACATCC | Detection of $ST_{Tn1681}$ |
| TT1 | 5'-ATCTGTTTGTTGAGCTCAGCAATCTATTTGCAACC | ompF |
| TT20 | 5'-ATGCGCGCGAGAGCTCAACCAGGGTCGCACTTTG | aroC |
| TT33 | 5'-TTGTAGCACTTTCACGGTAG | ompF; nucleotide sequence determinations across $\Delta ompF$ |
| TT35 | 5'-GATGGTGTGTTTATGCTC | aroC; nucleotide sequence determinations across $\Delta aroC$ |
| TT38 | 5'-GGAGAATGGACTTGCCGAC | ompC; nucleotide sequence determinations across $\Delta ompC$ |
| 47104 | 5'-TTATTGATGGAAGCTCAGGAGG | |
| 47105 | 5'-TAACGCCTGCTCTAACATTCCC | |
| 4792 | 5'-GTGCTATTAATAATATAAAGGG | |
| 4730 | 5'-TTCTTCACGAACTAATTGAGTG | |

The sequences shown in Table 1 are SEQ ID NOS: 8 to 103, respectively.

TABLE 2

| GenBank Accession numbers for sequence data | |
|---|---|
| EAST1 (astA) | AF143819 |
| ST (estA) | M18346 |
| LT-A (eltA) | V00275 |
| LT-B (eltB) | M17874 |
| CFA/I operon | M55661 |
| CS2 operon | Z47800 |
| CS3 operon | X16944 |
| CS4 operon | AF296132 |
| CS5 operon | AJ224079 |
| CS6 operon | U04844 |
| cfaD | M55609 |
| csvR | X60106 |
| rns | J04166 |
| parDE RK2 | L05507 |
| sacB | X02730 |

TABLE 2-continued

| GenBank Accession numbers for sequence data | |
|---|---|
| oriR6K | M65025 |
| mobRP4 | X54459 |
| cat | V00622 |

REFERENCES

1. Burkardt, H. J., G. Riess, and A. Puhler, *Relationship of group P1 plasmids revealed by heteroduplex experiments: RP1, RP4, R68 and RK2 are identical.* J Gen Microbiol, 1979. 114(2): p. 341-8.
2. Chatfield, S. N., et al., *Role of ompR-dependent genes in Salmonella typhimurium virulence: mutants deficient in both ompC and ompF are attenuated in vivo.* Infect Immun, 1991. 59(1): p. 449-52.
3. Chatfield, S. N., et al., *Use of the nirB promoter to direct the stable expression of heterologous antigens in Salmonella oral vaccine strains development of a single-dose oral tetanus vaccine.* Biotechnology (NY), 1992. 10(8): p. 888-92.
4. Chatfield, S. N., et al., *Evaluation of Salmonella typhimurium strains harbouring defined mutations in htrA and aroA in the murine salmonellosis model.* Microb Pathog, 1992. 12(2): p. 145-51.
5. Cravioto, A. 1980, PhD Thesis, University of London, London, United Kingdom.
6. Cravioto, A., et al., *Risk of diarrhea during the first year of life associated with initial and subsequent colonization by specific enteropathogens.* Am J Epidemiol, 1990. 131(5): p. 886-904.
7. Curtiss, R., 3rd and S. M. Kelly, *Salmonella typhimurium deletion mutants lacking adenylate cyclase and cyclic AMP receptor protein are avirulent and immunogenic.* Infect Immun, 1987. 55(12): p. 3035-43.
8. Donnenberg, M. S. and J. B. Kaper, *Construction of an eae deletion mutant of enteropathogenic Escherichia coli by using a positive-selection suicide vector.* Infect Immun, 1991. 59(12): p. 4310-7.
9. Dougan, G., et al., *Construction and characterization of vaccine strains of Salmonella harboring mutations in two different aro genes.* J Infect Dis, 1988. 158(6): p. 1329-35.
10. Everest, P., et al., *Expression of LacZ from the htrA, nirB and groE promoters in a Salmonella vaccine strain: influence of growth in mammalian cells.* FEMS Microbiol Lett, 1995. 126(1): p. 97-101.
11. Gerdes, K., P. B. Rasmussen, and S. Molin, *Unique type of plasmid maintenance function: postsegregational killing of plasmid-free cells.* Proc Natl Acad Sci USA, 1986. 83(10): p. 3116-20.
12. Gerdes, K., et al., *The hok killer gene family in gram-negative bacteria* New Biol, 1990. 2(11): p. 946-56.
13. Hohmann, E. L., et al., *phoP/phoQ-deleted Salmonella typhi (Ty800) is a safe and immunogenic single-dose typhoid fever vaccine in volunteers.* J Infect Dis, 1996. 173(6): p. 1408-14.
14. Hone, D., et al., *Construction of defined galE mutants of Salmonella for use as vaccines.* J Infect Dis, 1987. 156(1): p. 167-74.
15. Jones, P. W., et al., *Oral vaccination of calves against experimental salmonellosis using a double aro mutant of Salmonella typhimurium.* Vaccine, 1991. 9(1): p. 29-34.
16. Laemmli, U. K., *Cleavage of structural proteins during the assembly of the head of bacteriophage T4.* Nature, 1970. 227(259): p. 680-5.
17. Leong, J., A. C. Vinal, and W. S. Dallas, *Nucleotide sequence comparison between heat-labile toxin B-subunit cistrons from Escherichia coli of human and porcine origin.* Infect Immun, 1985. 48(1): p. 73-7.
18. Levine, M. M., et al., *Attenuated Salmonella as live oral vaccines against typhoid fever and as live vectors.* J Biotechnol, 1996. 44(1-3): p. 193-6.
19. Miller, S. I., A. M. Kukral, and J. J. Mekalanos, *A two-component regulatory system (phoP phoQ) controls Salmonella typhimurium virulence.* Proc Natl Acad Sci USA, 1989. 86(13): p. 5054-8.
20. Milton, D. L., et al., *Flagellin A is essential for the virulence of Vibrio anguillarum.* J Bacteriol, 1996. 178(5): p. 1310-9.
21. Pickard, D., et al., *Characterization of defined ompR mutants of Salmonella typhi: ompR is involved in the regulation of Vi polysaccharide expression.* Infect Immun, 1994. 62(9): p. 3984-93.
22. Qadri, F., et al., *Prevalence of toxin types and colonization factors in enterotoxigenic Escherichia coli isolated during a 2-year period from diarrheal patients in Bangladesh.* J Clin Microbiol, 2000. 38(1): p. 27-31.
23. Roberts, R. C., A. R. Strom, and D. R. Helinski, *The parDE operon of the broad-host-range plasmid RK2 specifies growth inhibition associated with plasmid loss.* J Mol Biol, 1994. 237(1): p. 35-51.
24. Rudin, A., L. Olbe, and A. M. Svennerholm, *Monoclonal antibodies against fimbrial subunits of colonization factor antigen I (CFA/I) inhibit binding to human enterocytes and protect against enterotoxigenic Escherichia coli expressing heterologous colonization factors.* Microb Pathog, 1996. 21(1): p. 35-45.
25. Sambrook, J., E. F. Fritsch, and T. Maniatis, *Molecular cloning: a loboratory manual.* 2nd ed. 1989: Cold Spring Harbor Laboratory Press, Cold Spring Harbor, N.Y.
26. Schlor, S., et al., *Genetic rearrangements of the regions adjacent to genes encoding heat-labile enterotoxins (eltAB) of enterotoxigenic Escherichia coli strains.* Appl Environ Microbiol, 2000. 66(1): p. 352-8.
27. Strugnell, R., et al., *Characterization of a Salmonella typhimurium aro vaccine strain expressing the P.69 antigen of Bordetella pertussis.* Infect Immun, 1992. 60(10): p. 3994-4002.
28. Svennerholm, A. M., et al., *Roles of different coli surface antigens of colonization factor antigen II in colonization by and protective immunogenicity of enterotoxigenic Escherichia coli in rabbits.* Infect Immun, 1990. 58(2): p. 341-6.
29. Tacket, C. O., et al., *Enteral immunization and challenge of volunteers given enterotoxigenic E. coli CFA/II encapsulated in biodegradable microspheres.* Vaccine, 1994. 12(14): p. 1270-4.
30. Tacket, C. O. and M. M. Levine, *Vaccines against enterotoxigenic Escherichia coli infections*, in *New Generation Vaccines*, M. M. Levine, et al., Editors. 1997, Marcel Dekker, Inc., New York, N.Y.
31. Tao, B. Y. and K. C. P. Lee, *Mutagenesis by PCR*, in *PCR Technology: current innovations*, H. G. Griffin and A. M. Griffin, Editors. 1994, CRC Press, Inc.: Boca Raton, Fla. p. 69-83.
32. Turner, A. K., et al., *Construction and characterization of genetically defined aro omp mutants of enterotoxigenic*

33. Wolf, M. K., *Occurrence, distribution, and associations of O and H serogroups, colonization factor antigens, and toxins of enterotoxigenic Escherichia coli.* Clin Microbiol Rev, 1997. 10(4): p. 569-84.
34. Yamamoto, T. and P. Echeverria, *Detection of the enteroaggregative Escherichia coli heat-stable enterotoxin 1 gene sequences in enterotoxigenic E. coli strains pathogenic for humans.* Infect Immun, 1996.64(4): p. 1441-5.
35. Dougan EP-B 0322237.
36. Dougan EP-B 0400958.
37. Dougan EP-B 0524205.
38. Chatfield WO 99/49026.
39. Charles WO 92/15689.
40. Chang, A. C. and S. N. Cohen, *Construction and characterization of amplifiable multicopy DNA cloning vehicles derived from the P15A cryptic miniplasmid.* J Bacteriol, 1978. 134(3): p. 1141-56.
41. So, M. and B. J. McCarthy, *Nucleotide sequence of the bacterial transposon Tn1681 encoding a heat-stable (ST) toxin and its identification in enterotoxigenic Escherichia coli strains.* Proc Natl Acad Sci USA, 1980. 77(7): p. 4011-5.
42. Echeverria, P., et al., *Plasmids coding for colonization factor antigens I and II, heat-labile enterotoxin, and heat-stable enterotoxin A2 in Escherichia coli.* Infect Immun, 1986. 51(2): p. 626-30.
43. Levine, M. M., et al., *Colonization factor antigens I and II and type 1 somatic pili in enterotoxigenic Escherichia coli: relation to enterotoxin type.* Infect Immun, 1983. 39(2): p. 889-97.
44. McConnell, M. M., et al., *Plasmids coding for colonization factor antigen I and heat-stable enterotoxin production isolated from enterotoxigenic Escherichia coli: comparison of their properties.* Infect Immun, 1981. 32(2): p. 927-36.
45. Murray, B. E., et al., *CFA/I-ST plasmids: comparison of enterotoxigenic Escherichia coli (ETEC) of serogroups O25, O63, O78, and O128 and mobilization from an R factor-containing epidemic ETEC isolate.* J Bacteriol, 1983. 153(1): p. 566-70.
46. Reis, M. H., et al., *Transfer of a CFA/I-ST plasmid promoted by a conjugative plasmid in a strain of Escherichia coli of serotype O128ac:H12.* Infect Immun, 1980. 29(1): p. 140-3.
47. Simon, R., U. Priefer, and A. Puhler, *A broad host range mobilisation system for in vivo genetic engineering: transposon mutagenesis in Gram negative bacteria.* Bio/Technology, 1983. 1: p. 784-791.
48. Turner et al (1998) Infection and Immunity 66(5)2099-2106.
49. Tacket et al, 1997, Infection & Immunity, 65 (2), 452 to 456.
50. Cieplak et al (1995) Journal of Biol. Chem. 270(51), 30545-30550.
51. Chong et al (1998) Vaccine 16, 732-740.
52. Rappuoli et al (1999) Immunology Today 20(11), 493-500.
53. Clements (1990) Infect. & Immun. 58(5), 1159-1166.
54. Aitken and Hirst (1993) Vaccine 11(2), 227-233.
55. Sanchez et al (1990) Res. Microbiol. 141, 971-979.
56. Miller, V. L. and J. J. Mekalanos, *Synthesis of cholera toxin is positively regulated at the transcriptional level by toxR.* Proc Natl Acad Sci USA, 1984. 81(11): p. 3471-5.
57. Dunstan, S., Simmons, C. and Strugnell, R. *Use of in-vivo regulated promoters to to deliver antigens from attenuated Salmonella typhimurium.* Infection and Immunity (1999) 67, 5133-5141.
58. Valdivia, R. and Falkow, S. *Fluorescence-based isolation of bacterial genes expressed within host cells.* Science (1997), 277, 2007-2011.
59. Summers et al, Mol. Genet. Genes., 201(2): 334-338.

The invention claimed is:

1. A live bacterial cell which expresses colonization factor antigen CFA/I from a native plasmid but does not express heat stable toxin (ST) owing to deletion or inactivation of the ST gene and does not express heat labile toxin (LT), wherein the bacterium is attenuated by deletion or inactivation of one or more genes selected from the group consisting of aroA, aroC, aroD, aroE, pur, htrA, ompC, ompF, ompR, cya, crp, phoP, surA, rfaY, dksA, hupA, sipC and clpB.

2. A cell according to claim 1 which is an *Escherichia coli* cell.

3. A cell according to claim 1 wherein the plasmid is an enterotoxigenic *E. coli* plasmid in which the ST gene is deleted.

4. A cell according to claim 1 which does not express EAST1.

5. A cell according to claim 1 which does not express an antibiotic resistance gene.

6. A cell according to claim 1 which is obtainable by a method comprising site-directed deletion or inactivation of the LT gene.

7. A cell according to claim 1 wherein the plasmid contains an element which enhances its stability.

8. A cell according to claim 7 wherein said element is a toxin-antitoxin element or a recombinase recognition element.

9. A cell according to claim 7 wherein the stability element is parDE or crs.

10. A cell according to claim 1 which is attenuated by deletion or inactivation of at least one aro gene and at least one omp gene.

11. A cell according to claim 1 which is attenuated by deletion or inactivation of each of aroC, ompF and ompC.

12. A cell according to claim 1 which expresses a heterologous antigen.

13. A cell according to claim 12 wherein the heterologous antigen is an *E. coli* antigen.

14. A cell according to claim 13 wherein the heterologous antigen is an *E. coli* colonization factor antigen (CFA).

15. A cell according to claim 13 wherein the heterologous antigen is a non-toxic component or form of LT.

16. A cell according to claim 15 wherein the non-toxic component of LT is the B subunit.

17. An *Escherichia coli* cell deposited with the European Collection of Cell Cultures (ECACC) under accession number 01090304, number 01090305, number 01090306, number 02082964, number 02082966, number 02082967 or number 02082968; or a descendent of a said cell that expresses B subunit of *Escherichia coli* LT.

* * * * *

SEQUENCE LISTING

<160> NUMBER OF SEQ ID NOS: 103

<210> SEQ ID NO 1
<211> LENGTH: 950
<212> TYPE: DNA
<213> ORGANISM: Escherichia coli

<400> SEQUENCE: 1

```
ttttcggtcg ccgaaaaaga taatattact atgctcttcg tagcggagag tatagtatga      60
tgttcatcac aaaaaaaata aaaaagtttg cgcaaccgtt ctgattttga ttcaaatgtt     120
cgtggatgcc atgttccgga ggtaatatga agaaatcaat attatttatt tttctttctg     180
tattgtcttt ttcacctttc gctcaggatg ctaaaccagt agagtcttca aaagaaaaaa     240
tcacactaga atcaaaaaaa tgtaacattg caaaaaaaag taataaaagt ggtcctgaaa     300
gcatgaatag tagcaattac tgctgtgaat tgtgttgtaa tcctgcttgt accgggtgct     360
attaataata taagggaac taaacagttc cctttatatt tgtgtgcgcc gtggctggcg     420
ctgttcttca actgtggagg ctgaagaacg actaagaggt gaaagtcctc cacacacccg     480 gtgagggaa gtgttagcgg aaggcaaggt gatcctaccc acgtaatatg gacacaggcc     540
taagcgaggt tctggttta aattgctccg gactgaggcc gccacaccaa ctgtgccgcc     600
gccaccgatt gtaatcacat tcgatataat taaataccgt tgcccgcatt atttcccggc     660
```

```
tgataaagtg ttctccatgg atacattcca ctttcagcga atgaaagaag ctttccacgc    720
aggcattatc gtagcagcaa cctttttgcgc tcatactttc cacgcagatt atgccgcttc   780
agttgcgcct gataatctgc tgaacagtac tggcctccac ggtccgtgtg aacgataacg    840
ttccggggcc tcttacgccg ccacagcgcc atctgcaggg catcgcaggc cagttgcgcc    900
gtcatgcgtg gcgacattga ccagccaata acggcacgtg accacaggtc              950
```

<210> SEQ ID NO 2
<211> LENGTH: 1330
<212> TYPE: DNA
<213> ORGANISM: Escherichia coli

<400> SEQUENCE: 2

```
gttgggttga gcctgtacat agatttgtgt aattgcctga ttttgatatg ttcaatccag     60
catcaaatga aggttaattt atggacgaaa aacagttaca gactctggct aacgaactgg    120
ccaaaaacct caaacccct gaagaccttca gtcagtttga tcggctgctg aaaaagctca    180
gcgttgaagc cgctctcaat gcagagatga cacaccatct tgggtatgag aaaaatcagt    240
ccagaccagg agctaactcc cgcaacggtt attccacaaa gaccgttatc acaggcgacg    300
gtccactgga actgcgtact ccgcgcgatc gtgacggtac cttcgaacca caactggtaa    360
agaaaaatca gacccgtatt accgggatgg ataaccagat cctctcgttg tatgccaaag    420
ggatgaccac ccgtgagata gccgctgcgt tcaaagaact gtatgacgca gatgtttcac    480
cggcactgat atcaaggtt accgatgccg tgatggagca ggttgtagaa tggcaaaacc    540
gaccactgga tgctgtttac cccattgttt atcttgactg tatcgtcctg aaagttcggc    600
aggacagtcg cgtcatcaac aaatcggtgt tcctggcact gggcatcaat atcgaaggtc    660
agaaagaact gctgggtatg tggctggccg aaaatgaagg ggcgaagttc tggctcaatg    720
tgctgactga actgaaaaac cgcggtctga acgatatcct catcgcctgt gtggatggcc    780
tgaaaggctt cccggatgcc atcaacacag tatatccgaa ggcccgcatc cagttatgca    840
tcgtgcatat ggtgcgcaac agcctgcgct tcgtgtcatg gaaggactac aaagccgtca    900
ctcgcgacct gaaagcgatt tatcaggctc ccacggaaga ggcaggtcag caggccctgg    960
aagcgttcgc tgccggcctgg gacagtcgct atcctcagat aagccgaagc tggcaggcta   1020
actggccgaa tcttgccacg ttcttcgctt atccaacgga catccgcaaa gtgatctata   1080
cgacgaatgc catcgagtcg ctaaacagcg tgatccgcca tgcgatcaaa aagcgtaaag   1140
tgttcccgac agacgactcg gtgaaaaaag tggtgtggct ggcaatccag tctgcgtccc   1200
ggaaatggac gatgccgttg aaggactggc gaatggcaat gagccgcttt attatcgagt   1260
tcggtgaccg cctggacggt cacttctgag aaaggcattt acacagaata ctaaacaggc   1320
tcgttgggtt                                                         1330
```

<210> SEQ ID NO 3
<211> LENGTH: 944
<212> TYPE: DNA
<213> ORGANISM: Escherichia coli
<220> FEATURE:
<221> NAME/KEY: SITE
<222> LOCATION: 29, 45, 46, 128
<223> OTHER INFORMATION: n denotes an unspecified nucleotide

<400> SEQUENCE: 3

```
ggttgacccg ctgaaatgca ttctttgcng aagtcagatg tggtnnacgg gactgaagag     60
gggctaccgt ctggcagagc tggtcgggat gcatgagcca ctggcgcgac agcgggtgtg    120
```

```
cggctganag ccgcagaggg gaagttgcgt ccatttttacg ggggatggag ccaaaaaaac      180
cgccaatcat accctgtatc aatcagagtc atcctgttta atagtcattt ctgttcatat      240
ggtgcacaag gagtgttgaa gcaacatccg ttttgtggtg ttttttttaat cttttttggga     300 ttttaattcc tatcgatgaa caggcgtttc agcggtcggg actaaaaatc accaccactt      360
cgggtcatcc gccttcatct ccgcttctgt ttcgtataaa tcaaaacgac ggcaggtatg      420
gcagaacgtg acgtattcgt gcggtgaatc cgggtacatt ttgtggaagg tttcccagaa      480
acagaccgtg caggagggat gaccggcgat aaagtctgta aatacggact gataagggtg      540
attattggct ctggcgacgg cttttcagaac ctctttcacc attctggtgt ggactttctg      600
gtgctccagg ttgtgtgaca tgggaactca ttctggatgg ttactctgaa agcccatatt      660 ctgcccccc ccgatttgca gccgccaggc tgccgtggtt caagtcgcga ctaataaaaa       720
taatcaggtt gccatgattc aatgtacacc tttctcacat tcgtctccgg catgaaaacg      780
atgcactctt cctttatcgc tttcactaca cattttatcc tcgcatggat gtttataaaa      840
aacatgattg acatcatgtt gcatatatgt taaataaaac aagtggcgtt atcttttttcc     900 ggattgtctt cttgtatgat ataaagttt tcctcgatga aaa                         944

<210> SEQ ID NO 4
<211> LENGTH: 1183
<212> TYPE: DNA
<213> ORGANISM: Escherichia coli

<400> SEQUENCE: 4
aataaaaaag tttgcgcaac cgttctgatt ttgatacaaa tgttcgtgga tgccatgttc       60
cggaggtaat atgaagaaat caatattatt tattttttctt tctgtattgt cttttttcacc   120 tttcgctcag gatgctaaac cagtagagtc ttcaaaagaa aaaatcacac tagaatcaaa     180
aaaatgtaac attgcaaaaa aagtaataa aagtggtcct gaaagcatga atagtagcaa      240
ttactgctgt gaattgtgtt gtaatcctgc ttgtaccggg tgctattaat aatataaagg     300
gaactaaaca gttcccttta tatttggtct gattctgatg atgtctgtaa cgtatgtacc     360
tgttgctttg ttgaataaat cgaacttttg ctgagttgaa ggagcagagc acgcatcatc     420
cggcaacatg agtcgttcca tggcaaagca gaagttcaga atcaccaact ggcgcagcca     480
caacaaagcc cttatcctcc gtggcaccat cactttctgg cgggatggcg aggcaattca    540
ggcctggtat gagtcagcaa ccccctcatc acggggacga cctcagcgtt attctgacct    600
tgctattacc actttttttg tgattaaacg cgtattccgg ctgaccgacc ctgcgggctt     660
gaactgcccc cgaaagttgg acagtttatt gttagacggc tagctgtgcc tgagtccggt    720
attcttaccc gggctcaggc catttaacct tgagctaatc cgctcattgt taatcgatat    780
actcctcgac tactcttcga cgctctttt tactataata agcttttttct gcttcagccg     840 ggactccata ccgcgctgat gcctgccgtt ccattcctgc tgtgtaagcg tcaacggagc    900
accgtattga cgctcattta ttggtgagta ctacgttcca tggcaggagt tcgccaactc    960
ggttggaagg ccattccggc agtacgctca gaatatggcg cagatacgct tccggatcga   1020
taccgttcag acggcaggtg ccgatcatgc ccgtacagca gtgctccacg ctcgcccgcc   1080
gtgatcgcta ccgaagaaca cgtaattttt cttttcccgag accagacttg cacgaaagcg   1140
ctctttccgc tggtattgtc cgctctgcca gaccgtatta cac                      1183

<210> SEQ ID NO 5
<211> LENGTH: 3100
```

<212> TYPE: DNA
<213> ORGANISM: Escherichia coli

<400> SEQUENCE: 5

| | | | | | |
|---|---|---|---|---|---|
| ctggaggaat | acgtggataa | aattttcgtt | gatgaagcag | taaatgagct | gcaaaccatt | 60 |
| caggacatgt | tgcgctggtc | ggtgagccgc | ttcagcgcgg | caaatatctg | gtacggtcac | 120 |
| ggtaccgata | acccgtggga | tgaagccgta | cagctggtgt | tgccttcgct | ctacctgccg | 180 |
| ctggatattc | cggaagatat | gcgcaccgcg | cgtctgacct | ccagcgaaaa | acaccgtatt | 240 |
| gttgaacgcg | tgatccgccg | cgtcaatgaa | cgcattccgg | tggcttacct | gaccaacaaa | 300 |
| gcgtggttct | gcggccatga | attttacgtc | gatgaacgcg | tgctggtgcc | gcgctcgccg | 360 |
| attggtgaac | tgatcaacaa | taaatttgcc | ggacttatca | gcaagcaacc | gcagcatatt | 420 |
| ttagatatgt | gtactggtag | cggctgcatc | gccattgcct | gtgcttatgc | cttcccggat | 480 |
| gcagaagtcg | acgcggtgga | tatctctcca | gacgcgctgg | cggttgctga | acagaacatc | 540 |
| gaagaacacg | gtctgatcca | aacgtcatt | ccgattcgtt | ccgatctgtt | ccgcgacttg | 600 |
| ccgaaagtgc | agtacgacct | gattgtcact | aacccgccgt | atgtcgatgc | ggaagatatg | 660 |
| tccgacctgc | aaacgaata | ccgccacgag | ccggaactgg | gcctggcatc | tggcactgac | 720 |
| ggcctgaaac | tgacgcgtcg | cattctcggt | aacgcggcag | attaccttgc | tgatgatggc | 780 |
| gtgttgattt | gtgaagtcgg | caacagcatg | gtacatctta | tggaacaata | tccggatgtt | 840 |
| ccgttcacct | ggctggagtt | tgataacggc | ggcgatggtg | tgtttatgct | caccaaagag | 900 |
| cagcttattg | ccgcacgaga | acatttcgcg | atttataaag | attaagtaaa | cacgcaaaca | 960 |
| caacaataac | ggagccgtga | tggctggaaa | cacaattgga | caactctttc | gcgtaaccac | 1020 |
| cttcggcgaa | tcgcacgggc | tggcgctcgg | ctgcatcgtc | gatggtgttc | cgccaggcat | 1080 |
| tccgctgacg | gaagcggacc | tgcaacatga | cctcgaccgt | cgtcgccctg | ggacatcgcg | 1140 |
| ctataccacc | cagcgccgcg | agccggatca | ggtcaaaatt | ctctccggtg | tttttgaagg | 1200 |
| cgttactacc | ggcaccagca | ttggcttgtt | gatcgaaaac | actgaccagc | gctctcagga | 1260 |
| ttacagtgcg | attaaggacg | ttttccgtcc | aggccatgcc | gattacacct | acgaacaaaa | 1320 |
| atacggtctg | cgcgattatc | gcggcggtgg | acgttcttcc | gcccgcgaaa | ccgccatgcg | 1380 |
| cgtggcggca | ggagctattg | ccaaaaaata | tctcgccgag | aaatttggta | ttgaaatccg | 1440 |
| tggctgcctg | acccagatgg | cgacattcc | gctggatatc | aaagactggt | cgcaggtcga | 1500 |
| gcaaaatccg | ttttttgcc | cggaccccga | caaaatcgac | gcgttagacg | agttgatgcg | 1560 |
| tgcgctgaaa | aaagagggcg | actccatcgg | cgctaaagtc | accgttgttg | ccagtggcgt | 1620 |
| tcctgccgga | cttggcgagc | cggtctttga | ccgcctggat | gctgacatcg | cccatgcgct | 1680 |
| gatgagcatc | aacgcggtga | aaggcgtgga | aattggcgac | ggctttgacg | tggtggcgct | 1740 |
| gcgcggcagc | cagaaccgcg | atgaaatcac | caaagacggt | ttccagagca | accatgcggg | 1800 |
| cggcattctc | ggcggtatca | gcagcgggca | gcaaatcatt | gcccatatgg | cgctgaaacc | 1860 |
| gacctccagc | attaccgtgc | cgggtcgtac | cattaaccgc | tttggcgaag | aagttgagat | 1920 |
| gatcaccaaa | ggccgtcacg | atccctgtgt | cgggatccgc | gcagtgccga | tcgcagaagc | 1980 |
| gatgctggcg | atcgttttaa | tggatcacct | gttacggcaa | cgggcgcaaa | atgccgatgt | 2040 |
| gaagactgat | attccacgct | ggtaaaaaat | gaataaaacc | gcgattgcgc | tgctggctct | 2100 |
| gcttgccagt | agcgccagcc | tggcagcgac | gccgtggcaa | aaaataaccc | aacctgtgcc | 2160 |
| gggtagcgca | caatcgatag | gcagttttc | taatggctgt | attgtcggcg | ctgacacgct | 2220 |
| gccgatacag | tccgaacatt | atcaggtcat | gcgtaccgat | cagcgtcgct | atttcggtca | 2280 |

```
cccggatctg gtgatgttta tccagcgtct gagtagccag gtgagcaatc tgggcatggg    2340
tacggtgctg attggcgata tggggatgcc cgctggtggg cgtttcaacg gcggtcatgc    2400
cagccaccag accggactgg atgtcgatat ctttctgcaa ctgccgaaaa ctcgctggac    2460
ctccgcgcag ctcttgcgcc cgcaagcact ggacttagtt tcccgcgacg gtaaacacgt    2520
tgtctccacg ctgtggaagc cagaaatttt cagcttgatc aaactcgccg cccaggacaa    2580
agacgtcacg cgcatttttg ttaatccggc gattaaacaa caactttgcc ttgatgcggg    2640
caccgatcgc gactggttgc gcaaagtgcg accctggttc cagcatcgcg cgcatatgca    2700
tgtacgatta cgttgccctg ccgatagtct ggagtgtgaa gatcaacctt taccgccatc    2760
aggcgatggt tgcggggcag aactgcaaag ctggtttgaa cctccaaaac cgggaacaac    2820
aaagcctgag aagaagacac cgcctccgtt gccgccttcc tgccaggcgc tactggatga    2880
gcacgtgatc taatgaaaac gtttaatagc ctgtttatgg tttccccgct gttgctggga    2940
gttctctttt ttgtcgccat gctggcggga tttatcgact cgattgccgg tggcggtggg    3000
ttactcacca ttccggcatt gatggcagcg gggatgtctc ccgctaatgc gctggcaacc    3060
aataaactgc aagcctgcgg cggctctatt tccgctacta                         3100
```

```
<210> SEQ ID NO 6
<211> LENGTH: 375
<212> TYPE: DNA
<213> ORGANISM: Escherichia coli

<400> SEQUENCE: 6
atgaataaag taaaatttta tgttttattt acggcgttac tatcctctct atgtgcacac      60
ggagctcccc agtctattac agaactatgt tcggaatatc gcaacacaca aatatatacg     120
ataaatgaca aaatactatc atatacggaa tcgatggcag gcaaaagaga atggttatc      180 attacattta agagcggcgc aacatttcag gtcgaagtcc cggcagtca acatatagac      240 tcccaaaaaa aagccattga aaggatgaag gacacattaa gaatcgcata tctgaccgag     300
accaaaattg ataaattatg tgtatggaat aataaaaccc ccaattcaat tgcggcaatc     360
agtatggaaa actag                                                     375
```

```
<210> SEQ ID NO 7
<211> LENGTH: 213
<212> TYPE: DNA
<213> ORGANISM: Escherichia coli

<400> SEQUENCE: 7
ccggtaccat gattcaatgt acacctttct cacattcgtc tccggcatga aaacgatgca      60
ctcttccttt atcgctttca ctacacattt tatcctcgca tggatgttta taaaaaacat     120
gattgacatc atgttgcata tatgttaaat aaaacaagtg gcgttatctt tttccggatt     180
gtcttcttgt atgatatata agtagatcta cgt                                 213
```

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gtaactgcta gcgttgatcc                                                  20
```

```
<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
ttcaacctta aaagctttaa aagcct                                          26

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
ctacacgaac tctgaagatc agcagttcaa cc                                   32

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
gatcttcaga gttcgtgtag actttccttg g                                    31

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
gccactgcag cctcgcagag caggattc                                        28

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
ggcactgcag gcgtagcacc aggcgttt                                        28

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
tcatccggag ttccgtatgg caat                                            24

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
```
tgccatacgg aactccggat gag                                          23

<210> SEQ ID NO 16
<211> LENGTH: 47
<212> TYPE: DNA
<213> ORGANISM: Artificial Sequence
<220> FEATURE:
<223> OTHER INFORMATION: Primer

<400> SEQUENCE: 16
gcttttaaag cttttaaggt tgaattcgat cggcacgtaa gaggttc                47

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
ggcctgcagg caagacctaa aatgtg                                       26

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
gcgctgcagc tttatgttga taagaaa                                      27

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
gccgcatgca ttaattccat atatagggg                                    29

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
gccgtcgact gccataaggt aaacgagc                                     28

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gaattttacg tcgatgaacg cg                                           22

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
gtacaaataa cctacaaaaa gccc                                              24

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
acccacacac gcttaacgct gg                                                22

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
ggaaagagag tatatctatg taacgc                                            26

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
cggtcgagta ataagctgta ctctgc                                            26

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
taattcttgc ttcattcggc agcc                                              24

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
tagtaaccaa ccataacctg atcg                                              24

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
cttcacactc cagactatcg gc                                                22

```
<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
ttcctggctc ggaatttgaa cc                                            22

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
cggcatgccg caattgaatt ggggg                                         25

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
agaactgctg ggtatgtggc tgg                                           23

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
ggcgtcgacg aaaatgaagg ggcgaagttc                                    30

<210> SEQ ID NO 33
<211> LENGTH: 31
<212> TYPE: DNA
<213> ORGANISM: Artificial Sequence
<220> FEATURE:
<223> OTHER INFORMATION: Primer

<400> SEQUENCE: 33
atgacacgaa tgttgatggc atccgggaag c                                  31

<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34
gccatcaaca ttcgtgtcat ggaaggacta c                                  31

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
```
ggcgcatgca agattcggcc agttagcc                                    28

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
gttggataag cgaagaacgt gg                                          22

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
gcggtcgact gcggcgagcg gaaatggc                                    28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
gccgaattca acttatatcg tatggggc                                    28

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
ggaagttgcg tccattttac ggg                                         23

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
aatattacta tgctcttcgt agcgg                                       25

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
attaatagca cccggtacaa gcagg                                       25

<210> SEQ ID NO 42
<211> LENGTH: 21
<212> TYPE: DNA
<213> ORGANISM: Artificial Sequence

```
<220> FEATURE:
<223> OTHER INFORMATION: Primer

<400> SEQUENCE: 42
caacagtact gcgatgagtg g                                              21

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
caattgatat tttgcaagct gatgg                                          25

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
tagaaacgac cccactataa tttcc                                          25

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
ccgtcgacta aaaatcacca ccacttc                                        27

<210> SEQ ID NO 46
<211> LENGTH: 37
<212> TYPE: DNA
<213> ORGANISM: Artificial Sequence
<220> FEATURE:
<223> OTHER INFORMATION: Primer

<400> SEQUENCE: 46
attcatcctc cttatatatc atacaagaag acaatcc                             37

<210> SEQ ID NO 47
<211> LENGTH: 39
<212> TYPE: DNA
<213> ORGANISM: Artificial Sequence
<220> FEATURE:
<223> OTHER INFORMATION: Primer

<400> SEQUENCE: 47
gatatataag gaggatgaat tatgaataaa gtaaaattt                           39

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
gttcaatcca gcatcaaatg aag                                            23
```

```
<210> SEQ ID NO 49
<211> LENGTH: 27
<212> TYPE: DNA
<213> ORGANISM: Artificial Sequence
<220> FEATURE:
<223> OTHER INFORMATION: Primer

<400> SEQUENCE: 49
gccgcatgcc attcgccagt ccttcaa                                        27

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
ttgaacagaa agaaaactcg cacc                                           24

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
atgaattctc tccaacgctc ttcc                                           24

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
agtcaaatgt cctgcataag tacc                                           24

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
ggatatatct tttggtgaag ataag                                          25

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
aataagatgc gctagaaatc cc                                             22

<210> SEQ ID NO 55
<211> LENGTH: 25
<212> TYPE: DNA
<213> ORGANISM: Artificial Sequence
<220> FEATURE:
<223> OTHER INFORMATION: Primer

<400> SEQUENCE: 55
```
tatggatata tattcagaag aagag       25

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
aataagacgc actggaaatt cc       22

<210> SEQ ID NO 57
<211> LENGTH: 29
<212> TYPE: DNA
<213> ORGANISM: Artificial Sequence
<220> FEATURE:
<223> OTHER INFORMATION: Primer

<400> SEQUENCE: 57
ggcctcgaga ttttcccgac cttaatgcg       29

<210> SEQ ID NO 58
<211> LENGTH: 27
<212> TYPE: DNA
<213> ORGANISM: Artificial Sequence
<220> FEATURE:
<223> OTHER INFORMATION: Primer

<400> SEQUENCE: 58
cggctcgagg acgttgtgag tggcgcg       27

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
gtgctattaa taatataaag gg       22

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
ttttcggtcg ccgaaaaaga taata       25

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gcgctgttct tcaactgtgg       20

<210> SEQ ID NO 62
<211> LENGTH: 20
<212> TYPE: DNA
<213> ORGANISM: Artificial Sequence

```
<220> FEATURE:
<223> OTHER INFORMATION: Primer

<400> SEQUENCE: 62
ccacagttga agaacagcgc                                              20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
atgtcgccac gcatgacggc                                              20

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
ccggcatgcg atgccctgca gatgg                                        25

<210> SEQ ID NO 65
<211> LENGTH: 28
<212> TYPE: DNA
<213> ORGANISM: Artificial Sequence
<220> FEATURE:
<223> OTHER INFORMATION: Primer

<400> SEQUENCE: 65
gccgtcgact atgctcttcg tagcggag                                     28

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66
gaacttttgc tgagttgaag gagc                                         24

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ggtcagccgg aatacgcgtt                                              20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tcaggcacag ctagccgtct                                              20
```

```
<210> SEQ ID NO 69
<211> LENGTH: 34
<212> TYPE: DNA
<213> ORGANISM: Artificial Sequence
<220> FEATURE:
<223> OTHER INFORMATION: Primer

<400> SEQUENCE: 69
acagcgcctc gagactattc atgctttcag gacc                    34

<210> SEQ ID NO 70
<211> LENGTH: 33
<212> TYPE: DNA
<213> ORGANISM: Artificial Sequence
<220> FEATURE:
<223> OTHER INFORMATION: Primer

<400> SEQUENCE: 70
gaatagtctc gaggcgctgt tcttcaactg tgg                     33

<210> SEQ ID NO 71
<211> LENGTH: 30
<212> TYPE: DNA
<213> ORGANISM: Artificial Sequence
<220> FEATURE:
<223> OTHER INFORMATION: Primer

<400> SEQUENCE: 71
gcgtctagac acaacaataa cggagccgtg                         30

<210> SEQ ID NO 72
<211> LENGTH: 31
<212> TYPE: DNA
<213> ORGANISM: Artificial Sequence
<220> FEATURE:
<223> OTHER INFORMATION: Primer

<400> SEQUENCE: 72
ggcgagctcg gaatatcagt cttcacatcg g                       31

<210> SEQ ID NO 73
<211> LENGTH: 33
<212> TYPE: DNA
<213> ORGANISM: Artificial Sequence
<220> FEATURE:
<223> OTHER INFORMATION: Primer

<400> SEQUENCE: 73
ccacgccttt cacccaccg ccgcgataat cgc                      33

<210> SEQ ID NO 74
<211> LENGTH: 33
<212> TYPE: DNA
<213> ORGANISM: Artificial Sequence
<220> FEATURE:
<223> OTHER INFORMATION: Primer

<400> SEQUENCE: 74
cgcggcggtg gggtgaaagg cgtggaaatt ggc                     33

<210> SEQ ID NO 75
<211> LENGTH: 33
<212> TYPE: DNA
<213> ORGANISM: Artificial Sequence
<220> FEATURE:
<223> OTHER INFORMATION: Primer

<400> SEQUENCE: 75
```
catcagaatc actattcatg ctttcaggac cac 33

<210> SEQ ID NO 76
<211> LENGTH: 32
<212> TYPE: DNA
<213> ORGANISM: Artificial Sequence
<220> FEATURE:
<223> OTHER INFORMATION: Primer

<400> SEQUENCE: 76
catgaatagt gattctgatg atgtctgtaa cg 32

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
atcaacggtg gtatatccag t 21

<210> SEQ ID NO 78
<211> LENGTH: 34
<212> TYPE: DNA
<213> ORGANISM: Artificial Sequence
<220> FEATURE:
<223> OTHER INFORMATION: Primer

<400> SEQUENCE: 78
acgtagatct ttatgaataa agtaaaattt tatg 34

<210> SEQ ID NO 79
<211> LENGTH: 37
<212> TYPE: DNA
<213> ORGANISM: Artificial Sequence
<220> FEATURE:
<223> OTHER INFORMATION: Primer

<400> SEQUENCE: 79
cccagatcta tatgcataaa ttattctatt tactaag 37

<210> SEQ ID NO 80
<211> LENGTH: 28
<212> TYPE: DNA
<213> ORGANISM: Artificial Sequence
<220> FEATURE:
<223> OTHER INFORMATION: Primer

<400> SEQUENCE: 80
cacttggtaa agacctaatt agagccgc 28

<210> SEQ ID NO 81
<211> LENGTH: 28
<212> TYPE: DNA
<213> ORGANISM: Artificial Sequence
<220> FEATURE:
<223> OTHER INFORMATION: Primer

<400> SEQUENCE: 81
gtacgctagc catgtatctc attagctg 28

<210> SEQ ID NO 82
<211> LENGTH: 20
<212> TYPE: DNA
<213> ORGANISM: Artificial Sequence

```
<220> FEATURE:
<223> OTHER INFORMATION: Primer

<400> SEQUENCE: 82
ttgtcgaagt aattgttata                                              20

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
gtgaatgtat gagggattcg a                                            21

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
ctaaatgttc gttaccttca gtgg                                         24

<210> SEQ ID NO 85
<211> LENGTH: 22
<212> TYPE: DNA
<213> ORGANISM: Artificial Sequence
<220> FEATURE:
<223> OTHER INFORMATION: Primer

<400> SEQUENCE: 85
catgttccgg aggtaatatg aa                                           22

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
catcgccatt atatgcaaat ggcg                                         24

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
actgattgcc gcaattgaat tggg                                         24

<210> SEQ ID NO 88
<211> LENGTH: 25
<212> TYPE: DNA
<213> ORGANISM: Artificial Sequence
<220> FEATURE:
<223> OTHER INFORMATION: Primer

<400> SEQUENCE: 88
ccggtaccat gattcaatgt acacc                                        25
```

<210> SEQ ID NO 89
<211> LENGTH: 28
<212> TYPE: DNA
<213> ORGANISM: Artificial Sequence
<220> FEATURE:
<223> OTHER INFORMATION: Primer

<400> SEQUENCE: 89
acgtagatct acttatatat catacaag                                    28

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
gtgacacagg aacacttaac ggc                                         23

<210> SEQ ID NO 91
<211> LENGTH: 21
<212> TYPE: DNA
<213> ORGANISM: Artificial Sequence
<220> FEATURE:
<223> OTHER INFORMATION: Primer

<400> SEQUENCE: 91
acatcatagc gatggcatca a                                           21

<210> SEQ ID NO 92
<211> LENGTH: 23
<212> TYPE: DNA
<213> ORGANISM: Artificial Sequence
<220> FEATURE:
<223> OTHER INFORMATION: Primer

<400> SEQUENCE: 92
tatttcaatt cagttcgcat cgc                                         23

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
catgacggga ggtaacatga                                             20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
tatgcttttt aataacatcc                                             20

<210> SEQ ID NO 95
<211> LENGTH: 35
<212> TYPE: DNA
<213> ORGANISM: Artificial Sequence
<220> FEATURE:
<223> OTHER INFORMATION: Primer

<400> SEQUENCE: 95

```
atctgtttgt tgagctcagc aatctatttg caacc                              35
```

<210> SEQ ID NO 96
<211> LENGTH: 34
<212> TYPE: DNA
<213> ORGANISM: Artificial Sequence
<220> FEATURE:
<223> OTHER INFORMATION: Primer

<400> SEQUENCE: 96

```
atgcgcgcga gagctcaacc agggtcgcac tttg                               34
```

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97

```
ttgtagcact ttcacggtag                                               20
```

<210> SEQ ID NO 98
<211> LENGTH: 18
<212> TYPE: DNA
<213> ORGANISM: Artificial Sequence
<220> FEATURE:
<223> OTHER INFORMATION: Primer

<400> SEQUENCE: 98

```
gatggtgtgt ttatgctc                                                 18
```

<210> SEQ ID NO 99
<211> LENGTH: 19
<212> TYPE: DNA
<213> ORGANISM: Artificial Sequence
<220> FEATURE:
<223> OTHER INFORMATION: Primer

<400> SEQUENCE: 99

```
ggagaatgga cttgccgac                                                19
```

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100

```
ccaggcggtc accgaactcg                                               20
```

<210> SEQ ID NO 101
<211> LENGTH: 22
<212> TYPE: DNA
<213> ORGANISM: Artificial Sequence
<220> FEATURE:
<223> OTHER INFORMATION: Primer

<400> SEQUENCE: 101

```
ttattgatgg aagctcagga gg                                            22
```

<210> SEQ ID NO 102
<211> LENGTH: 22
<212> TYPE: DNA
<213> ORGANISM: Artificial Sequence

```
                                          -continued
<220> FEATURE:
<223> OTHER INFORMATION: Primer

<400> SEQUENCE: 102
taacgcctgc tctaacattc cc                                               22

<210> SEQ ID NO 103
<211> LENGTH: 22
<212> TYPE: DNA
<213> ORGANISM: Artificial Sequence
<220> FEATURE:
<223> OTHER INFORMATION: Primer

<400> SEQUENCE: 103
ttcttcacga actaattgag tg                                               22
```